(12) United States Patent
Ford et al.

(10) Patent No.: US 8,193,239 B2
(45) Date of Patent: Jun. 5, 2012

(54) SUBSTITUTED 1-CYANOETHYLHETERO-CYCLYLCARBOXAMIDE COMPOUNDS

(75) Inventors: Rhonan Ford, Leicestershire (GB); Andrew Mather, Leicestershire (GB); Antonio Mete, Leicestershire (GB); Ian Millichip, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 58 days.

(21) Appl. No.: 12/774,996

(22) Filed: May 6, 2010

(65) Prior Publication Data

US 2010/0286118 A1   Nov. 11, 2010

Related U.S. Application Data

(60) Provisional application No. 61/185,629, filed on Jun. 10, 2009, provisional application No. 61/176,279, filed on May 7, 2009.

(51) Int. Cl.
*A61K 31/351* (2006.01)
(52) U.S. Cl. ......... 514/451; 549/424; 549/425
(58) Field of Classification Search ......... 549/424, 549/425
See application file for complete search history.

(56) References Cited

U.S. PATENT DOCUMENTS

2006/0247289 A1   11/2006   Qian et al.

FOREIGN PATENT DOCUMENTS

| WO | WO00/34241 | 6/2000 |
|---|---|---|
| WO | WO01/09110 | 2/2001 |
| WO | WO01/47886 | 7/2001 |
| WO | WO03/002531 | 1/2003 |
| WO | WO03/002553 | 1/2003 |
| WO | WO2004/110988 | 12/2004 |

OTHER PUBLICATIONS

Bondebjerg et al. "Dipeptidyl nitriles as human dipeptidyl peptidase I inhibitors" Bioorganic & Medicinal Chemistry Letters. 2006 (16) 3614-3617.

*Primary Examiner* — James O Wilson
*Assistant Examiner* — Brian McDowell
(74) *Attorney, Agent, or Firm* — Fish & Richardson P.C.

(57) ABSTRACT

The present invention provides compounds of formula (I)

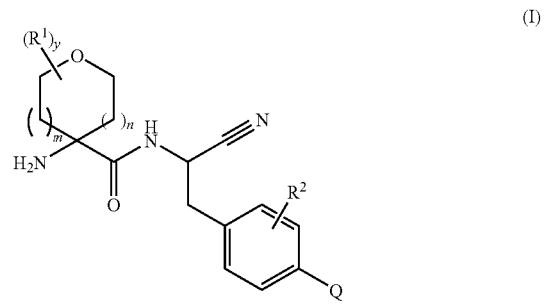

in which y, m, n, $R^1$, $R^2$ and Q are as defined in the specification, a process for their preparation, pharmaceutical compositions containing them and their use in therapy.

9 Claims, 7 Drawing Sheets

SUBSTITUTED 1-CYANOETHYLHETERO-CYCLYLCARBOXAMIDE COMPOUNDS

This application is entitled to priority pursuant to U.S.C. 35 §119(e) to U.S. Provisional Application Ser. No. 61/176,279, filed May 7, 2009, and Provisional Application Ser. No. 61/185,629, filed Jun. 10, 2009, which is incorporated herein by reference in its entirety.

The present invention relates to nitrile compounds, processes for their preparation, pharmaceutical compositions containing them and their use in therapy.

Dipeptidyl peptidase I (DPPI; EC 3.4.14.1), also known as cathepsin C, is a lysosomal cysteine protease belonging to the papain family having a molecular weight of 200 kDa. DPPI was first discovered by Gutman and Fruton in 1948 (*J Biol Chem*, 174, 851-858); however, the cDNA of the human enzyme was first described in 1995 (Paris et al. 1995, *FEBS Leu*, 369, 326-330). DPPI is the only member of the papain family that is functional as a tetramer, consisting of four identical subunits. Each subunit is composed of an N-terminal fragment, a heavy chain and a light chain (Dolenc et al. 1995, *J Biol Chem*, 270, 21626-21631).

DPPI is constitutively expressed in many tissues with highest levels in lung, kidney, liver and spleen. DPPI catalyses the removal of dipeptides from the N-terminal end of polypeptide substrates with broad specificity. Recent data suggest that besides being an important enzyme in lysosomal protein degradation, DPPI also functions as a key enzyme in the activation of granule serine proteases in cytotoxic T lymphocytes and natural killer cells (granzymes A and B), mast cells (chymase and tryptase) and neutrophils (cathepsin G and elastase).

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the MC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion.

Neutrophils play a critical role in host defense against invading pathogens. Neutrophils are produced in the bone marrow and are fully mature when released into the circulation to take up their role as the first line of cellular defense. Pro-inflammatory mediators and chemotactic attractants activate neutrophils and draw them to the site of infection, where they act to engulf bacteria by phagocytosis, assaulting them with an arsenal of anti-bacterial compounds that use both oxidative and non-oxidative methods of attack. The powerful serine protease, neutrophil elastase, is one of those anti-bacterial compounds that are clearly involved in destroying bacteria. Neutrophil elastase is released into the phagolysome surrounding the microorganism, which it proceeds to destroy. Neutrophil elastase is able to attack the outer membrane protein, OmpA, in gram-negative bacteria, helping to directly kill the pathogen by degrading its membrane, as well as enabling other anti-bacterial compounds to gain access to the pathogen. In addition, neutrophil elastase may help process other anti-bacterial compounds, converting them from inactive pro-peptides into their active states, such as for cathelicidin.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defense against infection by degrading phagocyte surface receptors and opsonins. Its negative role is illustrated by its involvement in the tissue destruction and inflammation that characterise numerous diseases, including hereditary emphysema, chronic obstructive pulmonary disease, cystic fibrosis, adult respiratory distress syndrome, ischemic-reperfusion injury and rheumatoid arthritis.

There is strong evidence associating tryptase and chymase with a number of mast cell mediated allergic, immunological and inflammatory diseases. The fact that neutrophil elastase, cathepsin G and proteinease 3 also seem to play significant roles in these types of diseases point to DPPI being a valid therapeutic target due to its central role in activating these proteases (Adkison et al. 2002, *J Clin Invest*, 109, 363-271; Pham et al. 2004, *J Immunol*, 173, 7277-7281).

It is known from the International Patent Application WO 2004/110988, that certain nitrile derivatives are inhibitors of DPPI. One of the disclosed compounds (S)-2-amino-N—((S)-2-(biphenyl-4-yl)-1-cyanoethyl)butanamide.

There is no disclosure in this document of a nitrile compound which bears a saturated oxygen-containing heterocycle (for example tetrahydro-2H-pyran) between the $NH_2$ and amide groups. We have now found that such compounds possess potent DPPI activity and/or have desirable pharmacological activity profiles (for example stability in human liver microsomes).

In accordance with the present invention, there is therefore provided a compound of formula (I)

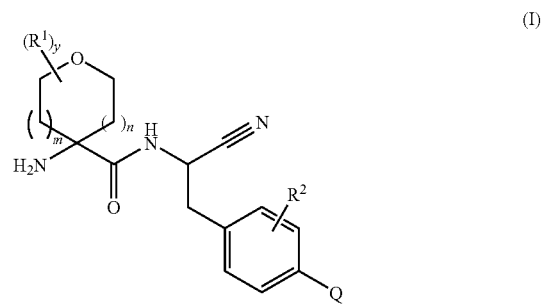

is wherein y represents 0, 1 or 2;

m and n are independently 0, 1, 2 or 3 (such that the sum of m and n is equal to 1, 2 or 3);

$R^1$ is $C_{1-3}$alkyl optionally substituted with one or more substituents selected from halogen, hydroxy or $C_{1-3}$alkoxy;

$R^2$ is selected from hydrogen, halogen, CN, $CF_3$, $C_{1-3}$alkyl or $C_{1-3}$alkoxy;

Q represents phenyl, a 5- to 10-membered heteroaryl ring system which contains at least one ring heteroatom independently selected from nitrogen, oxygen and sulphur, or Q is of the formula A:

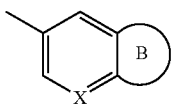

wherein X is CH or N and B is a 5- or 6-membered heterocyclic ring containing 1 to 3 ring heteroatoms independently selected from nitrogen, oxygen and sulphur;
the phenyl, heteroaryl ring system and ring system of the formula A being optionally substituted by 1 to 3 substituents independently selected from halogen, carboxyl, hydroxyl, oxo, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy (optionally substituted by halogen), $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl;
$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;
v is 0, 1 or 2;
$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;
$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;
each $R^{57}$, $R^{58}$, $R^{61}$, $R^{62}$ $R^{63}$, and $R^{64}$ independently represents a hydrogen atom or a $C_{1-6}$alkyl or $C_{3-6}$cycloalkyl group;
$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring;
or a pharmaceutically-acceptable salt thereof.

DEFINITIONS

Unless otherwise stated, halogen is Cl, F, Br or I;
Unless otherwise stated, cycloalkyl is a non-aromatic carbocyclic ring containing the requisite number of carbon atoms, optionally containing, where possible, up to 3 double bonds, and optionally substituted with 1 to 3 substituents selected from ($C_1$-$C_6$)alkyl, ($C_1$-$C_6$)alkoxy, —OH, —CN and halo, and wherein each substituent may be the same or different. Examples of suitable cycloalkyl groups include cyclopropyl, cyclobutyl, cyclopentyl, cyclohexyl, cycloheptyl, cyclopentene, cyclopenta-1,3-diene, cyclohexene and cyclohexa-1,4-diene (optionally substituted as stated above).
Examples of alkoxy groups optionally substituted by halogen include fluoromethoxy, difluoromethoxy, trifluoromethoxy and 2,2,2-trifluoroethoxy.
Examples of suitable heteroaryl groups include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3, 5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzoxazinyl, benzothiazinyl, benzimidazolyl, benzothiazolyl, indazolyl, benzofurazanyl, quinolyl, isoquinolyl, quinazolinyl, quinoxalinyl or naphthyridinyl more preferably furyl, thienyl, isoxazolyl, thiazolyl, pyridyl, benzothienyl, benzofurazanyl or quinolyl.
Examples of ring system A include:

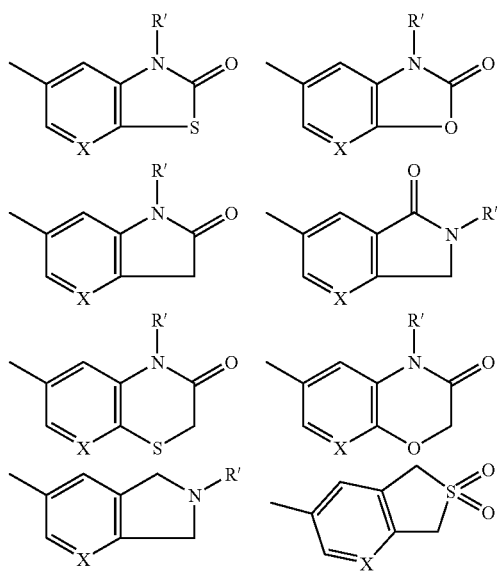

wherein X is as hereinabove defined, R' is selected from hydrogen and $C_{1-6}$alkyl optionally substituted by $C_{1-4}$alkyoxy, and the ring system being optionally further substituted as hereinabove defined. In another aspect, the ring system A has no further substituents.

Unless otherwise stated alkyl and alkoxy groups containing the requisite number of carbon atoms can be branched or unbranched. Examples of suitable alkyl groups include methyl, ethyl, n-propyl, i-propyl, n-butyl, sec-butyl and t-butyl. Examples of suitable alkoxy groups include methoxy (—$OCH_3$), ethoxy (—$OCH_2CH_3$), n-propoxy, i-propoxy, n-butoxy, sec-butoxy and t-butoxy.

A saturated 4- to 7-membered heterocyclic ring may be partially unsaturated but not fully unsaturated. A heterocyclic ring will contain at least one ring heteroatom selected from nitrogen, oxygen and sulphur.

For the avoidance of doubt, it should be understood that the definitions of the heterocyclic rings in formula (I) are not intended to include unstable structures or any O—O, O—S or S—S bonds and that a substituent, if present, may be attached to any suitable ring atom provided the resulting compound is not unstable.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, tosylates, benzenesulfonates, maleates, fumarates, xinafoates, p-acetamidobenzoates, succinates, ascorbates, oleates, bisulfates, furoates, propionates, stearates, isethionates and the like.

In one embodiment, pharmaceutically acceptable salts may include salts of pharmaceutically acceptable organic acids, especially carboxylic and sulfonic acids, including, but not limited to, acetate, adipate, alginate, ascorbate, aspartate, benzenesulfonate (besylate), benzoate, butyrate, camphorate, camphorsulfonate, camsylate, citrate, p-chlorobenzenesulfonate, cyclopentate, 2,5-dichlorobesylate, digluconate, edisylate, esylate, fumarate, formate, gluconate, glucoheptanoate, glutamate, glutarate, glycerophosphate, glycolate, heptanoate, hexanoate, hippurate, 2-hydroxyethane sulfonate, lactate, lactobionate, laurate, malate, maleate, malonate, mandelate, methanesulfonate, 2-naphthalenesulfonate, napsylate, nicotinate, orotate, oxalate, pantothenate, pamoate, pamoic, pectinate, 3-phenylpropionate, pivalate, propionate, pivalate, saccharin, salicylate, stearate, succinate, tartrate, trans-cinnamate, trifluoroacetate, xinafoate, xylate (p-xylene-2-sulfonic acid), undecanoate; and of inorganic acids such as hydrobromide, hydrochloride, hydroiodide, sulphate, bisulfate, phosphate, nitrate, hemisulfate, thiocyanate, persulfate, phosphoric and sulfonic acids.

Salts which are not pharmaceutically acceptable may still be valuable as intermediates. Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002). The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application of adaptation of known methods (e.g. asymmetric synthesis).

In one aspect the compounds of the stereochemistry of the carbon adjacent to the NH group and substituted by cyano has the S stereochemistry.

In one aspect the invention relates to a compound of the formula (I) wherein:

y represents 0, 1 or 2;

m and n are independently 0, 1, 2 or 3 (such that the sum of m and n is equal to 1, 2 or 3);

$R^1$ is $C_{1-3}$alkyl optionally substituted with one or more substituents selected from halogen, hydroxy or $C_{1-3}$alkoxy;

$R^2$ is selected from hydrogen, halogen, CN, $CF_3$, $C_{1-3}$alkyl or $C_{1-3}$alkoxy;

Q represents phenyl or a 5- to 10-membered heteroaryl ring system which is optionally substituted by at least one ring heteroatom selected from nitrogen, oxygen and sulphur, the phenyl or heteroaryl ring system being optionally substituted by at least one substituent selected from halogen, carboxyl, hydroxyl, oxo, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy, $C_{1-6}$alkylcarbonyl, $C_{1-6}$alkylcarbonyloxy, $C_{1-6}$alkoxycarbonyl, $-NR^{53}R^{54}$, $-C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl;

$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;

v is 0, 1 or 2;

$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

each $R^{57}$, $R^{58}$, $R^{61}$, $R^{62}R^{63}$ and $R^{64}$ independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring;

or a pharmaceutically-acceptable salt thereof.

In one aspect of the invention, m is 1.

In one aspect of the invention n is 1.

In one aspect of the invention y is 0.

In one aspect $R^2$ is hydrogen.

In one aspect Q is optionally substituted by 1, 2 or 3 substituents.

In another aspect Q is substituted by 1 or 2 substituents.

In another aspect Q is substituted by 1 substituent.

In one aspect of the invention, Q is phenyl or a 6 membered heteroaryl ring.

In one aspect of the invention, when Q is phenyl or a 6-membered heteroaryl ring, then it is substituted in the 4 position.

In one aspect of the invention, when Q is phenyl or a 6-membered heteroaryl ring, then it is substituted in the 3 and 4 positions.

In one aspect of the invention, when Q is phenyl or a 6-membered heteroaryl ring, then it is only substituted in the 4 position.

In one aspect Q is phenyl or pyridyl.

In one aspect X, in formula A, is CH.

In another aspect X, in formula A, is N.

In one aspect of the invention, the ring system of formula A is selected from:

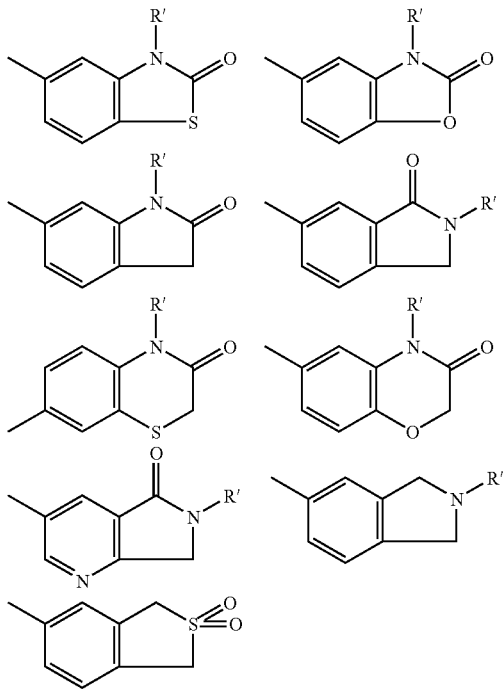

wherein R' is selected from hydrogen and $C_{1-6}$alkyl optionally substituted by $C_{1-4}$alkyoxy and the ring system being optionally further substituted on a ring as hereinabove defined. In another aspect, the ring system A has not further substituents.

In one aspect R' is hydrogen, methyl, ethyl, 2-methoxyethyl or 3-methoxypropyl.

In one aspect of the invention Q is optionally substituted by I to 3 substituents independently selected from halogen, carboxyl, hydroxyl, oxo, nitro, cyano, mercapto, $C_{1-6}$alkyl group (optionally substituted by hydroxyl, $C_{2-6}$alkoxy, $NR^{65}R^{66}$, phenyl or morpholinyl), $C_{3-6}$cycloalkyl, $C_{2-6}$alkenyl, trifluoromethyl, $C_{2-6}$alkoxy, $C_{1-6}$alkylcarbonyl, $C_{1-6}$alkylcarbonyloxy, $C_{1-6}$alkoxycarbonyl, $-NR^{53}R^{54}$, $-C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl wherein the v and R values are as hereinabove defined.

In one aspect of the invention, when Q is phenyl or heteroaryl, it is optionally substituted by 1 to 3 substituents independently selected from halogen, carboxyl, hydroxyl, oxo, nitro, cyano, mercapto, $C_{1-6}$alkyl group (substituted by hydroxyl, $C_{2-6}$alkoxy, $NR^{65}R^{66}$, phenyl or morpholinyl), $C_{3-6}$cycloalkyl, $C_{2-6}$alkenyl, trifluoromethyl, $C_{2-6}$alkoxy, $C_{1-6}$alkylcarbonyl, $C_{1-6}$alkylcarbonyloxy, $C_{1-6}$alkoxycarbonyl, $-NR^{53}R^{54}$, $-C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64})^{64}$, benzyloxy and $C_{1-6}$alkylpiperazinyl wherein the v and R values are as hereinabove defined.

In another aspect of the invention Q is substituted by 1 or 2 substituents independently selected from halogen, carboxyl, cyano, $C_{3-6}$cycloalkyl, trifluoromethyl, $-C(O)NR^{55}R^{56}$, $SO_2NR^{59}R^{60}$, $S(O)_2R^{63}$, $OS(O_2)R^{64}$, wherein the R values are as hereinabove defined.

In one aspect, when Q is of the formula A, then ring B is optionally substituted on a ring carbon by 1 oxo group.

In one aspect, when Q is of the formula A, then ring B is substituted on a ring carbon by 1 oxo group.

In one aspect, when Q is of the formula A, then ring B is optionally substituted on a ring nitrogen by $C_{1-6}$alkyl optionally substituted by $C_{1-4}$alkyoxy.

In one aspect, when Q is of the formula A, then ring B is optionally substituted on a ring nitrogen by $C_{1-4}$alkyl optionally substituted by $C_{1-2}$alkyoxy.

A class of compounds is of the formula (I'):

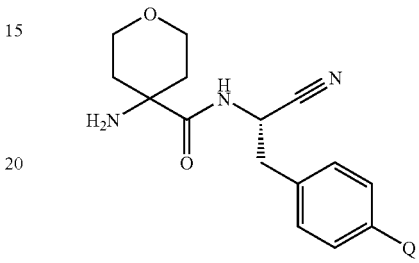

wherein Q is as hereinabove defined.

A further class of compounds is of the formula (I') wherein Q is a phenyl or pyridyl ring substituted in the 4-position and optionally substituted in the 3-position, these substituents independently selected from halogen, carboxyl, hydroxyl, oxo, nitro, cyano, mercapto, $C_{1-6}$alkyl group (substituted by hydroxyl, $C_{2-6}$alkoxy, $NR^{65}R^{66}$, phenyl or morpholinyl), $C_{3-6}$cycloalkyl, $C_{2-6}$alkenyl, trifluoromethyl, $C_{2-6}$alkoxy, $C_{1-6}$alkylcarbonyl, $C_{1-6}$alkylcarbonyloxy, $C_{1-6}$alkoxycarbonyl, $-NR^{53}R^{54}$, $-C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl wherein the v and R values are as hereinabove defined.

Yet a further class of compounds is of the formula (I') wherein Q is a phenyl or pyridyl ring substituted in the 4-position and optionally substituted in the 3-position by a substituents independently selected from cyano, halogen, $C_{1-4}$alkylsulfonyl and $C_{1-4}$alkanesulfonate.

Yet a further class of compounds is of the formula (I') wherein Q is of the formula A as hereinabove defined.

Further values of $R^1$, $R^2$, y, m, n and Q are as follows. Such values may be used where appropriate with any of the definitions, claims or embodiments defined hereinbefore or hereinafter:

y represents 0, 1 or 2.
y represents 0.
y represents 1.
y represents 0 or 1.
m and n are independently 0, 1, 2 or 3 (such that the sum of m and n is equal to 1, 2 or 3).
m and n are independently 1.
m and n are independently 0 or 1.
m and n are independently 1 or 2.
$R^1$ is $C_{1-3}$alkyl optionally substituted with one or more substituents selected from halogen, hydroxy or $C_{1-3}$alkoxy.
$R^1$ is $C_{1-3}$alkyl optionally substituted with one or more substituents selected from halogen or hydroxy.
$R^1$ is $C_{1-3}$alkyl optionally substituted with one or more substituents selected from halogen.
$R^1$ is $C_{1-3}$alkyl optionally substituted with one or more substituents selected from alkoxy.

$R^1$ is $C_{1-3}$alkyl optionally substituted with one or more substituents selected from $C_{1-3}$alkoxy.

$R^2$ is selected from hydrogen, halogen, CN, $CF_3$, $C_{1-3}$alkyl or $C_{1-3}$alkoxy;

$R^2$ is hydrogen.

Q represents phenyl or a 5- to 10-membered heteroaryl ring system which is optionally substituted by at least one ring heteroatom selected from nitrogen, oxygen and sulphur, the phenyl or heteroaryl ring system being optionally substituted by at least one substituent selected from halogen, carboxyl, hydroxyl, oxo, nitro, cyano, mercapto, $C_{1-6}$alkyl group (itself $C_{3-6}$cycloalkyl, $C_{2-6}$alkenyl, trifluoromethyl, $C_{1-6}$alkoxy, $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, benzyloxy and $C_{1-6}$alkylpiperazinyl;

$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;

v is 0, 1 or 2;

$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

each $R^{57}$, $R^{58}$, $R^{61}$, $R^{62}$, $R^{63}$, and $R^{64}$ independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring.

Q represents phenyl optionally substituted by at least one substituent selected from halogen, carboxyl, hydroxyl, oxo, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy, $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, benzyloxy and $C_{1-6}$alkylpiperazinyl;

$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;

v is 0, 1 or 2;

$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

each $R^{57}$, $R^{58}$, $R^{61}$, $R^{62}$, $R^{63}$, and $R^{64}$ independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring;

Q represents a 5- to 10-membered heteroaryl ring system which is optionally substituted by at least one ring heteroatom selected from nitrogen, oxygen and sulphur, the heteroaryl ring system being optionally substituted by at least one substituent selected from halogen, carboxyl, hydroxyl, oxo, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy, $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$ and benzyloxy and $C_{1-6}$alkylpiperazinyl; $R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;

v is 0, 1 or 2;

$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

each $R^{57}$, $R^{58}$, $R^{61}$, $R^{62}$, $R^{63}$ and $R^{64}$ independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring.

Q represents phenyl optionally substituted by at least one substituent selected from halogen, carboxyl, hydroxyl, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy, $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, benzyloxy and $C_{1-6}$alkylpiperazinyl;

$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;

v is 0, 1 or 2;

$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

each $R^{57}$, $R^{58}$, $R^{61}$, $R^{62}$, $R^{63}$ and $R^{64}$ independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring; independently represents a hydrogen atom or a $C_{1-6}$alkyl or $C_{3-6}$cycloalkyl group;

$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring;

Q represents phenyl optionally substituted by at least one substituent selected from halogen, cyano, trifluoromethyl, $SO_2NR^{59}R^{60}$, $S(O)_vR^{63}$, $OS(O_2)R^{64}$ v is 0, 1 or 2;

$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;

$R^{63}$ and $R^{64}$ independently represent $C_{1-6}$alkyl.

Examples of compounds of the invention include but are not limited to:

(S)-4-Amino-N-(1-cyano-2-(4'-(trifluoromethyl)biphenyl-4-yl)ethyl)tetrahydro-2H-pyran-4-carboxamide;

(S)-4-Amino-N-(1-cyano-2-(4'-(ethylsulfonyl)biphenyl-4-yl)ethyl)tetrahydro-2H-pyran-4-carboxamide;

(S)-4-Amino-N-(1-cyano-2-(4'-cyanobiphenyl-4-yl)ethyl)tetrahydro-2H-pyran-4-carboxamide;

(S)-4-Amino-N-(1-cyano-2-(4'-fluorobiphenyl-4-yl)ethyl)tetrahydro-2H-pyran-4-carboxamide;

(S)-4-Amino-N-(1-cyano-2-(4'-(isopropylsulfonyl)biphenyl-4-yl)ethyl)tetrahydro-2H-pyran-4-carboxamide;

(S)-4'-(2-(4-Aminotetrahydro-2H-pyran-4-carboxamido)-2-cyanoethyl)biphenyl-4-yl methanesulfonate;

(S)-4-Amino-N-(2-(4'-(azetidin-1-ylsulfonyl)biphenyl-4-yl)-1-cyanoethyl)tetrahydro-2H-pyran-4-carboxamide;

(S)-4-Amino-N-(1-cyano-2-(3'-cyanobiphenyl-4-yl)ethyl)tetrahydro-2H-pyran-4-carboxamide;

(S)-4-Amino-N-(1-cyano-2-(4-(3-(2-methoxyethyl)-2-oxo-2,3-dihydrobenzo[d]thiazol-5-yl)phenyl)ethyl)tetrahydro-2H-pyran-4-carboxamide;

(S)-4-Amino-N-(1-cyano-2-(4-(4-methyl-3-oxo-3,4-dihydro-2H-benzo[b][1,4]oxazin-6-yl)phenyl)ethyl)tetrahydro-2H-pyran-4-carboxamide;

(S)-4-Amino-N-(1-cyano-2-(4-(3-(3-methoxypropyl)-2-oxo-2,3-dihydrobenzo[d]oxazol-5-yl)phenyl)ethyl)tetrahydro-2H-pyran-4-carboxamide;

(S)-4'-(2-(4-Aminotetrahydro-2H-pyran-4-carboxamido)-2-cyanoethyl)biphenyl-3-yl methanesulfonate;

(S)-4-Amino-N-(1-cyano-2-(3',4'-difluorobiphenyl-4-yl)ethyl)tetrahydro-2H-pyran-4-carboxamide;

(S)-4-Amino-N-(1-cyano-2-(4-(1-oxoisoindolin-5-yl)phenyl)ethyl)tetrahydro-2H-pyran-4-carboxamide;

(S)-4-Amino-N-{cyano-2-[4-(2-methyl-1,1-dioxido-2,3-dihydro-1,2-benzisothiazol-5-yl)phenyl]ethyl}tetrahydro-2H-pyran-4-carboxamide;

(S)-4-amino-N-(1-cyano-2-(4-(3-methyl-2-oxo-2,3-dihydrobenzo[d]oxazol-5-yl)phenyl)ethyl)tetrahydro-2H-pyran-4-carboxamide;

(S)-4-Amino-N-(1-cyano-2-(3'-cyano-4'-methylbiphenyl-4-yl)ethyl)tetrahydro-2H-pyran-4-carboxamide;

(S)-4-Amino-N-(1-cyano-2-(4'-cyano-3'-methylbiphenyl-4-yl)ethyl)tetrahydro-2H-pyran-4-carboxamide;

(S)-4-Amino-N-(1-cyano-2-(4'-methoxybiphenyl-4-yl)ethyl)tetrahydro-2H-pyran-4-carboxamide;

(S)-4-Amino-N-(1-cyano-2-(4-(1-methyl-2-oxoindolin-6-yl)phenyl)ethyl)tetrahydro-2H-pyran-4-carboxamide;

(S)-4-Amino-N-(1-cyano-2-(3'-cyano-4'-fluorobiphenyl-4-yl)ethyl)tetrahydro-2H-pyran-4-carboxamide;

(S)-4-Amino-N-(1-cyano-2-(3'-(methylsulfonyl)biphenyl-4-yl)ethyl)tetrahydro-2H-pyran-4-carboxamide;

(S)-4-Amino-N-(1-cyano-2-(4-(3-(2-methoxyethyl)-2-oxo-2,3-dihydrobenzo[d]oxazol-5-yl)phenyl)ethyl)tetrahydro-2H-pyran-4-carboxamide;

(S)-4-Amino-N-(2-(4'-carbamoyl-3'-fluorobiphenyl-4-yl)-1-cyanoethyl)tetrahydro-2H-pyran-4-carboxamide;

(S)-4-Amino-N-(1-cyano-2-(4-(2-methoxypyridin-4-yl)phenyl)ethyl)tetrahydro-2H-pyran-4-carboxamide;

(S)-4-Amino-N-(1-cyano-2-(4'-(morpholinosulfonyl)biphenyl-4-yl)ethyl)tetrahydro-2H-pyran-4-carboxamide;

(S)-4-Amino-N-(1-cyano-2-(4-(4-methyl-3-oxo-3,4-dihydro-2H-benzo[b][1,4]thiazin-7-yl)phenyl)ethyl)tetrahydro-2H-pyran-4-carboxamide;

(S)-4-Amino-N-(1-cyano-2-(4'-(4-methylpiperazin-1-ylsulfonyl)biphenyl-4-yl)ethyl)tetrahydro-2H-pyran-4-carboxamide;

(S)-4-Amino-N-(1-cyano-2-(4-(2-methyl-3-oxoisoindolin-5-yl)phenyl)ethyl)tetrahydro-2H-pyran-4-carboxamide;

(S)-4-Amino-N-(1-cyano-2-(4-(2-methyl-1-oxoisoindolin-5-yl)phenyl)ethyl)tetrahydro-2H-pyran-4-carboxamide;

(S)-4-Amino-N-(1-cyano-2-(4-(6-methyl-7-oxo-6,7-dihydro-5H-pyrrolo[3,4-b]pyridin-3-yl)phenyl)ethyl)tetrahydro-2H-pyran-4-carboxamide;

(S)-4-Amino-N-(1-cyano-2-(4-(2-oxo-2,3-dihydrobenzo[d]oxazol-5-yl)phenyl)ethyl)tetrahydro-2H-pyran-4-carboxamide trifluoroacetic acid salt; and 4-Amino-N-{(1S)-1-cyano-2-[4-(2,2-dioxido-1,3-dihydro-2-benzothiophen-5-yl)phenyl]ethyl}tetrahydro-2H-pyran-4-carboxamide and pharmaceutically acceptable salts of any one thereof.

It should be noted that each of the chemical compounds listed above represents a particular and independent aspect of the invention.

Compounds of the invention which have less preferable potency and/or stability are:

(S)-4-amino-N-(1-cyano-2-(3'-fluoro-4'-methoxybiphenyl-4-yl)ethyl)tetrahydro-2H-pyran-4-carboxamide;

(S)-4-amino-N-(1-cyano-2-(4'-methylbiphenyl-4-yl)ethyl)tetrahydro-2H-pyran-4-carboxamide;

(S)-4-amino-N-(1-cyano-2-(biphenyl-4-yl)ethyl)tetrahydro-2H-pyran-4-carboxamide; and (R)-4-amino-N-{cyano-2-[4-(2-methyl-1,1-dioxido-2,3-dihydro-1,2-benzisothiazol-5-yl)phenyl]ethyl}tetrahydro-2H-pyran-4-carboxamide;

and pharmaceutically acceptable salts thereof.

In another aspect the invention relates to a compound of the formula (I) as hereinabove defined excluding any 1 of the specific examples or pharmaceutically acceptable salts thereof. In yet another aspect the invention relates to a compound of the formula (I') as hereinabove defined excluding any 1 of the specific examples or pharmaceutically acceptable salts thereof.

The skilled person will recognise that the compounds of the invention may be prepared, in known manner, in a variety of ways. The routes below are merely illustrative of some of the methods that can be employed for the synthesis of compounds of formula (I).

The present invention further provides a process for the preparation of a compound of formula (I) or a pharmaceutically acceptable salt thereof as defined above which comprises reacting a compound of formula (II)

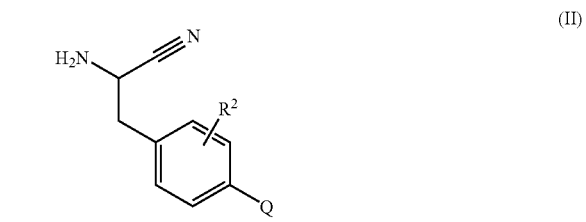

(II)

wherein R² and Q are as defined in formula (I), with a compound of formula (III)

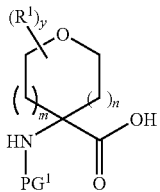
(III)

wherein PG¹ represents a protecting group (e.g. tert-butoxycarbonyl), R¹, R², m, n and y are as defined in formula (I), and optionally thereafter carrying out one or more of the following procedures:

converting a compound of formula (I) into another compound of formula (I)

removing any protecting groups forming a pharmaceutically acceptable salt.

The process of the invention is conveniently carried out in the presence of a base such as diisopropylethylamine or triethylamine and an activating agent such as a "uronium" reagent (for example, 2-(1-H-benzotriazole-1-yl)-1,1,3,3-tetramethyluronium tetrafluoroborate) or a dehydrating agent (for example, propane phosphonic acid anhydride). The reaction is conveniently carried out in an organic solvent such as N,N-dimethylformamide or tetrahydrofuran at a temperature, for example, in the range from 20° C. to 100° C., in particular at ambient temperature (25° C.).

Compounds of formula (II) may be prepared by reaction of a compound of formula (IV)

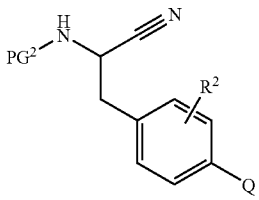
(IV)

wherein PG² represents a protecting group (e.g. tert-butoxycarbonyl) and R², and Q are as defined in formula (II), with a suitable reagent to remove the protecting group PG². An example of a suitable reagent is formic acid.

Compounds of formula (IV) may be prepared by reacting a compound of formula (V)

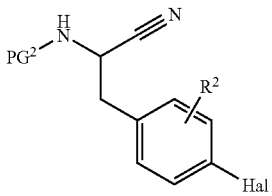
(V)

wherein PG₂ and R² are as defined in formula (IV) and Hal represents a halogen (e.g. I or Br), with a compound of formula (VI) or an ester thereof

(VI)

in the presence of a catalyst such as bis[bis(1,2-diphenylphosphino)ethane]palladium(0) or 1,1 bis(di-tert-butylphosphino)ferrocene palladium dichloride and a base such as potassium carbonate or sodium carbonate. The reaction is conveniently carried out in a solvent such as dioxane/water mixture or acetonitrile/water mixture at a temperature, for example, in the range from 20° C. to 100° C., particularly at 75° C.

Compounds of formula (V) may be prepared from a compound of formula (VII)

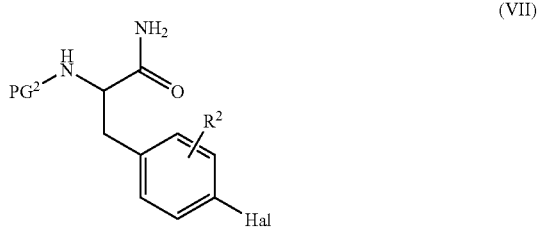
(VII)

in which PG₂ and R² are as defined in formula (V) and Hal represents a halogen (e.g. I or Br), using standard literature procedures for the dehydration of an amide, for example with (methoxycarbonylsulfamoyl)tri-ethyl ammonium hydroxide, which can be prepared in situ with triethylamine and methyl chlorosulfonylcarbamate or a reagent such as propylphosphonic anhydride (T3P) with or without a base such as diisopropylethylamine, in a solvent such as dichloromethane or N,N-dimethylformamide at a temperature in the range from −20° C. to 100° C., for example at 0° C.

Compounds of formula (VII) may be prepared by reacting a compound of formula (VIII)

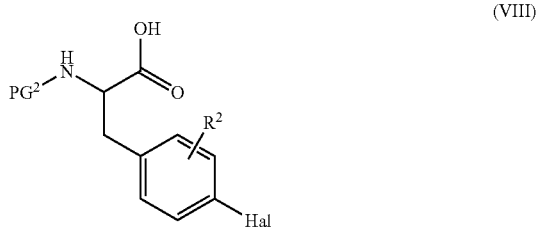
(VIII)

in which PG₂ and R² are as defined in formula (VII) and Hal represents a halogen (e.g. I or Br), with an aqueous ammonia solution, using standard literature procedures for the formation of an amide, for example, in the presence of a base such as N-ethyl-morpholine or diisopropylethylamine and an activating agent such as a "uronium" reagent (for example, 2-(1-H-benzotriazole-1-yl)-1,1,3,3-tetramethyluronium tetrafluoroborate) or propylphosphonic anhydride (T3P). The reaction is conveniently carried out in an organic solvent such as N,N-dimethylformamide, at a temperature in the range from −20° C. to 100° C., for example at 0° C.

Compounds of formula (VIII) are either commercially available, are known in the literature (e.g. from *Tetrahedron: Asymmetry*, 1998, 9, 503) or may be prepared using known techniques.

Other compounds of formula (IV) in which Q represent a heteroaryl group may be prepared by reacting a compound of formula (X)

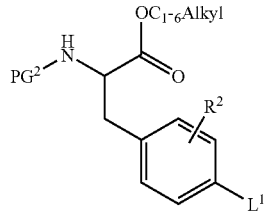
(X)

in which $PG_2$ and $R^2$ are as defined in formula (IV) and $L^1$ represents a leaving group such as halogen, with a compound of formula (VI) or formula (XI), Q-B(OR)$_2$, in which Q represents a heteroaryl group to form a compound of formula (XII)

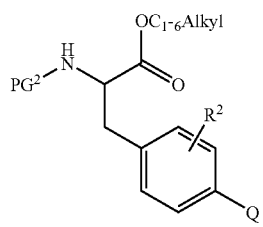
(XII)

in which $PG_2$, $R^2$ and Q are as defined above. Compounds of formula (XII) can then be converted to compounds of formula (IV) by processes known in the art, for example, as described in *Bioorg. Med. Chem. Lett.* 2002, 12, 3059 or Published US Patent Application No. 2007/0099835.

The present invention further provides a process for the preparation of a compound of formula (I) or a pharmaceutically acceptable salt thereof as defined above which comprises reacting a compound of formula (XIII)

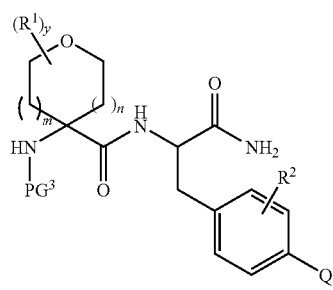
(XIII)

wherein $R^1$, $R^2$, m, n, y, and Q are as defined above and $PG^3$ represents a protecting group (e.g. tert-butoxycarbonyl), using standard literature procedures for the dehydration of an amide, for example with (methoxycarbonylsulfamoyl)triethyl ammonium hydroxide, which can be prepared in situ with triethylamine and methyl chlorosulfonylcarbamate or a reagent such as or propylphosphonic anhydride (T3P) with or without a base such as diisopropylethylamine, in a solvent such as dichloromethane or N,N-dimethylformamide at a temperature in the range from −20° C. to 100° C., for example at 0° C.

A compound of formula (XIII), may be prepared by reacting a compound of formula (XIV) wherein $R^1$, $R^2$, m, n, y, and Q are as defined above and $PG^3$ represents a protecting group (e.g. tert-butoxycarbonyl),

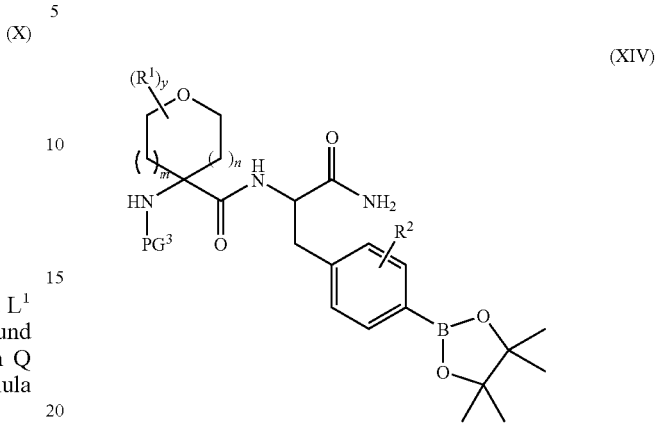
(XIV)

with a halide of formula (XV) in which Q is defined as in formula (I)

Q-Br/I    (XV)

in the presence of a catalyst such as bis[bis(1,2-diphenylphosphino)ethane]palladium(0) and a base such as potassium carbonate or sodium carbonate. The reaction is conveniently carried out in a solvent such as dioxane/water mixture or acetonitrile/water mixture at a temperature, for example, in the range from 20° C. to 100° C., particularly at 75° C.

A compound of formula (XIV) may be prepared by reacting a compound of formula (XVI) wherein $R^1$, $R^2$, m, n, y, and Q are as defined above and $PG^3$ represents a protecting group (e.g. tert-butoxycarbonyl) with 4,4,4',4',5,5,5',5'-octamethyl-2,2'-bi(1,3,2-dioxaborolane) in the presence of a suitable catalyst such as 1,1'-bis(diphenylphosphino)ferrocene-palladium(II)dichloride DCM complex and 1,1'-bis(diphenylphosphino)ferrocene or 1,1 bis(di-tert-butylphosphino) ferrocene palladium dichloride, with a suitable base such as potassium acetate, in a solvent such as dimethylsulfoxide at a temperature in the range 60° C. to 100° C., for example at 80° C.

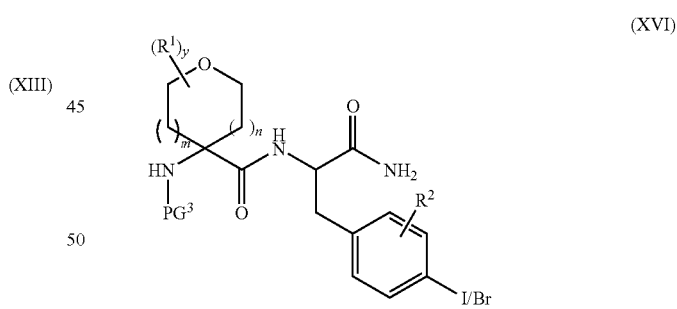
(XVI)

A compound of formula (XVI) may be prepared by reacting a compound of formula (XVII)

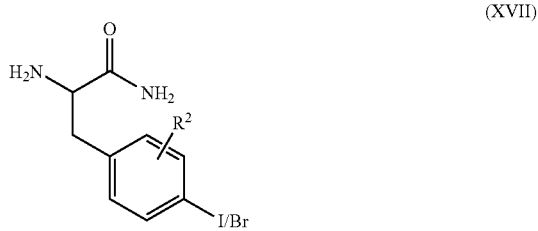
(XVII)

wherein $R^2$ is as defined above, with a compound of formula (III)

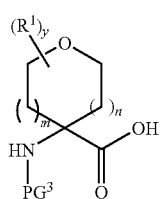

(III)

wherein $R^1$, m, n, and y are as defined above and $PG^3$ represents a protecting group (e.g. tert-butoxycarbonyl) in the presence of a base such as diisopropylethylamine or triethylamine and a dehydrating agent (for example, propane phosphonic acid anhydride). The reaction is conveniently carried out in an organic solvent such as N,N-dimethylformamide or tetrahydrofuran at a temperature, for example, in the range from 20° C. to 100° C., in particular at ambient temperature (25° C.).

Compounds of formula (XVII) may be prepared by reacting a compound of formula (XVIII)

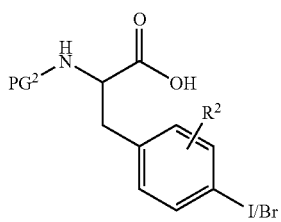

(XVIII)

in which $PG^2$ and $R^2$ are as defined in formula (VII), with an aqueous ammonia solution, using standard literature procedures for the formation of an amide, for example, in the presence of a base such as N-ethyl-morpholine or diisopropylethylamine and an activating agent such as a "uronium" reagent (for example, 2-(1-H-benzotriazole-1-yl)-1,1,3,3-tetramethyluronium tetrafluoroborate) or propylphosphonic anhydride (T3P). The reaction is conveniently carried out in an organic solvent such as N,N-dimethylformamide, at a temperature in the range from −20° C. to 100° C., for example at 0° C.

A compound of formula (XIII) may be prepared by reacting a compound of formula (XVI) wherein $R^1$, $R^2$, m, n, y, and Q are as defined above and $PG^3$ represents a protecting group (e.g. tert-butoxycarbonyl), with a compound of formula (VI) or formula (XI), Q-B(OR)$_2$, in the presence of a catalyst such as bis[bis(1,2-diphenylphosphino)ethane]palladium(0) or 1,1 bis(di-tert-butylphosphino)ferrocene palladium dichloride and a base such as potassium carbonate or sodium carbonate. The reaction is conveniently carried out in a solvent such as dioxane/water or acetonitrile/water mixture at a temperature, for example, in the range from 20° C. to 100° C., particularly at 75° C.

Compounds of formula (VIII) are either commercially available, are known in the literature (e.g. from *Tetrahedron: Asymmetry*, 1998, 9, 503) or may be prepared using known techniques.

Compounds of formulae (III), (VIII), (XV) and (XVIII) are either commercially available, are known in the literature or may be prepared using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate.

The compounds of formula (I) and pharmaceutically acceptable salts thereof may exist in solvated, for example hydrated, as well as unsolvated forms, and the present invention encompasses all such solvated forms.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are a particular aspect of the invention.

The compounds of formula (I) and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, chlamydia, candida, aspergillus, cryptococcal meningitis, pneumocystis carnii, cryptosporidiosis, histoplasmosis, toxoplasmosis, trypanosome infection and leishmaniasis.

Thus, the present invention provides a compound of formula (I) or a pharmaceutically acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

The invention also provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

In a further aspect, the present invention provides the use of a compound of formula (I) or a pharmaceutically acceptable salt thereof as hereinbefore defined in the manufacture of a medicament for use in treating COPD.

In a further aspect, the present invention provides the use of a compound of formula (I) or a pharmaceutically acceptable salt thereof as hereinbefore defined in the manufacture of a medicament for use in treating asthma.

In a further aspect, the present invention provides the use of a compound of formula (I) or a pharmaceutically acceptable salt thereof as hereinbefore defined in the manufacture of a medicament for use in treating allergic rhinitis.

In a further aspect, the present invention provides a compound of formula (I) or a pharmaceutically acceptable salt thereof as hereinbefore defined for use in treating allergic rhinitis.

In a further aspect, the present invention provides a compound of formula (I) or a pharmaceutically acceptable salt thereof as hereinbefore defined for use in treating COPD.

In a further aspect, the present invention provides a compound of formula (I) or a pharmaceutically acceptable salt thereof as hereinbefore defined for use in treating asthma.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention (that is, compounds of formula (I) and pharmaceutically acceptable salts thereof) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax II-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention and a beta-adrenoreceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$ or $NK_3$ receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; (xxvii) inhibitor of transcription factor activation such as NFkB, API, or STATS; or (xxviii) a glucocorticoid receptor agonist.

In a further aspect the present invention provides a combination (for example for the treatment of COPD, asthma or allergic rhinitis) of a compound of formula (I) or a pharmaceutically acceptable salt thereof as hereinbefore defined and one or more agents independently selected from:

a non-steroidal glucocorticoid receptor (GR-receptor) agonist;
a selective $β_2$ adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);
a phosphodiesterase inhibitor (such as a PDE4 inhibitor);
a protease inhibitor (such as a neutrophil elastase or matrix metalloprotease MMP-12 inhibitor);
a glucocorticoid;
an anticholinergic agent;
a modulator of chemokine receptor function (such as a CCR1 receptor antagonist); and
an inhibitor of kinase function (such as the kinases p38 or IKK).

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is a non-steroidal glucocorticoid receptor (GR-receptor) agonist;
a selective β2 adrenoceptor agonist;
a phosphodiesterase inhibitor;
a protease inhibitor;
a glucocorticoid;
an anticholinergic agent;
a modulator of chemokine receptor function; or
an inhibitor of kinase function;
for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is a non-steroidal glucocorticoid receptor (GR-receptor) agonist;
a selective $β_2$ adrenoceptor agonist;
a phosphodiesterase inhibitor;
a protease inhibitor;
a glucocorticoid;
an anticholinergic agent;
a modulator of chemokine receptor function; or
an inhibitor of kinase function;
and instructions for the simultaneous, sequential or separate administration of the preparations to a patient in need thereof.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin avβ3 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated by the following non-limiting Examples in which, unless stated otherwise:
(i) when given, $^1$H NMR spectra were recorded on Bruker Avance 600 (600 MHz), a Bruker DRX 500 (500 MHz) or a Varian Unitylnova 500 MHz, 400 MHz or 300 MHz instrument. Either the central peaks of chloroform-d (CDCl$_3$; $\delta_H$ 7.27 ppm), dimethylsulfoxide-d$_6$ (d$_6$-DMSO; $\delta_H$ 2.50 ppm) or methanol-d$_4$ (CD$_3$OD; $\delta_H$ 3.31 ppm), or an internal standard of tetramethylsilane (TMS; $\delta_H$ 0.00 ppm) were used as references;
(ii) Mass spectra were recorded on an Agilent MSD (+ve and −ve APCI and/or electrospray (e.g. in multimode)) following analytical HPLC. Where values for m/z are given, generally only ions which indicate the parent mass are reported, and the mass ions quoted are the positive or negative mass ions: [M]$^+$, [M+H]$^+$, [M−H]$^−$ or [M+2H−BOC]$^+$;
(iii) the title and sub-title compounds of the examples and preparations were named using the IUPAC name program Struct=Name 9.0.7 from CambridgeSoft Corporation.
(iv) unless stated otherwise, reverse phase HPLC was conducted using a SunFire® reverse phase silica column, available from Waters Corp.;
(v) Unless stated otherwise, starting materials were commercially available. All solvents and commercial reagents were of laboratory grade and were used as received. All operations were carried out at ambient temperature, i.e. in the range 17 to 28° C. and, where appropriate, under an atmosphere of an inert gas such as nitrogen;
(vi) Analytical HPLC was carried out using either a Waters XBridge™ C8 3.5 nm column eluting with a gradient of acetonitrile in either 0.1% aqueous trifluoroacetic acid, 0.1% aqueous formic acid, 0.1% aqueous ammonium acetate or 0.1% aqueous ammonia; a Waters XBridge™ C18 3.5 μm column with a gradient of acetonitrile in 0.1% aqueous ammonia; a Waters Symmetry™ C18 3.5 μm column with a gradient of acetonitrile in 0.1% aqueous trifluoroacetic acid; a Waters Sunfire™ C8 3.5 μm column with a gradient of acetonitrile in 0.1% aqueous trifluoroacetic acid; or a Phenomenex Gemini™ C18 3 μm column with a gradient of acetonitrile in 0.1% aqueous trifluoroacetic acid. UV spectra of the eluted peaks were measured using a diode array on an Agilent 1100® system, or equivalent;
(vii) the following abbreviations are used:

| | |
|---|---|
| AIBN | 2,2'-Azobisisobutyronitrile |
| Burgess reagent | Methyl (carboxysulfamoyl)triethyl ammonium hydroxide inner salt |
| CbzCl | Benzyloxycarbonylchloride |
| d | Day(s) |
| DCE | 1,2-Dichloroethane |
| DCM | Dichloromethane |
| DMF | N,N-Dimethylformamide |
| DMSO | Dimethyl sulfoxide |
| g | Gram(s) |
| h | Hour(s) |
| HATU | 2-(1H-7-Azabenzotriazol-1-yl)-1,1,3,3-tetramethyluronium hexafluorophosphate |
| HM-N | Argonaut Isolute ® diatomaceous earth cartridge |
| HPLC | High performance liquid chromatography |
| Hunig's Base | Diisopropylethylamine (DIPEA) |
| LCMS | Liquid chromatography-mass spectroscopy |
| min | Minute(s) |
| mL | Milliliter(s) |
| n-BuLi | n-Butyllithium |
| NMP | 1-Methylpyrrolidin-2-one |
| RPHPLC | Reverse phase high performance liquid chromatography |
| RT | Room temperature |
| SCX | Strong cation exchange resin |
| TBAF | Tetrabutylammonium fluoride |
| TBTU | 2-(1H-Benzo[d][1,2,3]triazol-1-yl)-1,1,3,3-tetramethylisouronium tetrafluoroborate |
| TEA | Triethylamine |
| TFA | Trifluoroacetic acid |
| THF | tetrahydrofuran |

EXAMPLE 1

(S)-4-Amino-N-(1-cyano-2-(4'-(trifluoromethyl)biphenyl-4-yl)ethyl)tetrahydro-2H-pyran-4-carboxamide

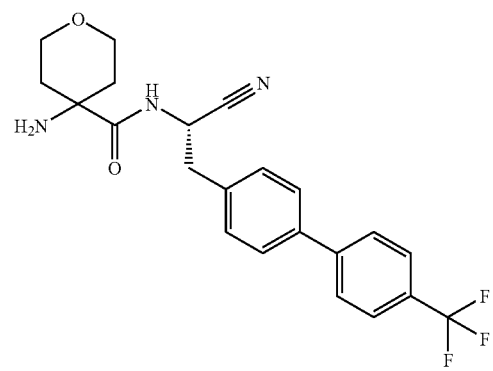

(i) (S)-tert-Butyl 1-amino-3-(4-iodophenyl)-1-oxo-propan-2-ylcarbamate

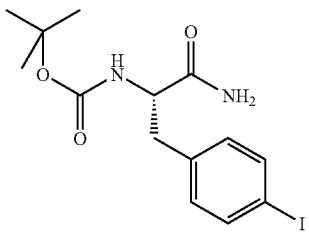

(S)-2-(tert-Butoxycarbonylamino)-3-(4-iodophenyl)propanoic acid (35.1 g) was dissolved in DMF (200 mL) and to the resulting solution was added N-ethylmorpholine (17.0 mL) followed by TBTU (28.8 g). The mixture was stirred at room temperature for 0.5 h and then cooled to 0° C. 0.88 Ammonia (11.1 mL) was added and the mixture was allowed to warm to room temperature. The mixture was allowed to stir at room temperature for 16 h and was then poured into water and the resulting precipitate removed by filtration. The solid was dried in vacuo to give the sub-titled compound (34.2 g).

m/e (APCI+) 290 [M+2H−BOC]+

(ii) (S)-2-Amino-3-(4-iodophenyl)propanamide

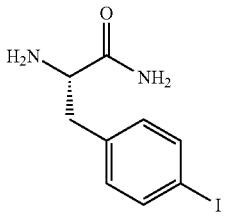

(S)-tert-Butyl 1-amino-3-(4-iodophenyl)-1-oxopropan-2-ylcarbamate (Example 1, step (i), 2.41 g) was stirred in dichloromethane (125 mL) and to the suspension was added trifluoroacetic acid (8 mL). The mixture was stirred for 2 h and then concentrated to ~12 mL in vacuo. The residue was stirred for 2 days, dissolved in ethyl acetate/dichloromethane and washed with water containing an excess of sodium bicarbonate. The organic layer was dried and evaporated to the sub-titled compound (1.52 g).

$^1$H NMR (399.824 MHz, CDCl$_3$) δ 7.61 (d, 2H), 7.26 (s, 1H), 7.03 (d, 2H), 6.40 (s, 1H), 3.55 (s, 1H), 3.09 (dd, 1H), 2.71 (dd, 1H), 1.81 (s, 2H).

m/e (APCI+) 291 [M+H]+

(iii) (S)-tert-Butyl 4-(1-amino-3-(4-iodophenyl)-1-oxopropan-2-ylcarbamoyl)tetrahydro-2H-pyran-4-ylcarbamate

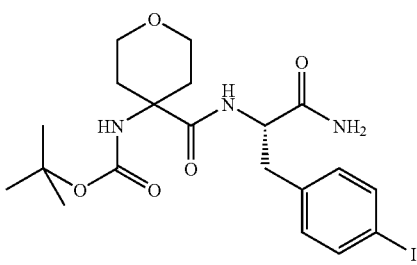

4-(tert-Butoxycarbonylamino)tetrahydro-2H-pyran-4-carboxylic acid (0.801 g), (S)-2-amino-3-(4-iodophenyl)propanamide (Example 1, step (ii), 0.947 g) and N-ethyl-N-isopropylpropan-2-amine (1.422 mL) were dissolved in DMF (10 mL) and to the solution was added TBTU (1.573 g). The reaction mixture was stirred, at room temperature, for 2 days. The reaction mixture was evaporated to dryness dissolved in dichloromethane (20 mL) and evaporated onto silica. The silica was put on the top of a silica column and eluted with 20% ethyl acetate in isohexane then 50% ethyl acetate in isohexane then 100% ethyl acetate followed by 10% then 20% methanol in ethyl acetate to afford the sub-titled compound (2.00 g).

m/e (APCI+) 418.0 [M+2H−BOC]+

(iv) (S)-tert-Butyl 4-(1-amino-1-oxo-3-(4'-(trifluoromethyl)biphenyl-4-yl)propan-2-ylcarbamoyl)tetrahydro-2H-pyran-4-ylcarbamate

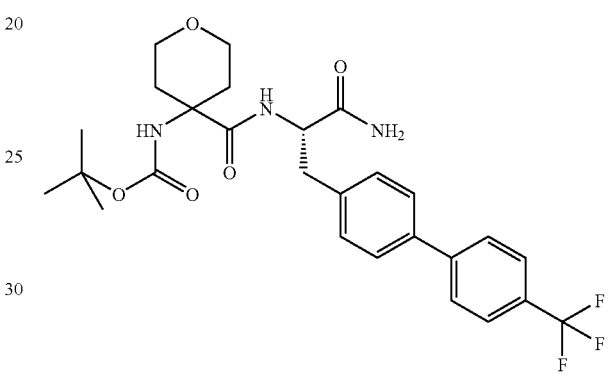

and (S)-tert-Butyl 4-(1-amino-3-(4'-(ethylsulfonyl)biphenyl-4-yl)-1-oxopropan-2-ylcarbamoyl)tetrahydro-2H-pyran-4-ylcarbamate

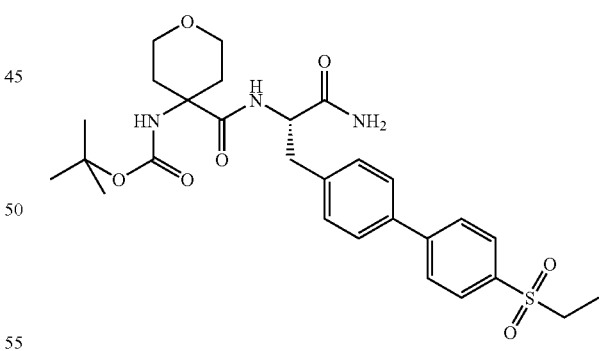

(S)-tert-Butyl 4-(1-amino-3-(4-iodophenyl)-1-oxopropan-2-ylcarbamoyl)tetrahydro-2H-pyran-4-ylcarbamate (Example 1, step (iii), 2.0 g) in acetonitrile (5 mL) under nitrogen was treated with 4-(trifluoromethyl)phenylboronic acid (0.367 g) and 4-(ethylsulfonyl)phenylboronic acid (0.414 g) followed by aqueous potassium carbonate (3.87 mL) and 1,1 bis(di-tert-butylphosphino)ferrocene palladium dichloride (25 mg). The mixture was stirred at 75° C. for 18 h. The reaction mixture was evaporated, dissolved in dichloromethane, evaporated onto silica and purified on a silica column eluting with 50% ethyl acetate in isohexane and then 100% ethyl acetate to afford (S)-tert-butyl 4-(1-amino-1-oxo-3-(4'-(trifluoromethyl)biphenyl-4-yl)propan-2-ylcarbamoyl)tetrahydro-2H-pyran-4-ylcarbamate and (S)-tert-butyl 4-(1-amino-3-(4'-(ethylsulfonyl)biphenyl-4-yl)-1-oxopropan-2-ylcarbamoyl)tetrahydro-2H-pyran-4-ylcarbamate as a mixture (1.7 g).

Data for (S)-tert-butyl 4-(1-amino-1-oxo-3-(4'-(trifluoromethyl)biphenyl-4-yl)propan-2-ylcarbamoyl)tetrahydro-2H-pyran-4-ylcarbamate m/e (APCI+) 436.0 [M+2H−BOC]+

Data for (S)-tert-butyl 4-(1-amino-3-(4'-(ethylsulfonyl)biphenyl-4-yl)-1-oxopropan-2-ylcarbamoyl)tetrahydro-2H-pyran-4-ylcarbamate m/e (APCI+) 460.0 [M+2H−BOC]+

(v(i)) (S)-tert-Butyl 4-(1-cyano-2-(4'-(trifluoromethyl)biphenyl-4-yl)ethylcarbamoyl)tetrahydro-2H-pyran-4-ylcarbamate

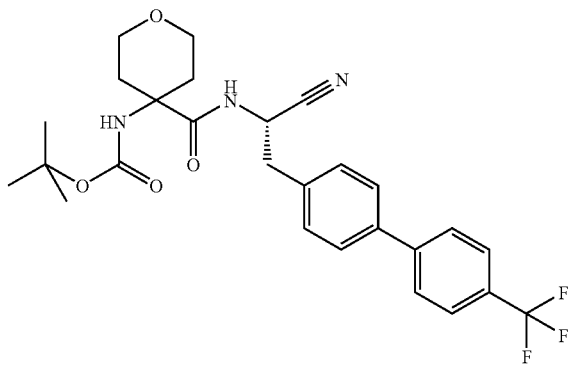

and (v(ii)) (S)-tert-Butyl 4-(1-cyano-2-(4'-(ethylsulfonyl)biphenyl-4-yl)ethylcarbamoyl)tetrahydro-2H-pyran-4-ylcarbamate

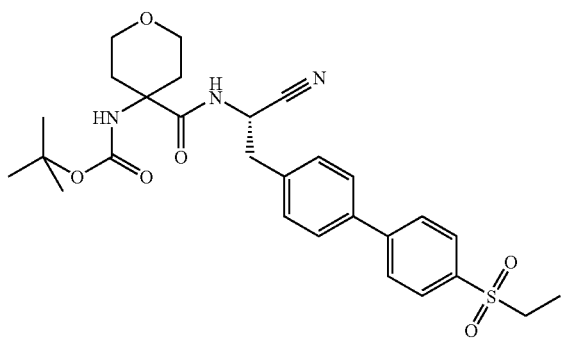

The mixture of (S)-tert-butyl 4-(1-amino-1-oxo-3-(4'-(trifluoromethyl)biphenyl-4-yl)propan-2-ylcarbamoyl)tetrahydro-2H-pyran-4-ylcarbamate and (S)-tert-butyl 4-(1-amino-3-(4'-(ethylsulfonyl)biphenyl-4-yl)-1-oxopropan-2-ylcarbamoyl)tetrahydro-2H-pyran-4-ylcarbamate (Example 1, step (iv), 1.7 g) in dichloromethane (15 mL) was treated with Burgess' reagent (1.19 g) and the mixture was stirred at room temperature for 72 h. The reaction was evaporated onto silica and purified on a silica column eluting with 20% ethyl acetate in isohexane, then 50% ethyl acetate in isohexane and finally 100% ethyl acetate to afford after evaporation of the relevant fractions (S)-tert-butyl 4-(1-cyano-2-(4'-(trifluoromethyl)biphenyl-4-yl)ethylcarbamoyl)tetrahydro-2H-pyran-4-ylcarbamate (650 mg) and (S)-tert-butyl 4-(1-cyano-2-(4'-(ethylsulfonyl)biphenyl-4-yl)ethylcarbamoyl)tetrahydro-2H-pyran-4-ylcarbamate (920 mg).

Data for (S)-tert-butyl 4-(1-cyano-2-(4'-(trifluoromethyl)biphenyl-4-yl)ethylcarbamoyl)tetrahydro-2H-pyran-4-ylcarbamate $^1$H NMR (399.824 MHz, CDCl$_3$) δ 7.70 (d, 2H), 7.67 (d, 2H), 7.59 (d, 2H), 7.40 (d, 2H), 5.14 (dd, 1H), 4.78 (s, 1H), 3.84-3.76 (m, 1H), 3.74-3.56 (m, 2H), 3.44 (d, 1H), 3.40 (d, 1H), 3.21-3.09 (m, 2H), 2.27-1.88 (m, 2H), 1.85-1.77 (m, 1H), 1.67 (s, 1H), 1.44 (s, 7H), 1.43 (s, 2H).

m/e (APCI+) 418.0 [M+2H−BOC]+

$^{19}$F NMR (376.169 MHz, CDCl$_3$) δ −62.97 (s, 3F).

Data for (S)-tert-butyl 4-(1-cyano-2-(4'-(ethylsulfonyl)biphenyl-4-yl)ethylcarbamoyl)tetrahydro-2H-pyran-4-ylcarbamate $^1$H NMR (399.824 MHz, CDCl$_3$) δ 7.96 (d, 2H), 7.75 (d, 2H), 7.59 (d, 2H), 7.42 (d, 2H), 5.21-4.99 (m, 1H), 5.14 (dd, 1H), 3.86-3.76 (m, 1H), 3.74-3.67 (m, 2H), 3.67-3.57 (m, 2H), 3.24 (dd, 2H), 3.17 (dd, 2H), 2.27-1.76 (m, 4H), 1.44 (s, 9H), 1.37 (t, 3H).

m/e (APCI+) 442.0 [M+2H−BOC]+

(S)-4-Amino-N-(1-cyano-2-(4'-(trifluoromethyl)biphenyl-4-yl)ethyl)tetrahydro-2H-pyran-4-carboxamide To (S)-tert-butyl 4-(1-cyano-2-(4'-(trifluoromethyl)biphenyl-4-yl)ethylcarbamoyl)tetrahydro-2H-pyran-4-ylcarbamate (Example 1, step (v(i)), 650 mg) was added formic acid (3 mL) and the mixture heated to 50° C. for 10 min. The mixture was evaporated to dryness, dissolved in methanol (6 mL) and purified on reverse phase HPLC eluting with 25 to 95% methanol in 0.1% TFA on a Waters SunFire column. The material was converted to free base by evaporating the relevant fractions, dissolving in dichloromethane (20 mL) and shaking with saturated sodium bicarbonate solution (20 mL). The dichloromethane was dried and to evaporated to afford the titled compound as a solid (200 mg).

$^1$H NMR (399.824 MHz, CDCl$_3$) δ 8.24 (d, 1H), 7.70 (d, 2H), 7.67 (d, 2H), 7.59 (dt, 2H), 7.38 (d, 2H), 5.14 (dt, 1H), 3.92 (dt, 1H), 3.87 (dt, 1H), 3.65-3.55 (m, 2H), 3.16 (d, 2H), 2.34-2.26 (m, 1H), 2.23-2.14 (m, 1H), 1.53 (s, 2H), 1.29 (dq, 1H), 1.19 (dq, 1H).

m/e (MultiMode+) 418 [M+H]+

$^{19}$F NMR (376.169 MHz, CDCl$_3$) δ −62.99 (s, 3F).

EXAMPLE 2

(S)-4-Amino-N-(1-cyano-2-(4'-(ethylsulfonyl)biphenyl-4-yl)ethyl)tetrahydro-2H-pyran-4-carboxamide

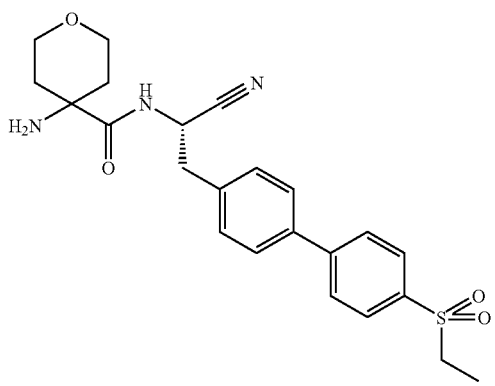

To (S)-tert-butyl 4-(1-cyano-2-(4'-(ethylsulfonyl)biphenyl-4-yl)ethylcarbamoyl)tetrahydro-2H-pyran-4-ylcarbamate (Example 1, step (v(ii)), 920 mg) was added formic acid (3 mL) and the mixture heated to 50° C. for 30 min. The mixture was evaporated to dryness, dissolved in methanol (9 mL) and purified on reverse phase HPLC eluting with 25 to 95% methanol in 0.1% TFA on a Waters SunFire column. The material was converted to free base by evaporating the relevant fractions, dissolving in dichloromethane (20 mL) and shaking with saturated sodium bicarbonate solution (20 mL). The dichloromethane was dried and evaporated to afford the titled compound as a solid (397 mg).

$^1$H NMR (399.824 MHz, CDCl$_3$) δ 8.26 (d, 1H), 7.97 (dt, 2H), 7.76 (dt, 2H), 7.61 (dt, 2H), 7.40 (d, 2H), 5.14 (dt, 1H), 3.92 (dt, 1H), 3.87 (dt, 1H), 3.65-3.56 (m, 2H), 3.16 (d, 2H), 3.16 (q, 2H), 2.35-2.26 (m, 1H), 2.24-2.15 (m, 1H), 1.54 (s, 2H), 1.33-1.26 (m, 1H), 1.32 (t, 3H), 1.20 (dq, 1H).

m/e (MultiMode+) 442 [M+H]$^+$

EXAMPLE 3

(S)-4-Amino-N-(1-cyano-2-(4'-cyanobiphenyl-4-yl)ethyl)tetrahydro-2H-pyran-4-carboxamide

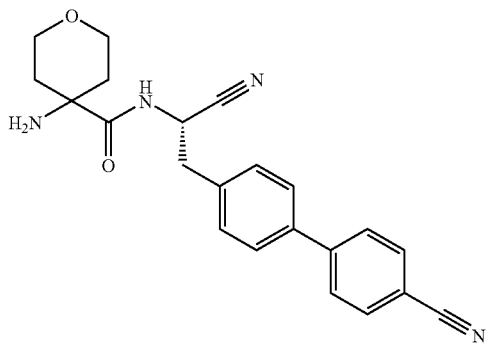

(i) (S)-tert-Butyl 1-amino-3-(4-iodophenyl)-1-oxopropan-2-ylcarbamate

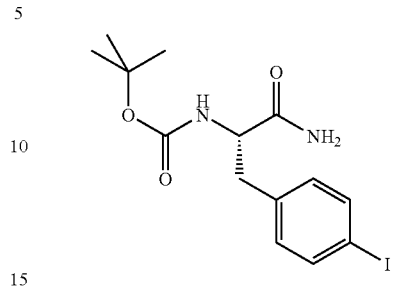

(S)-2-(tert-Butoxycarbonylamino)-3-(4-iodophenyl)propanoic acid (35.1 g) was dissolved in DMF (200 mL) and to the resulting solution was added N-ethylmorpholine (17.0 mL) followed by TBTU (28.8 g). The mixture was stirred at room temperature for 0.5 h and then cooled to 0° C. 0.880 Ammonia (11.1 mL) was added and the mixture was allowed to warm to room temperature. The mixture was stirred at room temperature for 16 h and was then to poured into water and the resulting precipitate removed by filtration. The solid was dried in vacuo to give the sub-titled compound (34.2 g).

m/e (APCI+) 291 [M+2H−BOC]$^+$

(ii) (S)-tert-Butyl 1-amino-3-(4'-cyanobiphenyl-4-yl)-1-oxopropan-2-ylcarbamate

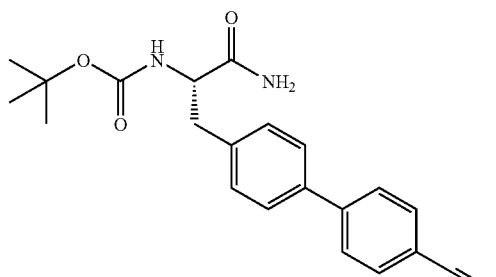

(S)-tert-Butyl 1-amino-3-(4-iodophenyl)-1-oxopropan-2-ylcarbamate (Example 3, step (i), 3.17 g) and 4-cyanophenylboronic acid (1.19 g) in dioxane (5 mL) were treated with 1,1 bis(di-tert-butylphosphino)ferrocene palladium dichloride (0.08 g) and the mixture was stirred at room temperature for 15 min under nitrogen. An aqueous solution of potassium carbonate (2M, 8.12 mL) was added and the mixture was stirred for 18 h at 75° C. The reaction mixture was extracted with ethyl acetate, dried and evaporated to afford the sub-titled compound (3.13 g).

m/e (APCI+) 266 [M+2H−BOC]$^+$ $^1$H NMR (400 MHz, CDCl$_3$) δ 7.74-7.70 (m, 2H), 7.68-7.65 (m, 2H), 7.56-7.52 (m, 2H), 7.35 (d, 2H), 5.87-5.78 (m,

1H), 5.39-5.30 (m, 1H), 5.08-4.98 (m, 1H), 4.45-4.37 (m, 1H), 3.20-3.07 (m, 2H), 1.42 (s, 9H).

(iii) (S)-2-Amino-3-(4'-cyanobiphenyl-4-yl)propanamide

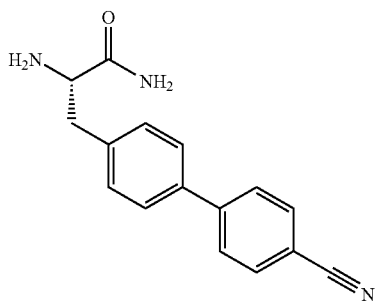

(S)-tert-Butyl 1-amino-3-(4'-cyanobiphenyl-4-yl)-1-oxopropan-2-ylcarbamate (Example 3, step (ii), 3.13 g) was dissolved in dichloromethane (30 mL) and TFA (1.32 mL) was added. The dichloromethane was distilled off on a rotary evaporator at atmospheric pressure to leave ~5 mL of solvent. The reaction was monitored by HPLC/MS and when complete was partitioned between water and dichloromethane. The organic layer was separated and the aqueous layer further extracted with dichloromethane. The combined organic extracts were dried (magnesium sulfate) and evaporated. The resulting solid was purified by chromatography on silica eluting with ethyl acetate then ethyl acetate containing 10% methanol to afford the sub-titled compound (1.95 g).

$^1$H NMR (400 MHz, CDCl$_3$) δ 7.73 (dd, 2H), 7.67 (dd, 2H), 7.56 (dt, 2H), 7.36 (dt, 2H), 7.11 (s, 1H), 5.38 (s, 1H), 3.68 (dd, 1H), 3.32 (dd, 1H), 2.84 (dd, 1H), 1.49 (s, 2H).

m/e (APCI+) 266.0 [M+H]$^+$

(iv) (S)-tert-Butyl 4-(1-amino-3-(4'-cyanobiphenyl-4-yl)-1-oxopropan-2-ylcarbamoyl)tetrahydro-2H-pyran-4-ylcarbamate

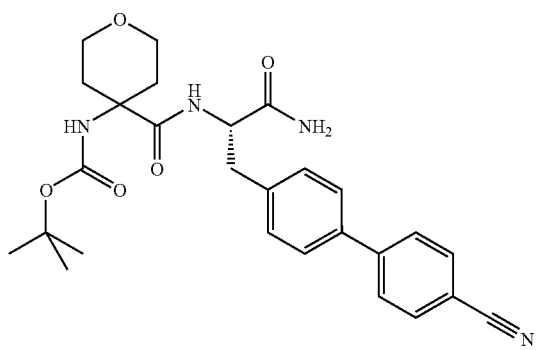

4-(tert-Butoxycarbonylamino)tetrahydro-2H-pyran-4-carboxylic acid (374 mg), (S)-2-amino-3-(4'-cyanobiphenyl-4-yl)propanamide (Example 3, step (iii), 405 mg) and N-ethyl-N-isopropylpropan-2-amine (0.664 mL) were dissolved in DMF (10 mL) and to the solution was added TBTU (734 mg). The reaction mixture was stirred at room temperature for 2 days. The reaction mixture was evaporated to dryness, dissolved in dichloromethane (20 mL) and was absorbed onto silica. The product was purified by chromatography on silica eluting with 20% ethyl acetate in isohexane, then 50% ethyl acetate in isohexane and then 100% ethyl acetate to afford after evaporation of the relevant fractions the sub-titled compound (700 mg).

m/e (APCI+) 393 [M+2H−BOC]$^+$

(v) (S)-tert-Butyl 4-(1-cyano-2-(4'-cyanobiphenyl-4-yl)ethylcarbamoyl)tetrahydro-2H-pyran-4-ylcarbamate

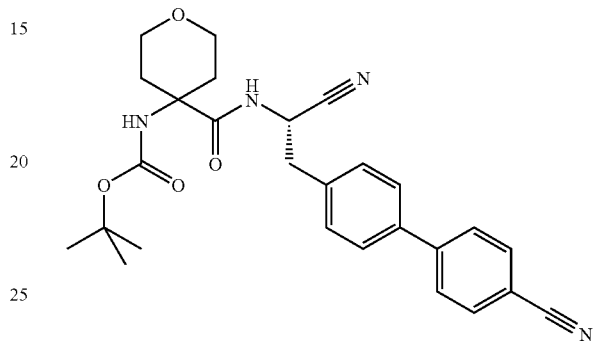

(S)-tert-Butyl 4-(1-amino-3-(4'-cyanobiphenyl-4-yl)-1-oxopropan-2-ylcarbamoyl)tetrahydro-2H-pyran-4-ylcarbamate (Example 3, step (iv), 0.70 g) in dichloromethane (15 mL) was treated with Burgess' reagent (0.356 g) and the mixture was stirred at room temperature for 6 h. Additional Burgess' reagent (0.15 g) was added and the reaction was stirred overnight. The mixture was absorbed onto silica and purified by chromatography on silica eluting with 33% ethyl acetate in isohexane and then 100% ethyl acetate to afford the sub-titled compound as a solid (0.420 g).

$^1$H NMR (399.824 MHz, CDCl$_3$) δ 7.74 (d, 2H), 7.67 (d, 2H), 7.59 (d, 2H), 7.42 (d, 2H), 5.14 (dd, 1H), 4.70 (s, 1H), 3.83-3.76 (m, 1H), 3.75-3.66 (m, 1H), 3.66-3.56 (m, 2H), 3.17 (dd, 1H), 3.12 (dd, 1H), 2.28-1.86 (m, 4H), 1.85-1.77 (m, 1H), 1.44 (s, 9H).

m/e (APCI−) 473 [M−H]$^-$

(S)-4-Amino-N-(1-cyano-2-(4'-cyanobiphenyl-4-yl)ethyl)tetrahydro-2H-pyran-4-carboxamide To (S)-tert-butyl 4-(1-cyano-2-(4'-cyanobiphenyl-4-yl)ethylcarbamoyl)tetrahydro-2H-pyran-4-ylcarbamate (Example 3, step (v), 420 mg) was added formic acid (2 mL) and the mixture heated to 50° C. for 10 min. The mixture was evaporated to dryness, dissolved in methanol (4 mL) and purified on reverse phase HPLC eluting with 25 to 85% acetonitrile in 0.1% TFA on a Water's Sunfire column. Fractions containing product were evaporated to remove acetonitrile, neutralised with saturated sodium bicarbonate and extracted with dichloromethane which was dried and evaporated to afford the titled compound as a solid (110 mg).

$^1$H NMR (399.824 MHz, CDCl$_3$) δ 8.28 (d, 1H), 7.73 (dd, 2H), 7.67 (d, 2H), 7.59 (d, 2H), 7.40 (d, 2H), 5.13 (dt, 1H), 3.94-3.82 (m, 2H), 3.66-3.56 (m, 2H), 3.17 (d, 2H), 2.34-2.24 (m, 1H), 2.23-2.13 (m, 1H), 1.49 (s, 2H), 1.30 (dq, 1H), 1.20 (dq, 1H).

m/e (MultiMode+) 375 [M+H]$^+$

EXAMPLE 4

(S)-4-Amino-N-(1-cyano-2-(4'-fluorobiphenyl-4-yl)ethyl)tetrahydro-2H-pyran-4-carboxamide

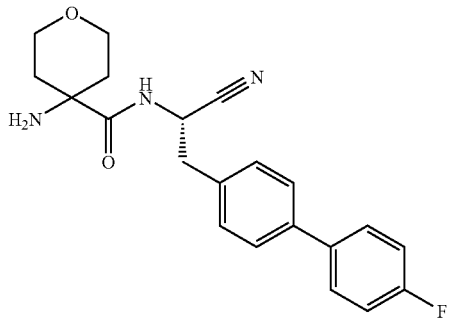

(i) (S)-tert-Butyl 4-(1-amino-3-(4'-fluorobiphenyl-4-yl)-1-oxopropan-2-ylcarbamoyl)tetrahydro-2H-pyran-4-ylcarbamate

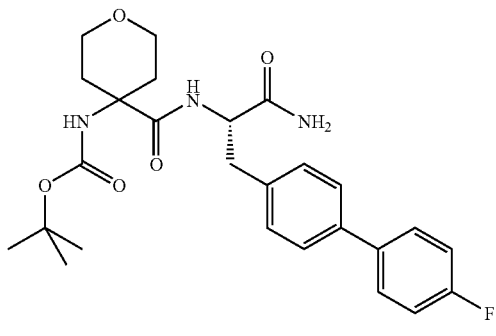

and (S)-tert-butyl 4-(1-amino-3-(4'-(isopropylsulfonyl)biphenyl-4-yl)-1-oxopropan-2-ylcarbamoyl)tetrahydro-2H-pyran-4-ylcarbamate

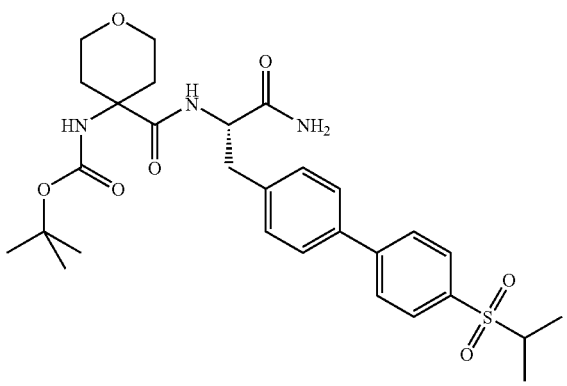

(S)-tert-Butyl 4-(1-amino-3-(4-iodophenyl)-1-oxopropan-2-ylcarbamoyl)tetrahydro-2H-pyran-4-ylcarbamate (Example 1, step (iii), 1.0 g) in acetonitrile (5 mL) under nitrogen was treated with 4-fluorophenylboronic acid (0.135 g) and 4-(isopropylsulfonyl)phenylboronic acid (0.220 g) followed by aqueous potassium carbonate (2M, 1.93 mL) and 1,1 bis(di-tert-butylphosphino)ferrocene palladium dichloride (13 mg). The mixture was stirred at 75° C. for 18 h. The reaction was evaporated, dissolved in dichloromethane, absorbed onto silica and to purified by chromatography on silica eluting with 50% ethyl acetate in isohexane and then 100% ethyl acetate to afford (S)-tert-butyl 4-(1-amino-3-(4'-fluorobiphenyl-4-yl)-1-oxopropan-2-ylcarbamoyl)tetrahydro-2H-pyran-4-ylcarbamate and (S)-tert-butyl 4-(1-amino-3-(4'-(isopropylsulfonyl)biphenyl-4-yl)-1-oxopropan-2-ylcarbamoyl)tetrahydro-2H-pyran-4-ylcarbamate as a mixture (0.620 g).

Data for (S)-tert-butyl 4-(1-amino-3-(4'-fluorobiphenyl-4-yl)-1-oxopropan-2-ylcarbamoyl)tetrahydro-2H-pyran-4-ylcarbamate m/e (APCI+) 386 [M+2H−BOC]$^+$ Data for (S)-tert-butyl 4-(1-amino-3-(4'-(isopropylsulfonyl)biphenyl-4-yl)-1-oxopropan-2-ylcarbamoyl)tetrahydro-2H-pyran-4-ylcarbamate m/e (APCI+) 474 [M+2H−BOC]$^+$ (ii(i)) (S)-tert-Butyl 4-(1-cyano-2-(4'-fluorobiphenyl-4-yl)ethylcarbamoyl)tetrahydro-2H-pyran-4-ylcarbamate

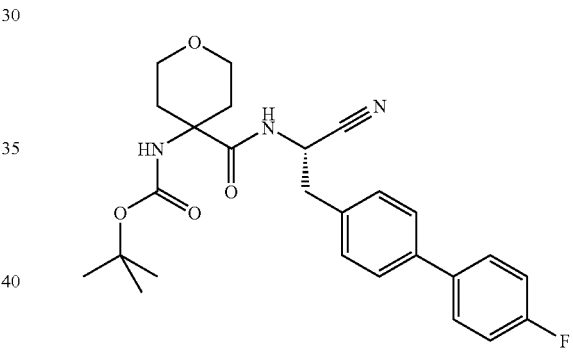

and (ii(ii)) (S)-tert-butyl 4-(1-cyano-2-(4'-(isopropylsulfonyl)biphenyl-4-yl)ethylcarbamoyl)tetrahydro-2H-pyran-4-ylcarbamate

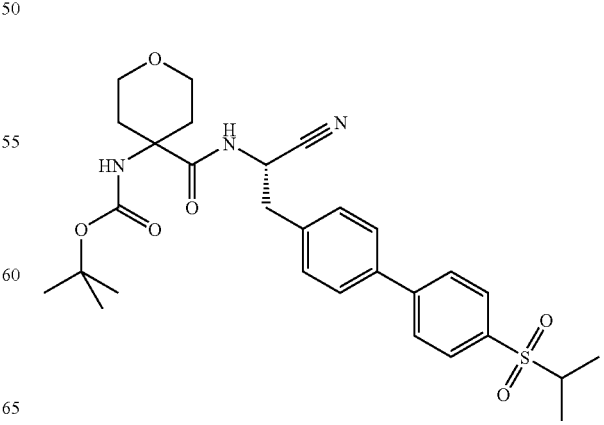

The mixture of (S)-tert-butyl 4-(1-amino-3-(4'-fluorobiphenyl-4-yl)-1-oxopropan-2-ylcarbamoyl)tetrahydro-2H-pyran-4-ylcarbamate and (S)-tert-butyl 4-(1-amino-3-(4'-(isopropylsulfonyl)biphenyl-4-yl)-1-oxopropan-2-ylcarbamoyl)tetrahydro-2H-pyran-4-ylcarbamate (Example 4, step (i), 620 mg) in dichloromethane (15 mL) was treated with Burgess' reagent (462 mg) and the mixture was stirred at room temperature for 2 days. The reaction was absorbed onto silica and was purified by chromatography on silica eluting with 25% ethyl acetate in isohexane and then 50% ethyl acetate in isohexane to afford after evaporation of the relevant fractions (S)-tert-butyl 4-(1-cyano-2-(4'-fluorobiphenyl-4-yl)ethylcarbamoyl)tetrahydro-2H-pyran-4-ylcarbamate (218 mg) and (S)-tert-butyl 4-(1-cyano-2-(4'-(isopropylsulfonyl)biphenyl-4-yl)ethylcarbamoyl)tetrahydro-2H-pyran-4-ylcarbamate (300 mg).

Data for (S)-tert-butyl 4-(1-cyano-2-(4'-fluorobiphenyl-4-yl)ethylcarbamoyl)tetrahydro-2H-pyran-4-ylcarbamate $^1$H NMR (399.824 MHz, CDCl$_3$) δ 7.76-7.45 (m, 1H), 7.55-7.53 (m, 2H), 7.52 (t, 2H), 7.35 (d, 2H), 7.13 (tquintet, 2H), 5.13 (dd, 1H), 4.75 (s, 1H), 3.84-3.75 (m, 1H), 3.74-3.65 (m, 1H), 3.65-3.55 (m, 2H), 3.13 (ddd, 2H), 2.27-2.06 (m, 2H), 1.95 (s, 1H), 1.81 (d, 1H), 1.44 (s, 9H).

m/e (APCI−) 466 [M−H]$^−$

Data for (S)-tert-butyl 4-(1-cyano-2-(4'-(isopropylsulfonyl)biphenyl-4-yl)ethylcarbamoyl)tetrahydro-2H-pyran-4-ylcarbamate $^1$H NMR (399.824 MHz, CDCl$_3$) δ 7.94 (d, 2H), 7.83-7.66 (m, 1H), 7.75 (dt, 2H), 7.61 (d, 2H), 7.42 (d, 2H), 5.14 (dd, 1H), 3.85-3.76 (m, 1H), 3.74-3.56 (m, 3H), 3.29-3.09 (m, 4H), 2.26-2.04 (m, 2H), 1.96 (s, 1H), 1.82 (d, 1H), 1.44 (s, 9H), 1.34 (d, 6H).

m/e (APCI−) 555 [M−H]$^−$ (S)-4-Amino-N-(1-cyano-2-(4'-fluorobiphenyl-4-yl)ethyl)tetrahydro-2H-pyran-4-carboxamide To (S)-tert-butyl 4-(1-cyano-2-(4'-fluorobiphenyl-4-yl)ethylcarbamoyl)tetrahydro-2H-pyran-4-ylcarbamate (Example 4, step (ii(i)), 218 mg) was added formic acid (4 mL) and the mixture heated to 50° C. for 20 min. The mixture was evaporated to dryness, dissolved in methanol (10 mL), re-evaporated to dryness, dissolved in methanol (6 mL) and purified on reverse phase HPLC eluting with 25% to 95% methanol in 0.1% aqueous TFA on a Waters SunFire column. The material was converted to free base by evaporating the relevant fractions, dissolving in dichloromethane (20 mL) and shaking with saturated sodium bicarbonate solution (20 mL). The dichloromethane was separated, dried and evaporated to afford the titled compound (100 mg).

$^1$H NMR (399.824 MHz, CDCl$_3$) δ 8.23 (d, 1H), 7.56-7.50 (m, 4H), 7.33 (d, 2H), 7.13 (tt, 2H), 5.12 (dt, 1H), 3.94-3.82 (m, 2H), 3.65-3.54 (m, 2H), 3.14 (d, 2H), 2.33-2.24 (m, 1H), 2.22-2.13 (m, 1H), 1.48 (s, 2H), 1.28 (dq, 1H), 1.18 (dq, 1H).

m/e (MultiMode+) 368 [M+H]$^+$

EXAMPLE 5

(S)-4-Amino-N-(1-cyano-2-(4'-(isopropylsulfonyl)biphenyl-4-yl)ethyl)tetrahydro-2H-pyran-4-carboxamide

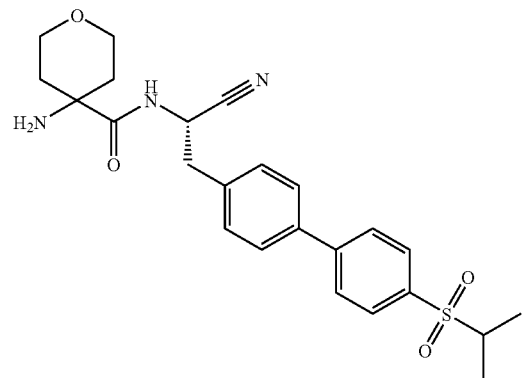

To (S)-tert-butyl 4-(1-cyano-2-(4'-(isopropylsulfonyl)biphenyl-4-yl)ethylcarbamoyl)tetrahydro-2H-pyran-4-ylcarbamate (Example 4, step (ii(ii)), 300 mg) was added formic acid (4 mL) and the mixture heated to 50° C. for 20 min. The mixture was evaporated to dryness, dissolved in methanol (10 mL), re-evaporated to dryness, dissolved in methanol (6 mL) and purified on reverse phase HPLC eluting with 25 to 95% methanol in 0.1% aqueous TFA on a Waters SunFire column. The material was converted to free base by evaporating the relevant fractions, dissolving in dichloromethane (20 mL) and shaking with saturated sodium bicarbonate solution (20 mL). The dichloromethane was dried and evaporated to afford the titled compound (67 mg).

$^1$H NMR (399.824 MHz, CDCl$_3$) δ 8.27 (d, 1H), 7.95 (d, 2H), 7.75 (d, 2H), 7.62 (d, 2H), 7.40 (d, 2H), 5.18-5.10 (m, 1H), 3.96-3.83 (m, 2H), 3.67-3.56 (m, 2H), 3.29-3.18 (m, 1H), 3.17 (d, 2H), 2.36-2.25 (m, 1H), 2.25-2.14 (m, 1H), 1.58 (s, 2H), 1.34 (d, 6H), 1.33-1.27 (m, 1H), 1.25-1.17 (m, 1H).

m/e (MultiMode+) 456 [M+H]$^+$

EXAMPLE 6

(S)-4'-(2-(4-Aminotetrahydro-2H-pyran-4-carboxamido)-2-cyanoethyl)biphenyl-4-yl methanesulfonate trifluoroacetic acid salt

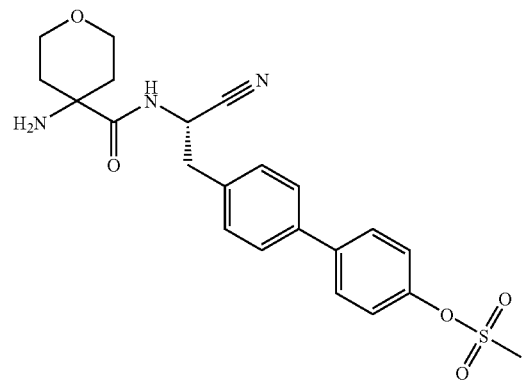

(i) (S)-4'-(3-Amino-2-(4-(tert-butoxycarbonylamino)tetrahydro-2H-pyran-4-carboxamido)-3-oxopropyl)biphenyl-4-yl methanesulfonate

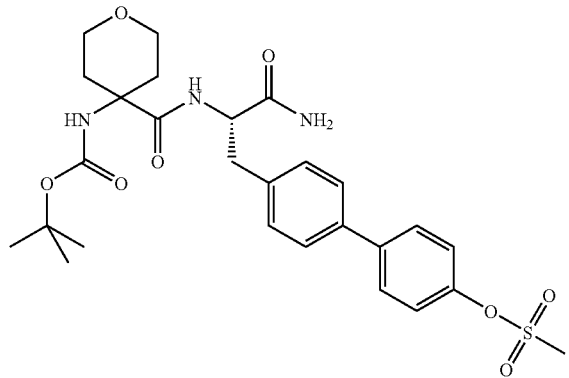

(S)-tert-Butyl 4-(1-amino-3-(4-iodophenyl)-1-oxopropan-2-ylcarbamoyl)tetrahydro-2H-pyran-4-ylcarbamate (Example 1, step (iii), 300 mg) in acetonitrile (7 mL) under nitrogen was treated with 4-(methylsulfonyloxy)phenylboronic acid (125 mg) followed by aqueous sodium carbonate (2M, 0.58 mL). Nitrogen was bubbled through the mixture and 1,1 bis(di-tert-butylphosphino)ferrocene palladium dichloride (5 mg) was added. The mixture was stirred at 85° C. for 25 h. The solvent was partially evaporated and then purified by chromatography on silica using ethyl acetate 50-100% isohexane as eluent to afford the sub-titled compound as a white solid (234 mg).

m/e (APCI+) 462 [M+2H−BOC]$^+$ (ii) (S)-4'-(2-(4-(tert-Butoxycarbonylamino)tetrahydro-2H-pyran-4-carboxamido)-2-cyanoethyl)biphenyl-4-yl methanesulfonate

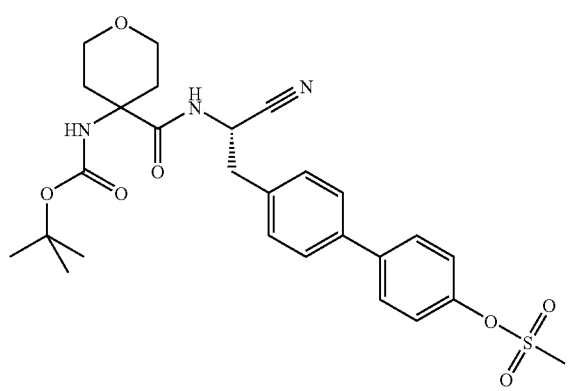

(S)-4'-(3-Amino-2-(4-(tert-butoxycarbonylamino)tetrahydro-2H-pyran-4-carboxamido)-3-oxopropyl)biphenyl-4-yl methanesulfonate (Example 6, step (i), 234 mg) in dichloromethane (8 mL) was treated with Burgess' reagent (199 mg) and the mixture was stirred at room temperature for 18 h. It was partially evaporated and then purified by chromatography on silica using diethyl ether and then 1:1 ethyl acetate/isohexane as eluent to a afford the sub-titled compound as a white solid (267 mg).

m/e (APCI+) 444 [M+2H−BOC]$^+$ (S)-4'-(2-(4-Aminotetrahydro-2H-pyran-4-carboxamido)-2-cyanoethyl)biphenyl-4-yl methanesulfonate trifluoroacetic acid salt (S)-4'-(2-(4-(tert-Butoxycarbonylamino)tetrahydro-2H-pyran-4-carboxamido)-2-cyanoethyl)biphenyl-4-yl methanesulfonate (Example 6, step (ii), 267 mg) was treated with formic acid (2 mL) and the mixture was stirred at room temperature for 4.5 h. Water was added and the cooled solution was made basic with 0.880 ammonia and then extracted (×3) with dichloromethane. The combined organic extracts were dried over magnesium sulphate, filtered and the solvent was evaporated. The product was purified by reversed phase chromatography using a gradient of 5% to 95% Methanol/0.1% aq. TFA on a Waters SunFire column to yield the titled compound as a white solid (88 mg).

$^1$H NMR (399.826 MHz, d$_6$-DMSO) δ 9.23 (d, 1H), 8.44 (s, 3H), 7.78-7.73 (m, 2H), 7.65 (d, 2H), 7.46-7.39 (m, 4H), 5.17-5.10 (m, 1H), 3.70-3.62 (m, 2H), 3.62-3.54 (m, 2H), 3.42 (s, 3H), 3.32-3.15 (m, 2H), 2.18 (dt, 1H), 2.09-1.97 (m, 1H), 1.68 (d, 1H), 1.48 (d, 1H).

m/e (MultiMode+) 444 [M+H]$^+$

EXAMPLE 7

(S)-4-Amino-N-(2-(4'-(azetidin-1-ylsulfonyl)biphenyl-4-yl)-1-cyanoethyl)tetrahydro-2H-pyran-4-carboxamide trifluoroacetic acid salt (i) (S)-tert-Butyl 4-(1-amino-3-(4'-(azetidin-1-ylsulfonyl)biphenyl-4-yl)-1-oxopropan-2-ylcarbamoyl)tetrahydro-2H-pyran-4-ylcarbamate (S)-tert-Butyl 4-(1-amino-3-(4-iodophenyl)-1-oxopropan-2-ylcarbamoyl)tetrahydro-2H-pyran-4-ylcarbamate (Example 1, step (iii), 350 mg) in acetonitrile (7 mL) under nitrogen was treated with 4-(azetidin-1-ylsulfonyl)phenylboronic acid (163 mg) followed by sodium carbonate (0.677 mL). Nitrogen was bubbled through the mixture and 1,1 bis(di-tert-butylphosphino)ferrocene palladium dichloride (10 mg) was added. The mixture was stirred at 85° C. for 25 h. The solvent was partially evaporated and the solution was purified by chromatography on silica using ethyl acetate 50-100% in isohexane as eluent to afford the sub-titled compound as a solid (309 mg).

m/e (APCI+) 487 [M+2H−BOC]+

(ii) (S)-tert-Butyl 4-(2-(4'-(azetidin-1-ylsulfonyl)biphenyl-4-yl)-1-cyanoethylcarbamoyl)tetrahydro-2H-pyran-4-ylcarbamate

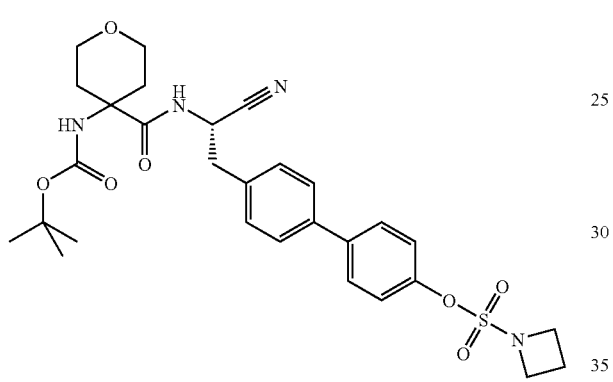

(S)-tert-Butyl 4-(1-amino-3-(4'-(azetidin-1-ylsulfonyl)biphenyl-4-yl)-1-oxopropan-2-ylcarbamoyl)tetrahydro-2H-pyran-4-ylcarbamate (Example 7, step (i), 309 mg) in dichloromethane (8 mL) was treated with Burgess' reagent (251 mg) and the mixture was stirred at room temperature for 18 h. The solvent was partially evaporated and then purified by chromatography on silica using diethyl ether and then 1:1 ethyl acetate/isohexane as eluent to yield a white solid (222 mg).

m/e (APCI+) 469 [M+2H−BOC]+

(S)-4-Amino-N-(2-(4'-(azetidin-1-ylsulfonyl)biphenyl-4-yl)-1-cyanoethyl)tetrahydro-2H-pyran-4-carboxamide trifluoroacetic acid salt (S)-tert-Butyl 4-(2-(4'-(azetidin-1-ylsulfonyl)biphenyl-4-yl)-1-cyanoethylcarbamoyl)tetrahydro-2H-pyran-4-ylcarbamate (Example 7, step (ii), 222 mg) was treated with formic acid (2 mL) and the mixture was stirred at room temperature for 4.5 h. Water was added and the cooled solution was made basic with 0.880 ammonia and then extracted (×3) with dichloromethane. The combined organic phases were dried over magnesium sulphate, filtered and the solvent was evaporated. The product was purified by chromatography on silica using ethyl acetate as eluent and then crystallised from isopropanol. Further purification by reversed phase chromatography eluting with a gradient of 5% to 95% methanol/0.1% aq. TFA on a Waters SunFire column afforded the sub-titled compound as a white solid (57 mg).

$^1$H NMR (399.826 MHz, d$_6$-DMSO) δ 9.24 (d, 1H), 8.45 (s, 3H), 7.97 (d, 2H), 7.87 (d, 2H), 7.76 (d, 2H), 7.47 (d, 2H), 5.20-5.12 (m, 1H), 3.74-3.64 (m, 5H), 3.62-3.55 (m, 2H), 3.37-3.16 (m, 3H), 2.24-2.14 (m, 1H), 2.09-1.96 (m, 3H), 1.69 (d, 1H), 1.48 (d, 1H).

m/e (MultiMode+) 469 [M+H]+

EXAMPLE 8

(S)-4-Amino-N-(1-cyano-2-(3'-cyanobiphenyl-4-yl)ethyl)tetrahydro-2H-pyran-4-carboxamide

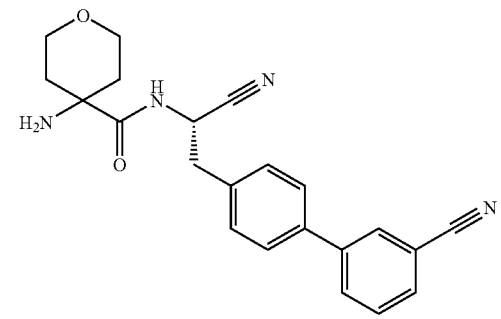

(i) (S)-tert-Butyl 4-(1-amino-3-(3'-cyanobiphenyl-4-yl)-1-oxopropan-2-ylcarbamoyl)tetrahydro-2H-pyran-4-ylcarbamate

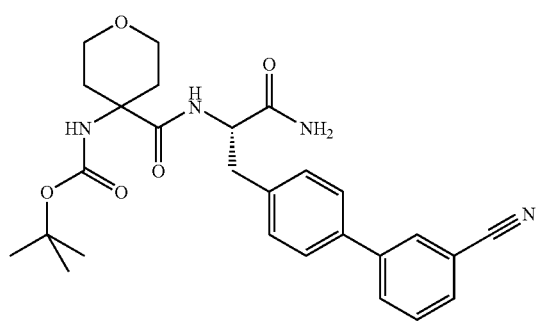

(S)-tert-Butyl 4-(1-amino-3-(4-iodophenyl)-1-oxopropan-2-ylcarbamoyl)tetrahydro-2H-pyran-4-ylcarbamate (Example 1, step (iii), 350 mg) in acetonitrile (7 mL) under nitrogen was treated with 3-cyanophenylboronic acid (99 mg) followed by aqueous sodium carbonate (2M, 0.677 mL). Nitrogen was bubbled through and 1,1 bis(di-tert-butylphosphino)ferrocene palladium dichloride (10 mg) was added. The mixture was stirred at 85° C. for 25 h. The solvent was partially evaporated and the solution was purified by chromatography on silica using 50% ethyl acetate in isohexane and then ethyl acetate as eluent to afford the sub-titled compound as a solid (316 mg).

m/e (APCI+) 393 [M+2H−BOC]+

45

(ii) (S)-tert-Butyl 4-(1-cyano-2-(3'-cyanobiphenyl-4-yl)ethylcarbamoyl)tetrahydro-2H-pyran-4-ylcarbamate

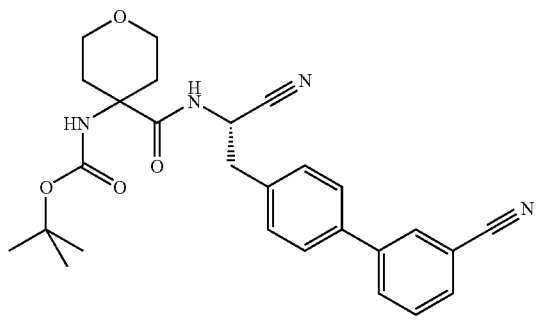

(S)-tert-Butyl 4-(1-amino-3-(3'-cyanobiphenyl-4-yl)-1-oxopropan-2-ylcarbamoyl)tetrahydro-2H-pyran-4-ylcarbamate (Example 8, step (i), 316 mg) in dichloromethane (8 mL) was treated with Burgess' reagent (306 mg) and the mixture was stirred at room temperature for 18 h. The solvent was partially evaporated and the solution was purified by chromatography on silica using ethyl acetate/isohexane and then ethyl acetate as eluent to afford the sub-titled compound as a white solid (282 mg).

m/e (APCI+) 375 [M+2H−BOC]+

(S)-4-Amino-N-(1-cyano-2-(3'-cyanobiphenyl-4-yl)ethyl)tetrahydro-2H-pyran-4-carboxamide (S)-tert-butyl 4-(1-cyano-2-(3'-cyanobiphenyl-4-yl)ethylcarbamoyl)tetrahydro-2H-pyran-4-ylcarbamate (Example 8, step (ii), 282 mg) in formic acid (1.5 mL) was stirred at room temperature for 5 h, warmed at 36° C. for 30 mins then stirred at room temperature overnight. Water was added and the cooled solution was made basic with 0.880 ammonia and then extracted (×3) with dichloromethane. The combined organic extracts were dried over magnesium sulphate, filtered and the solvent was evaporated to yield an oil which was purified by chromatography on silica using 80% ethyl acetate in isohexane as eluent and then crystallised from isopropanol to yield a solid. The solid was washed with diethyl ether and dried to afford the titled compound (89 mg).

$^1$H NMR (399.826 MHz, d$_6$-DMSO) δ 8.14 (t, 1H), 8.01 (dt, 1H), 7.82 (d, 1H), 7.71 (d, 2H), 7.66 (t, 1H), 7.42 (d, 2H), 5.01 (t, 1H), 3.67-3.53 (m, 3H), 3.50-3.42 (m, 1H), 3.26-3.15 (m, 2H), 1.94-1.84 (m, 1H), 1.78-1.69 (m, 1H), 1.25-1.17 (m, 1H), 1.17-1.09 (m, 1H).

m/e (MultiMode+) 375 [M+H]+

EXAMPLE 9

(S)-4-Amino-N-(1-cyano-2-(4-(3-(2-methoxyethyl)-2-oxo-2,3-dihydrobenzo[d]thiazol-5-yl)phenyl)ethyl)tetrahydro-2H-pyran-4-carboxamide trifluoroacetic acid salt

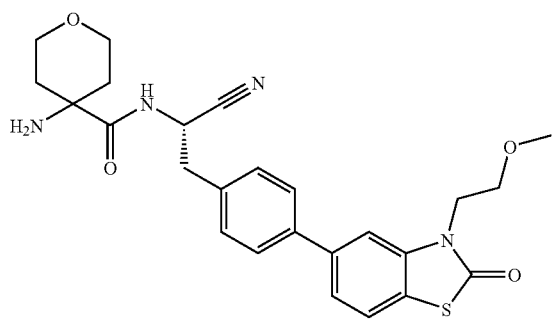

46

(i) 5-Bromo-3-(2-methoxyethyl)benzo[d]thiazol-2(3H)-one

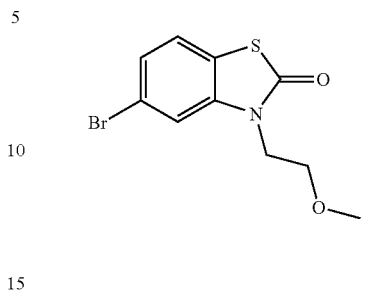

5-Bromobenzo[d]thiazol-2(3H)-one (1 g) and potassium carbonate (1.502 g) were stirred in DMF (7 mL) at room temperature and 1-bromo-2-methoxyethane (0.408 mL) was added. The mixture was stirred for 24 h. The mixture was poured onto water and extracted with ethyl acetate. The extracts were washed with dilute hydrochloric acid, water and brine then dried over sodium sulfate and evaporated. Purification by flash silica chromatography eluting with 10% ethyl acetate in isohexane afforded the sub-titled compound as a colourless solid (0.73 g).

$^1$H NMR (399.824 MHz, CDCl$_3$) δ 7.36 (t, 1H), 7.28-7.26 (m, 2H), 4.09 (t, 2H), 3.68 (t, 2H), 3.34 (s, 3H).

(ii) 3-(2-Methoxyethyl)-5-(4,4,5,5-tetramethyl-1,3,2-dioxaborolan-2-yl)benzo[d]thiazol-2(3H)-one

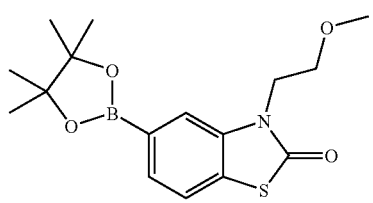

To a mixture of 5-bromo-3-(2-methoxyethyl)benzo[d]thiazol-2(3H)-one (Example 9, step (i), 300 mg) and 4,4,4',4',5,5,5',5'-octamethyl-2,2'-bi(1,3,2-dioxaborolane) (397 mg) in acetonitrile (8 mL) was added potassium acetate (307 mg) and then nitrogen was bubbled through the mixture. 1,1 bis(Di-tert-butylphosphino)ferrocene palladium dichloride (6 mg) was added and the mixture was heated at 85° C. for 18 h. HPLC-MS showed partial reaction so a further addition of 1,1 bis(di-tert-butylphosphino)ferrocene palladium dichloride was made and the mixture was heated for a further 18 h. 4,4,4',4',5,5,5',5'-Octamethyl-2,2'-bi(1,3,2-dioxaborolane) (100 mg) and 1,1 bis(di-tert-butylphosphino)ferrocene palladium dichloride (5 mg) were added and the mixture was heated for a further 18 h. The cooled solution was purified by chromatography on silica using 1:1 ethyl acetate/isohexane as eluent to yield the sub-titled compound (203 mg).

m/e (APCI+) 336 [M+H]+

(iii) (S)-tert-Butyl 4-(1-amino-3-(4-(3-(2-methoxy-ethyl)-2-oxo-2,3-dihydrobenzo[d]thiazol-5-yl)phenyl)-1-oxopropan-2-ylcarbamoyl)tetrahydro-2H-pyran-4-ylcarbamate

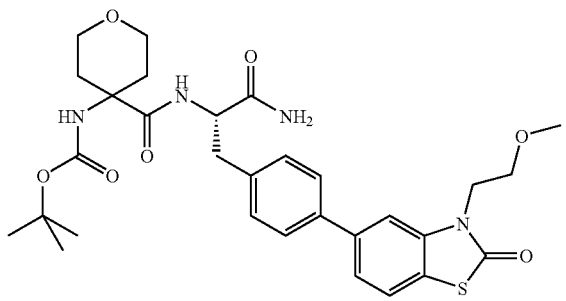

(S)-tert-butyl 4-(1-amino-3-(4-iodophenyl)-1-oxopropan-2-ylcarbamoyl)tetrahydro-2H-pyran-4-ylcarbamate (Example 1, step (iii), 203 mg) in acetonitrile (7 mL) under nitrogen was treated with 3-(2-methoxyethyl)-5-(4,4,5,5-tetramethyl-1,3,2-dioxaborolan-2-yl)benzo[d]thiazol-2(3H)-one (Example 9, step (ii), 132 mg) followed by aqueous sodium carbonate (2M, 0.392 mL). Nitrogen was bubbled through the mixture and 1,1 bis(di-tert-butylphosphino)ferrocene palladium dichloride (5 mg) was added. The mixture was stirred at 85° C. for 25 h and then allowed to cool. The solution was purified by chromatography on silica using ethyl acetate 50-100% in isohexane as eluent to afford the sub-titled compound (155 mg).

m/e (APCI−) 597 [M−H]−

(iv) (S)-tert-Butyl 4-(1-cyano-2-(4-(3-(2-methoxy-ethyl)-2-oxo-2,3-dihydrobenzo[d]thiazol-5-yl)phenyl)ethylcarbamoyl)tetrahydro-2H-pyran-4-ylcarbamate

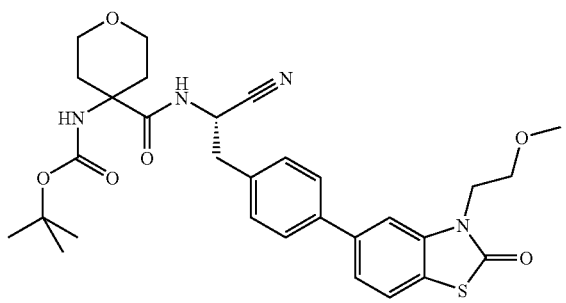

(S)-tert-Butyl 4-(1-amino-3-(4-(3-(2-methoxyethyl)-2-oxo-2,3-dihydrobenzo[d]thiazol-5-yl)phenyl)-1-oxopropan-2-ylcarbamoyl)tetrahydro-2H-pyran-4-ylcarbamate (Example 9, step (iii), 155 mg) in dichloromethane (8 mL) was treated with Burgess' reagent (123 mg) and the mixture was stirred at room temperature for 18 h. The solvent was partially evaporated and the mixture was purified by chromatography on silica using ethyl acetate/isohexane (1:1) as eluent to yield the sub-titled compound (179 mg).

m/e (APCI−) 579 [M−H]−

(S)-4-Amino-N-(1-cyano-2-(4-(3-(2-methoxyethyl)-2-oxo-2,3-dihydrobenzo[d]thiazol-5-yl)phenyl)ethyl)tetrahydro-2H-pyran-4-carboxamide trifluoroacetic acid salt (S)-tert-Butyl 4-(1-cyano-2-(4-(3-(2-methoxyethyl)-2-oxo-2,3-dihydrobenzo[d]thiazol-5-yl)phenyl)ethylcarbamoyl)tetrahydro-2H-pyran-4-ylcarbamate (Example 9, step (iv), 179 mg) was treated with formic acid (1.5 mL) and stirred at room temperature for 4 h. The mixture was evaporated to give an oil and redissolved in methanol. The mixture was then evaporated and purified by reversed phase chromatography eluting with a gradient of 5% to 95% methanol/0.1% aq TFA on a Waters SunFire column and evaporated to yield a white solid (56 mg).

$^1$H NMR (399.826 MHz, $d_6$-DMSO) δ 9.23 (d, 1H), 8.45 (s, 3H), 7.72 (dd, 3H), 7.62 (d, 1H), 7.49 (dd, 1H), 7.43 (d, 2H), 5.18-5.09 (m, 1H), 4.24 (t, 2H), 3.71-3.54 (m, 6H), 3.33-3.17 (m, 2H), 3.23 (s, 3H), 2.25-2.15 (m, 1H), 2.10-1.99 (m, 1H), 1.69 (d, 1H), 1.49 (d, 1H).

m/e (MultiMode+) 481 [M+H]+

EXAMPLE 10

(S)-4-Amino-N-(1-cyano-2-(4-(4-methyl-3-oxo-3,4-dihydro-2H-benzo[b][1,4]oxazin-6-yl)phenyl)ethyl)tetrahydro-2H-pyran-4-carboxamide trifluoroacetic acid salt

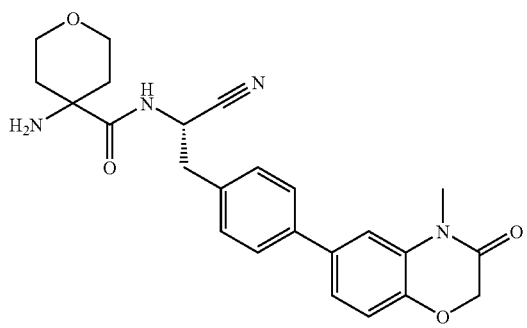

(i) 6-Bromo-4-methyl-2H-benzo[b][1,4]oxazin-3(4H)-one

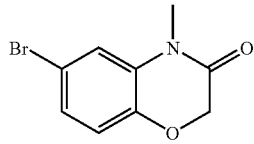

To sodium hydride (63 mg) in DMF (3 mL) under an atmosphere of nitrogen was added 6-bromo-2H-benzo[b][1,4]oxazin-3(4H)-one (0.3 g) and the mixture was stirred at room temperature for 1 h. Methyl iodide (0.123 mL) was added and the mixture was stirred overnight at room temperature. The mixture was poured onto ice/water and extracted into ethyl acetate (×2). The ethyl acetate was washed with water (×3), dried and the solvent was evaporated. The resulting material was purified by chromatography on silica eluting with 10% ethyl acetate/isohexane to afford the sub-titled compound (299 mg).

$^1$H NMR (399.826 MHz, $d_6$-DMSO) δ 7.33 (d, 1H), 7.18 (dd, 1H), 6.96 (d, 1H), 4.67 (s, 2H), 3.26 (s, 3H).

(ii) 4-Methyl-6-(4,4,5,5-tetramethyl-1,3,2-dioxaborolan-2-yl)-2H-benzo[b][1,4]oxazin-3(4H)-one

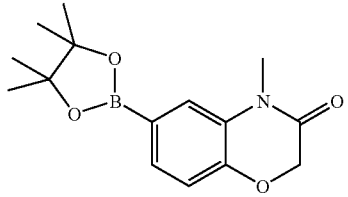

To 6-bromo-4-methyl-2H-benzo[b][1,4]oxazin-3(4H)-one (Example 10, step (i), 0.14 g) and 4,4,4',4',5,5,5',5'-octamethyl-2,2'-bi(1,3,2-dioxaborolane) (0.220 g) in acetonitrile (6 mL) was added potassium acetate (0.170 g) and nitrogen was bubbled through the mixture. 1,1 bis(Di-tert-butylphosphino)ferrocene palladium dichloride (5 mg) was added and the mixture was heated at 85° C. for 18 h. The mixture was absorbed onto silica and purified by chromatography on silica using 5-100% ethyl acetate/isohexane as eluent to afford the sub-titled compound (154 mg).

m/e (APCI+) 290 [M+H]$^+$

(iii) (S)-tert-Butyl 4-(1-amino-3-(4-(4-methyl-3-oxo-3,4-dihydro-2H-benzo[b][1,4]oxazin-6-yl)phenyl)-1-oxopropan-2-ylcarbamoyl)tetrahydro-2H-pyran-4-ylcarbamate

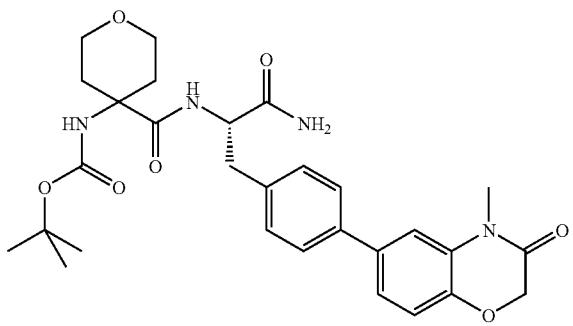

(S)-tert-Butyl 4-(1-amino-3-(4-iodophenyl)-1-oxopropan-2-ylcarbamoyl)tetrahydro-2H-pyran-4-ylcarbamate (Example 1, step (iii), 276 mg) in acetonitrile (7 mL) under nitrogen was treated with 4-methyl-6-(4,4,5,5-tetramethyl-1,3,2-dioxaborolan-2-yl)-2H-benzo[b][1,4]oxazin-3(4H)-one (Example 10, step (ii), 154 mg) followed by sodium carbonate (0.533 mL). Nitrogen was bubbled through the mixture and 1,1 bis(di-tert-butylphosphino)ferrocene palladium dichloride (5 mg) was added. The mixture was stirred at 85° C. for 25 h and then allowed to cool. The solution was absorbed onto silica and purified by chromatography on silica using ethyl acetate 50-100% in isohexane as eluent to afford the sub-titled compound (155 mg).

m/e (APCI−) 551 [M−H]$^−$

(iv) (S)-tert-Butyl 4-(1-cyano-2-(4-(4-methyl-3-oxo-3,4-dihydro-2H-benzo[b][1,4]oxazin-6-yl)phenyl)ethylcarbamoyl)tetrahydro-2H-pyran-4-ylcarbamate

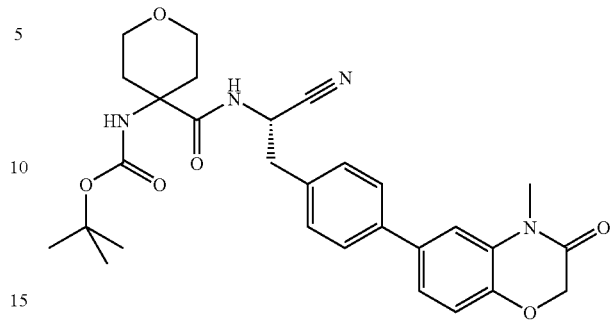

(S)-tert-Butyl 4-(1-amino-3-(4-(4-methyl-3-oxo-3,4-dihydro-2H-benzo[b][1,4]oxazin-6-yl)phenyl)-1-oxopropan-2-ylcarbamoyl)tetrahydro-2H-pyran-4-ylcarbamate (Example 10, step (iii), 155 mg) in dichloromethane (8 mL) was stirred at room temperature for 18 h with Burgess' reagent (134 mg). The solvent was partially evaporated and the mixture was absorbed onto silica for purification on a silica column using ethyl acetate/isohexane 1:1 as eluent to yield the sub-titled compound as a solid (156 mg).

m/e (APCI−) 533 [M−H]$^−$

(S)-4-Amino-N-(1-cyano-2-(4-(4-methyl-3-oxo-3,4-dihydro-2H-benzo[b][1,4]oxazin-6-yl)phenyl)ethyl)tetrahydro-2H-pyran-4-carboxamide trifluoroacetic acid salt (S)-tert-Butyl 4-(1-cyano-2-(4-(4-methyl-3-oxo-3,4-dihydro-2H-benzo[b][1,4]oxazin-6-yl)phenyl)ethylcarbamoyl)tetrahydro-2H-pyran-4-ylcarbamate (Example 10, step (iv), 156 mg) was treated with formic acid (1.5 mL) and stirred at room temperature for 5 h. The mixture was evaporated to give an oil and redissolved in methanol. The mixture was then evaporated and purified by reversed phase chromatography eluting with a gradient of 5% to 95% methanol/0.1% aq TFA on a Waters SunFire column and evaporated to yield the titled compound as a white solid (55 mg).

$^1$H NMR (399.826 MHz, d$_6$-DMSO) δ 9.23 (d, 1H), 8.45 (s, 3H), 7.66 (d, 2H), 7.40 (d, 2H), 7.35 (d, 1H), 7.30 (dd, 1H), 7.08 (d, 1H), 5.16-5.08 (m, 1H), 4.68 (s, 2H), 3.71-3.63 (m, 2H), 3.63-3.55 (m, 2H), 3.37 (s, 3H), 3.30-3.15 (m, 2H), 2.25-2.14 (m, 1H), 2.10-2.00 (m, 1H), 1.69 (d, 1H), 1.50 (d, 1H).

m/e (MultiMode+) 435 [M+H]$^+$

EXAMPLE 11

(S)-4-Amino-N-(1-cyano-2-(4-(3-(3-methoxypropyl)-2-oxo-2,3-dihydrobenzo[d]oxazol-5-yl)phenyl)ethyl)tetrahydro-2H-pyran-4-carboxamide trifluoroacetic acid salt

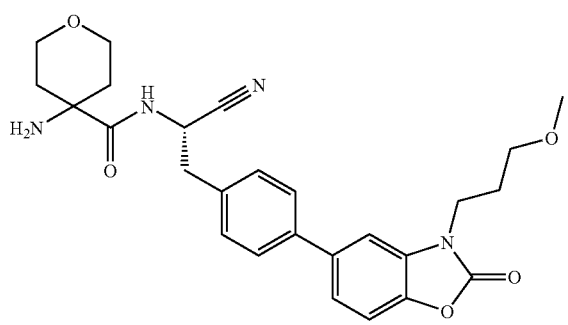

(i) 5-Bromo-3-(3-methoxypropyl)benzo[d]oxazol-2(3H)-one

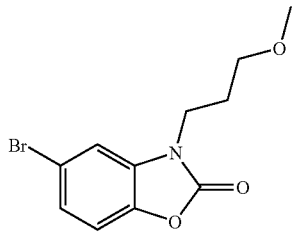

A mixture of 5-bromobenzo[d]oxazol-2(3H)-one (1.1 g), 3-methoxypropyl methanesulfonate (1.297 g) and potassium carbonate (2.131 g) in acetonitrile (25 mL) was heated at 70° C. for 16 h. Water was added and the mixture was extracted with ethyl acetate (3 times). The organic layers were dried (MgSO4), evaporated and purified by flash chromatography (silica, isohexane-acetone (5:1) as eluent) to give the sub-titled compound (1.50 g) as an oil.

m/e (APCI+) 286/288 [M+H]+

(ii) 3-(3-Methoxypropyl)-5-(4,4,5,5-tetramethyl-1,3,2-dioxaborolan-2-yl)benzo[d]oxazol-2(3H)-one

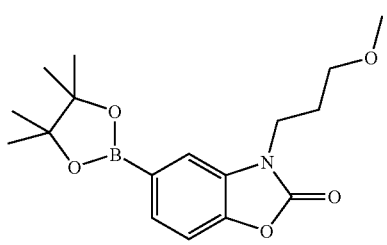

5-Bromo-3-(3-methoxypropyl)benzo[d]oxazol-2(3H)-one (Example 11, step (i), 0.48 g) and 4,4,4',4',5,5,5',5'-octamethyl-2,2'-bi(1,3,2-dioxaborolane) (0.639 g) in acetonitrile (8 mL) and with potassium acetate (0.494 g) was bubbled through with nitrogen and then 1,1 bis(di-tert-butylphosphino)ferrocene palladium dichloride (5 mg) was added and the mixture was heated at 85° C. for 18 h. LCMS showed partial reaction so a further addition of 1,1 bis(di-tert-butylphosphino)ferrocene palladium dichloride was made and the mixture was heated for a further 18 h. The reaction was still incomplete so additional 4,4,4',4',5,5,5',5'-octamethyl-2,2'-bi(1,3,2-dioxaborolane) (200 mg), potassium acetate (0.15 g) and 1,1 bis(di-tert-butylphosphino)ferrocene palladium dichloride (5 mg) was added and the mixture was heated for a further 18 h. The cooled solution was purified by chromatography on silica eluting with 20% ethyl acetate/isohexane as eluent to yield crude product that was re-purified by chromatography on silica eluting with 25% diethyl ether/isohexane to yield the sub-titled compound (234 mg).

m/e (APCI+) 334 [M+H]+

(iii) (S)-tert-Butyl 4-(1-amino-3-(4-(3-(3-methoxypropyl)-2-oxo-2,3-dihydrobenzo[d]oxazol-5-yl)phenyl)-1-oxopropan-2-ylcarbamoyl)tetrahydro-2H-pyran-4-ylcarbamate

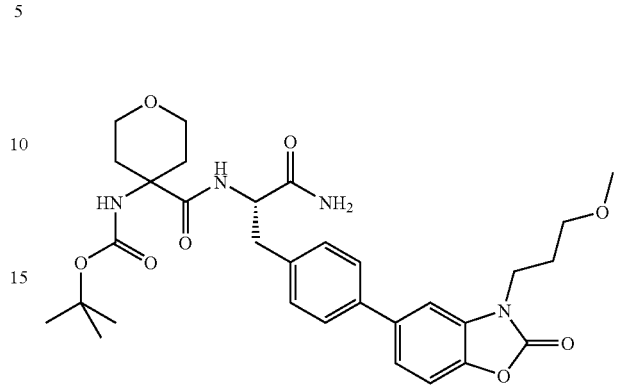

(S)-tert-Butyl 4-(1-amino-3-(4-iodophenyl)-1-oxopropan-2-ylcarbamoyl)tetrahydro-2H-pyran-4-ylcarbamate (Example 1, step (iii), 363 mg) and 3-(3-methoxypropyl)-5-(4,4,5,5-tetramethyl-1,3,2-dioxaborolan-2-yl)benzo[d]oxazol-2(3H)-one (Example 11, step (ii), 234 mg) in acetonitrile (8 mL) were treated with aqueous sodium carbonate (2M, 0.70 mL) and nitrogen was bubbled through the mixture. 1,1 bis(Di-tert-butylphosphino)ferrocene palladium dichloride (5 mg) was added and the mixture was heated at 85° C. for 18 h. The mixture was purified by chromatography on silica eluting with 50-100% ethyl acetate/isohexane to yield the sub-titled compound (151 mg).

m/e (APCI+) 497 [M+2H−BOC]+

(iv) (S)-tert-Butyl 4-(1-cyano-2-(4-(3-(3-methoxypropyl)-2-oxo-2,3-dihydrobenzo[d]oxazol-5-yl)phenyl)ethylcarbamoyl)tetrahydro-2H-pyran-4-ylcarbamate

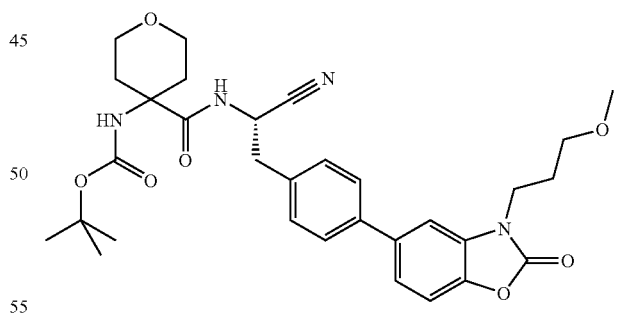

(S)-tert-Butyl 4-(1-amino-3-(4-(3-(3-methoxypropyl)-2-oxo-2,3-dihydrobenzo[d]oxazol-5-yl)phenyl)-1-oxopropan-2-ylcarbamoyl)tetrahydro-2H-pyran-4-ylcarbamate (Example 11, step (iii), 151 mg) in dichloromethane (10 mL) was treated with Burgess' reagent (121 mg) and the mixture was stirred for 18 h at room temperature. The solvent was partially evaporated and the mixture was purified by chromatography on silica eluting with ethyl acetate/isohexane (1:1) to yield the sub-titled compound (137 mg).

m/e (APCI+) 479 [M+2H−BOC]+

(S)-4-Amino-N-(1-cyano-2-(4-(3-(3-methoxypropyl)-2-oxo-2,3-dihydrobenzo[d]oxazol-5-yl)phenyl)ethyl)tetrahydro-2H-pyran-4-carboxamide trifluoroacetic acid salt (S)-tert-Butyl 4-(1-cyano-2-(4-(3-(3-methoxypropyl)-2-oxo-2,3-dihydrobenzo[d]oxazol-5-yl)phenyl)ethylcarbamoyl)tetrahydro-2H-pyran-4-ylcarbamate (Example 11, step (iv), 137 mg) in formic acid (1.5 mL) was stirred at room temperature for 4.5 h. The solvent was evaporated and then methanol was added and the solvent was evaporated. The resulting oil was purified by reversed phase HPLC using methanol/0.1% aqueous TFA on a Waters SunFire column to afford the titled compound as a white solid (55 mg).

$^1$H NMR (399.826 MHz, d$_6$-DMSO) δ 9.23 (d, 1H), 8.44 (s, 3H), 7.67 (d, 2H), 7.55 (s, 1H), 7.44-7.40 (m, 4H), 5.17-5.09 (m, 1H), 3.97-3.90 (m, 2H), 3.71-3.63 (m, 2H), 3.63-3.55 (m, 2H), 3.41-3.36 (m, 2H), 3.31-3.16 (m, 2H), 3.19 (s, 3H), 2.25-2.14 (m, 1H), 2.10-2.00 (m, 1H), 1.95 (quintet, 2H), 1.69 (d, 1H), 1.49 (d, 1H).

m/e (MultiMode+) 479 [M+H]$^+$

EXAMPLE 12

(S)-4'-(2-(4-Aminotetrahydro-2H-pyran-4-carboxamido)-2-cyanoethyl)biphenyl-3-yl methanesulfonate

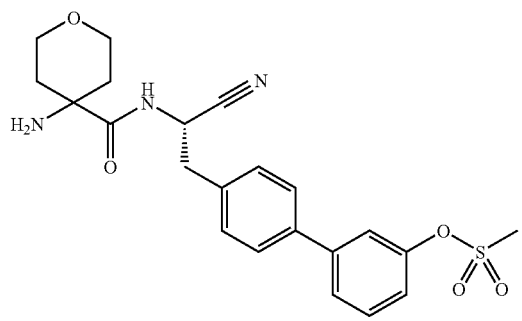

(i) 3-(Methylsulfonyloxy)phenylboronic acid

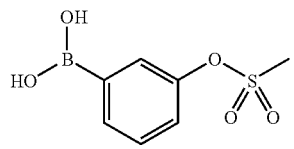

To 3-hydroxyphenylboronic acid (10 g) stirred in pyridine (40 mL) at 0° C. was added methanesulfonyl chloride (8 mL). The reaction mixture was stirred for 1 h at room temperature and then water and ethyl acetate was added. The organic layer was separated and the aqueous layer was extracted with ethyl acetate. The combined organic layers were washed with dilute HCl washed with brine, dried over magnesium sulfate. The resulting solid was recrystallizated from petroleum ether and ethyl acetate to give the sub-titled compound (12 g).

m/e 216 [M+H]$^+$

(ii) (S)-4'-(3-Amino-2-(4-(tert-butoxycarbonylamino)tetrahydro-2H-pyran-4-carboxamido)-3-oxopropyl)biphenyl-3-yl methanesulfonate

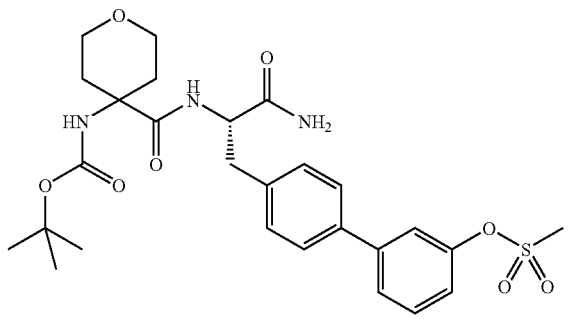

(S)-tert-butyl 4-(1-amino-3-(4-iodophenyl)-1-oxopropan-2-ylcarbamoyl)tetrahydro-2H-pyran-4-ylcarbamate (Example 1, step (iii), 300 mg), 3-(methylsulfonyloxy)phenylboronic acid (Example 12, step (i), 125 mg) and potassium carbonate (240 mg) in acetonitrile (10 mL) and water (5 mL) were stirred and heated at 90° C. under a nitrogen atmosphere with 1,1 bis(di-tert-butylphosphino)ferrocene palladium dichloride (11 mg). After 20 h the reaction was complete and the solvents were removed under reduced pressure. The residue was partitioned between water (100 mL) and ethyl acetate (100 mL), and the organic phase collected and dried over magnesium sulfate. The extract was concentrated to a gum and the crude material purified by chromatography on silica eluting with ethyl acetate to afford the sub-titled is compound (120 mg).

m/e (APCI+) 462 [M+2H−BOC]$^+$

(S)-4'-(2-(4-Aminotetrahydro-2H-pyran-4-carboxamido)-2-cyanoethyl)biphenyl-3-yl methanesulfonate (S)-4'-(3-Amino-2-(4-(tert-butoxycarbonylamino)tetrahydro-2H-pyran-4-carboxamido)-3-oxopropyl)biphenyl-3-ylmethanesulfonate (Example 12, step (ii), 120 mg) in dichloromethane (10 mL) was stirred with Burgess' reagent (76 mg) at room temperature for 18 h. The reaction mixture was concentrated to dryness and the residue treated with formic acid (0.5 mL). The solution was stirred at room temperature for 4 h and then diluted with water (20 mL) and the mixture basified with 0.880 ammonia. The precipitated product was extracted into ethyl acetate (100 mL) and the extract dried over magnesium sulfate. The solvent was evaporated and the residue was purified by reversed phase HPLC eluting with methanol and 0.1% aqueous TFA on a Waters SunFire column to afford the titled compound as a solid (60 mg).

$^1$H NMR (500.303 MHz, D$_2$O) δ 7.41-7.33 (m, 5H), 7.24-7.16 (m, 3H), 5.13 (t, 1H), 3.69-3.62 (m, 1H), 3.60-3.53 (m, 2H), 3.38-3.31 (m, 1H), 3.28-3.21 (m, 4H), 3.10 (dd, 1H), 2.17-2.11 (m, 1H), 2.02-1.95 (m, 1H), 1.85-1.79 (m, 1H), 1.66-1.60 (m, 1H).

m/e (MultiMode+) 444 [M+H]$^+$

EXAMPLE 13

(S)-4-Amino-N-(1-cyano-2-(3',4'-difluorobiphenyl-4-yl)ethyl)tetrahydro-2H-pyran-4-carboxamide trifluoroacetic acid salt

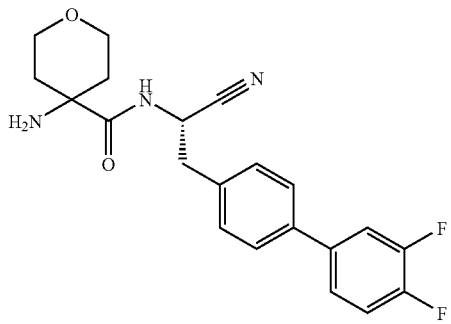

(i) (S)-tert-Butyl 4-(1-amino-3-(3',4'-difluorobiphenyl-4-yl)-1-oxopropan-2-ylcarbamoyl)tetrahydro-2H-pyran-4-ylcarbamate

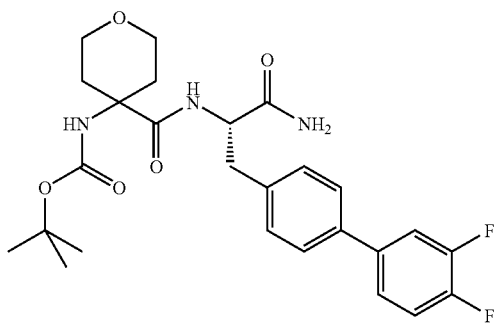

(S)-tert-Butyl 4-(1-amino-3-(4-iodophenyl)-1-oxopropan-2-ylcarbamoyl)tetrahydro-2H-pyran-4-ylcarbamate (Example 1, step (iii), 300 mg) and 3,4-difluorophenylboronic acid (92 mg) in acetonitrile (8 mL) were treated with aqueous sodium carbonate solution (2M, 0.58 mL) and nitrogen was bubbled through the reaction mixture. 1,1 bis(Di-tert-butylphosphino)ferrocene palladium dichloride (8 mg) was added and the mixture was heated at 85° C. for 18 h. The mixture was purified by chromatography on silica eluting with 50-100% ethyl acetate/isohexane as eluent to yield the sub-titled compound (305 mg).

m/e (MultiMode+) 404 [M+2H−BOC]+

(ii) (S)-tert-Butyl 4-(1-cyano-2-(3',4'-difluorobiphenyl-4-yl)ethylcarbamoyl)tetrahydro-2H-pyran-4-ylcarbamate

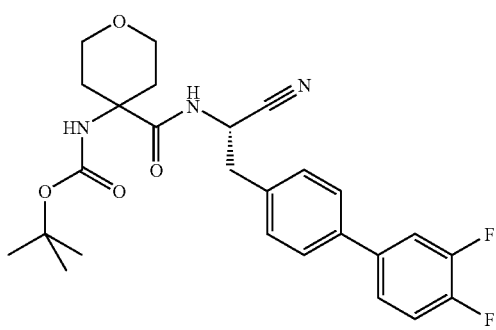

(S)-tert-Butyl 4-(1-amino-3-(3',4'-difluorobiphenyl-4-yl)-1-oxopropan-2-ylcarbamoyl)tetrahydro-2H-pyran-4-ylcarbamate (Example 13, step (i), 305 mg) in dichloromethane (10 mL) was treated with Burgess' reagent (289 mg) and the mixture was stirred at room temperature for 18 h. The solvent was partially evaporated and the residue was purified by chromatography on silica eluting with ethyl acetate/isohexane (1:1) to yield the sub-titled compound (239 mg).

m/e (APCI−) 484 [M−H]−

(S)-4-Amino-N-(1-cyano-2-(3',4'-difluorobiphenyl-4-yl)ethyl)tetrahydro-2H-pyran-4-carboxamide trifluoroacetic acid salt (S)-tert-Butyl 4-(1-cyano-2-(3',4'-difluorobiphenyl-4-yl)ethylcarbamoyl)tetrahydro-2H-pyran-4-ylcarbamate (Example 13, step (ii), 239 mg) in formic acid (1.5 mL) was stirred at room temperature for 3 h. A further 0.5 mL formic acid was added and the mixture was stirred for a further 3 h. Methanol was added and the solvent was evaporated. Methanol was added and the solvent was evaporated a second time. The mixture was purified by reversed phase HPLC using methanol/0.1% aqueous TFA on a Waters SunFire column to afford the sub-titled compound as a solid (127 mg).

$^1$H NMR (399.826 MHz, $d_6$-DMSO) δ 9.23 (d, 1H), 8.45 (s, 3H), 7.80-7.73 (m, 1H), 7.67 (d, 2H), 7.56-7.47 (m, 2H), 7.41 (d, 2H), 5.17-5.09 (m, 1H), 3.71-3.56 (m, 4H), 3.31-3.15 (m, 2H), 2.23-2.14 (m, 1H), 2.09-1.99 (m, 1H), 1.69 (d, 1H), 1.48 (d, 1H).

m/e (MultiMode+) 386 [M+H]+

EXAMPLE 15

(S)-4-Amino-N-(1-cyano-2-(4-(1-oxoisoindolin-5-yl)phenyl)ethyl)tetrahydro-2H-pyran-4-carboxamide

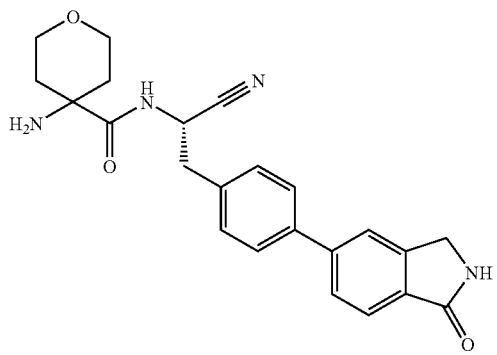

(i) (S)-tert-Butyl 4-(1-cyano-2-(4-iodophenyl)ethylcarbamoyl)tetrahydro-2H-pyran-4-ylcarbamate

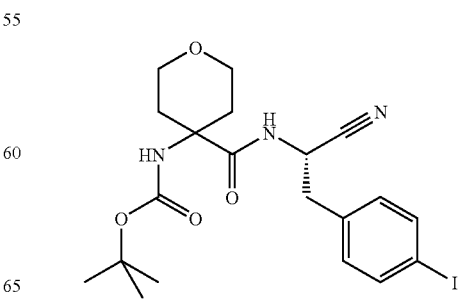

(S)-tert-Butyl 4-(1-amino-3-(4-iodophenyl)-1-oxopropan-2-ylcarbamoyl)tetrahydro-2H-pyran-4-ylcarbamate (Example 1, step (iii), 0.610 g) in dichloromethane (15 mL) was treated with Burgess' reagent (0.365 g) and the mixture was stirred at room temperature for 2 days. The reaction mixture was absorbed onto silica and purified by chromatography on silica eluting with 25% ethyl acetate in isohexane, then 50% ethyl acetate in isohexane to afford the sub-titled compounds (0.402 g) as white crystals.

m/e (APCI+) 400 [M+2H−BOC]+

(ii) (S)-tert-Butyl 4-(1-cyano-2-(4-(1-oxoisoindolin-5-yl)phenyl)ethylcarbamoyl)tetrahydro-2H-pyran-4-ylcarbamate

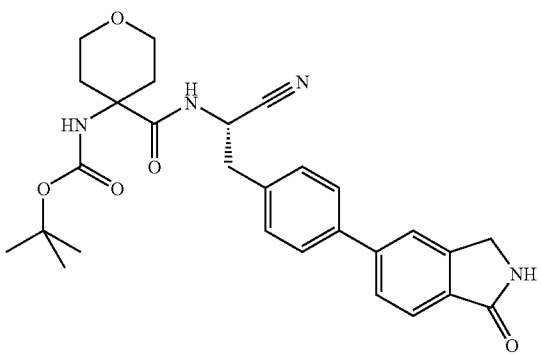

A mixture of (S)-tert-butyl 4-(1-cyano-2-(4-iodophenyl)ethylcarbamoyl)tetrahydro-2H-pyran-4-ylcarbamate (Example 15, step (i), 260 mg), potassium acetate (153 mg) and 5-(4,4,5,5-tetramethyl-1,3,2-dioxaborolan-2-yl)isoindolin-1-one (162 mg) in acetonitrile (10 mL) and water (5 mL) under a nitrogen atmosphere, was treated with 1,1 bis(di-tert-butylphosphino)ferrocene palladium dichloride (10 mg) and the mixture stirred and heated at 90° C. for 18 h. The reaction mixture was cooled to room temperature and diluted with water. The products were extracted into ethyl acetate (2×100 mL) and the combined extracts dried over magnesium sulphate and concentrated to dryness. The residue was purified by chromatography on silica eluting with ethyl acetate to afford the sub-titled compound (160 mg).

m/e (APCI−) 503 [M−H]−

(S)-4-Amino-N-(1-cyano-2-(4-(1-oxoisoindolin-5-yl)phenyl)ethyl)tetrahydro-2H-pyran-4-carboxamide (S)-tert-Butyl 4-(1-cyano-2-(4-(1-oxoisoindolin-5-yl)phenyl)ethylcarbamoyl)tetrahydro-2H-pyran-4-ylcarbamate (Example 15, step (ii), 160 mg) was stirred in formic acid (0.5 mL) at 50° C. for 20 min. The reaction mixture was cooled to room temperature and the mixture diluted with water (20 mL). The solution was basified with 0.880 ammonia and extracted into ethyl acetate (100 mL). The extract was dried over magnesium sulfate and concentrated. The crude product was purified by chromatography on silica using methanol/ethyl acetate (1/9) to afford the titled compound as a solid (70 mg).

¹H NMR (399.826 MHz, d₆-DMSO) δ 8.55 (s, 1H), 7.84 (s, 1H), 7.77-7.64 (m, 4H), 7.41 (d, 2H), 5.01 (t, 1H), 4.42 (s, 2H), 3.68-3.53 (m, 3H), 3.50-3.42 (m, 1H), 3.25-3.17 (m, 2H), 1.94-1.85 (m, 1H), 1.78-1.70 (m, 1H), 1.26-1.09 (m, 2H).

m/e (MultiMode+) 405 [M+H]+

EXAMPLE 16

(S)-4-Amino-N-{cyano-2-[4-(2-methyl-1,1-dioxido-2,3-dihydro-1,2-benzisothiazol-5-yl)phenyl]ethyl}tetrahydro-2H-pyran-4-carboxamide trifluoroacetic acid salt

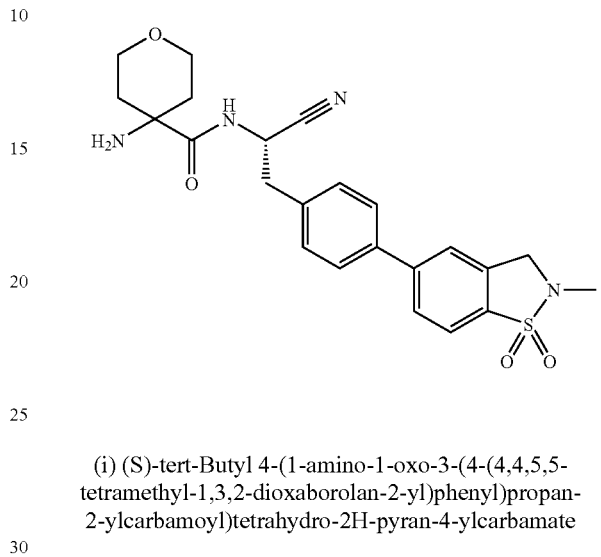

(i) (S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate

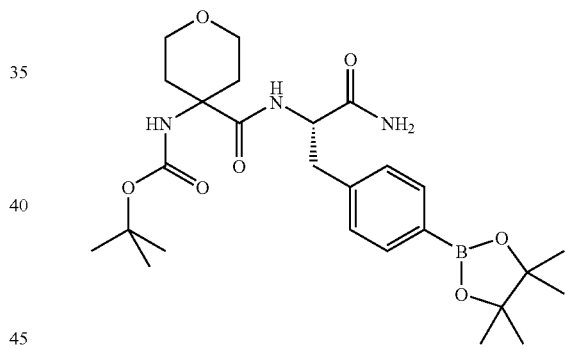

4,4,4',4',5,5,5',5'-Octamethyl-2,2'-bi(1,3,2-dioxaborolane) (1.576 g), (S)-tert-butyl 4-(1-amino-3-(4-iodophenyl)-1-oxopropan-2-ylcarbamoyl)tetrahydro-2H-pyran-4-ylcarbamate (Example 1, step (iii), 2.47 g) and potassium acetate (1.406 g) in a mixture of acetonitrile (50 mL) and water (8 mL) under a nitrogen atmosphere was treated with 1,1 bis(bi-tert-butylphosphino)ferrocene palladium dichloride (50 mg) and the mixture stirred and heated under reflux for 24 h. Further potassium acetate (0.352 g), 4,4,4',4',5,5,5',5'-octamethyl-2,2'-bi(1,3,2-dioxaborolane) (0.394 g) and 1,1 bis(bi-tert-butylphosphino)ferrocene palladium dichloride (50 mg) were added and heating continued for 24 h. The reaction was evaporated in vacuo and the residue partitioned between ethyl acetate (200 mL) and water (200 mL). The organic extracts were dried over magnesium sulfate, evaporated in vacuo and the crude product purified by flash silica chromatography eluting with ethyl acetate. Pure fractions were evaporated to dryness to afford the sub-titled compound (1.71 g).

¹H NMR (399.824 MHz, CDCl₃) δ 7.74 (d, 2H), 7.21 (d, 2H), 6.82 (s, 1H), 6.43 (d, 1H), 5.32 (s, 1H), 4.92 (s, 1H), 4.73

(q, 1H), 3.87 (dt, 1H), 3.68 (dt, 1H), 3.59-3.48 (m, 2H), 3.30-3.12 (m, 2H), 2.35-2.25 (m, 1H), 1.91-1.77 (m, 2H), 1.56-1.49 (m, 1H), 1.33 (d, 12H), 1.24 (s, 9H).

m/e (APCI+) 518 [M+H]+

(ii) N-α-({4-[(tert-Butoxycarbonyl)amino]tetrahydro-2H-pyran-4-yl}carbonyl)-4-(2-methyl-1,1-dioxido-2,3-dihydro-1,2-benzisothiazol-5-yl)-L-phenylalaninamide

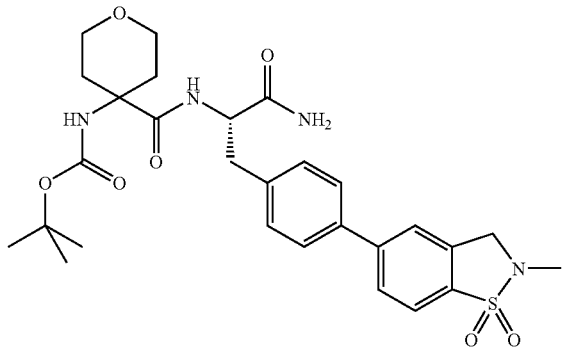

(S)-tert-butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 280 mg) and 5-bromo-2-methyl-2,3-dihydro-1,2-benzisothiazole 1,1-dioxide (170 mg) in acetonitrile (4 mL) were treated with 1,1 bis(bi-tert-butylphosphino)ferrocene palladium dichloride (18 mg) and the mixture was stirred at room temperature for 15 min. An aqueous solution of potassium carbonate (2M aqueous solution) (0.54 mL) was added and the mixture was stirred for 7 h at 80° C. The reaction mixture was extracted with ethyl acetate, dried and evaporated to afford the sub-titled compound (280 mg).

m/e (APCI+) 473 [M+2H−BOC]+

(iii) (S)-tert-Butyl [4-({1-cyano-2-[4-(2-methyl-1,1-dioxido-2,3-dihydro-1,2-benzisothiazol-5-yl)phenyl]ethyl}carbamoyl)tetrahydro-2H-pyran-4-yl]carbamate

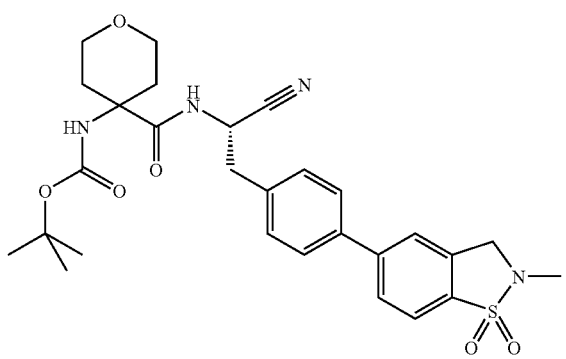

To N-α-({4-[(tert-butoxycarbonyl)amino]tetrahydro-2H-pyran-4-yl}carbonyl)-4-(2-methyl-1,1-dioxido-2,3-dihydro-1,2-benzisothiazol-5-yl)-L-phenylalaninamide (368 mg) in dichloromethane (3 mL) was added Burgess' reagent (306 mg) and the mixture was stirred at room temperature for 18 h.

The reaction mixture was poured into water (10 mL) and extracted with dichloromethane (3×5 mL). The combined organic extracts were dried over magnesium sulfate and evaporated to afford the sub-titled compound (268 mg).

m/e (APCI−) 553 [M−H]−

(S)-4-Amino-N-{cyano-2-[4-(2-methyl-1,1-dioxido-2,3-dihydro-1,2-benzisothiazol-5-yl)phenyl]ethyl}tetrahydro-2H-pyran-4-carboxamide trifluoroacetic acid salt To (S)-tert-butyl [4-({1-cyano-2-[4-(2-methyl-1,1-dioxido-2,3-dihydro-1,2-benzisothiazol-5-yl)phenyl]ethyl}carbamoyl)tetrahydro-2H-pyran-4-yl]carbamate (Example 16, step (iii), 268 mg) was added formic acid (2 mL) and the mixture stirred for 4 h at room temperature. The mixture was basified to pH~8 with 0.880 ammonia and then extracted with ethyl acetate (3×25 mL). The combined organic extracts were dried over magnesium sulfate and evaporated to afford an oil which was further purified by preparative HPLC using a Waters SunFire column and eluting with methanol in 0.1% aqueous TFA to afford the titled compound (95 mg).

1H NMR (399.826 MHz, d6-DMSO) δ 9.25 (d, 1H), 8.47 (s, 3H), 7.94 (d, 1H), 7.89-7.84 (m, 2H), 7.72 (d, 2H), 7.46 (d, 2H), 5.15 (q, 1H), 4.46 (s, 2H), 3.70-3.63 (m, 2H), 3.62-3.55 (m, 2H), 3.34-3.17 (m, 2H), 2.84 (s, 3H), 2.24-2.13 (m, 1H), 2.09-1.98 (m, 1H), 1.69 (d, 1H), 1.49 (d, 1H).

m/e (MultiMode+) 455 [M+H]+

EXAMPLE 17

(S)-4-amino-N-(1-cyano-2-(4-(3-methyl-2-oxo-2,3-dihydrobenzo[d]oxazol-5-yl)phenyl)ethyl)tetrahydro-2H-pyran-4-carboxamide

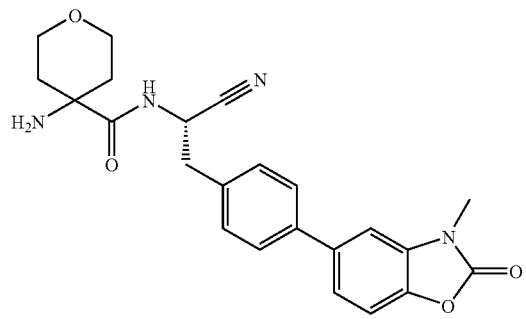

(i) (S)-tert-Butyl 4-(1-amino-3-(4-(3-methyl-2-oxo-2,3-dihydrobenzo[d]oxazol-5-yl)phenyl)-1-oxopropan-2-ylcarbamoyl)tetrahydro-2H-pyran-4-ylcarbamate

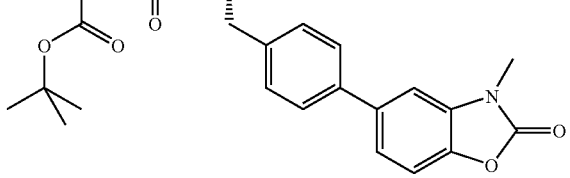

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 224 mg) in acetonitrile (10 mL) under nitrogen was treated with 5-bromo-3-methylbenzo[d]oxazol-2(3H)-one (99 mg) followed by an aqueous solution of potassium carbonate (2M, 0.433 mL) and 1,1 bis(bi-tert-butylphosphino)ferrocene palladium dichloride (6 mg). The reaction mixture was stirred at 75° C. for 18 h and then evaporated to an oil, dissolved in dichloromethane and absorbed onto silica. Purification by chromatography on silica eluting with 50% ethyl acetate in isohexane and then 100% ethyl acetate afforded the sub-titled compound (150 mg).

m/e (APCI+) 439 [M+2H–BOC]+

(ii) (S)-tert-Butyl 4-(1-cyano-2-(4-(3-methyl-2-oxo-2,3-dihydrobenzo[d]oxazol-5-yl)phenyl)ethylcarbamoyl)tetrahydro-2H-pyran-4-ylcarbamate

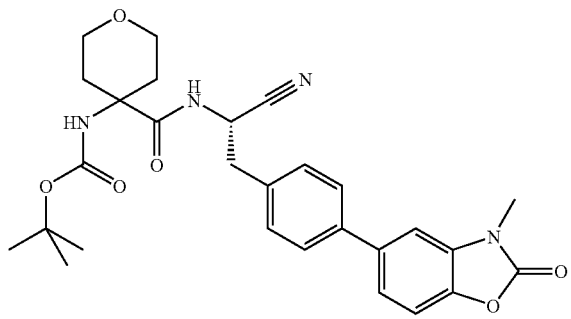

(S)-tert-Butyl 4-(1-amino-3-(4-(3-methyl-2-oxo-2,3-dihydrobenzo[d]oxazol-5-yl)phenyl)-1-oxopropan-2-ylcarbamoyl)tetrahydro-2H-pyran-4-ylcarbamate (Example 17, step (i), 150 mg) in dichloromethane (15 mL) was treated with Burgess' reagent (100 mg) and stirred for 18 h. The reaction mixture was evaporated to a residue (145 mg) and used crude in the following step.

m/e (APCI+) 421 [M+2H–BOC]+

(S)-4-Amino-N-(1-cyano-2-(4-(3-methyl-2-oxo-2,3-dihydrobenzo[d]oxazol-5-yl)phenyl)ethyl)tetrahydro-2H-pyran-4-carboxamide (S)-tert-Butyl 4-(1-cyano-2-(4-(3-methyl-2-oxo-2,3-dihydrobenzo[d]oxazol-5-yl)phenyl)ethylcarbamoyl)tetrahydro-2H-pyran-4-ylcarbamate (Example 17, step (ii), 145 mg) (crude mixture) was dissolved in formic acid (3 mL) and the mixture stirred at room temperature for 18 h. The mixture was evaporated to dryness, dissolved in methanol (10 mL), re-evaporated to dryness, dissolved in methanol/acetonitrile 50:50 (4 mL) and purified on reversed phase HPLC eluting with methanol in 0.1% aqueous TFA on a Water's SunFire column. The material was converted to free base by evaporating the relevant fractions, dissolving in ethyl acetate (20 mL) and shaking with saturated aqueous sodium bicarbonate solution (20 mL). The sodium bicarbonate was further extracted with ethyl acetate (20 mL). The combined extracts were dried over magnesium sulfate and evaporated to afford the titled compound (47 mg).

$^1$H NMR (399.824 MHz, CDCl$_3$) δ 8.26 (d, 1H), 7.55 (dt, 2H), 7.36 (d, 2H), 7.31 (dd, 1H), 7.25 (d, 1H), 7.13 (d, 1H), 5.13 (d, 1H), 3.89 (m, 2H), 3.61 (m, 2H), 3.45 (s, 3H), 3.15 (d, 2H), 2.30 (ddd, 1H), 2.19 (ddd, 1H), 1.53 (s, 2H), 1.30 (dq, 1H), 1.21 (dq, 1H).

m/e (APCI+) 421 [M+H]+

EXAMPLE 18

(S)-4-Amino-N-(1-cyano-2-(3'-cyano-4'-methylbiphenyl-4-yl)ethyl)tetrahydro-2H-pyran-4-carboxamide trifluoroacetic acid salt

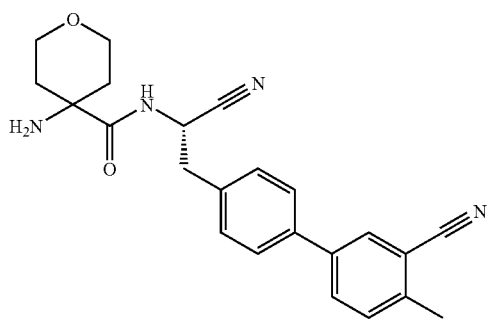

(i) (S)-tert-Butyl 4-(1-amino-3-(3'-cyano-4'-methylbiphenyl-4-yl)-1-oxopropan-2-ylcarbamoyl)tetrahydro-2H-pyran-4-ylcarbamate

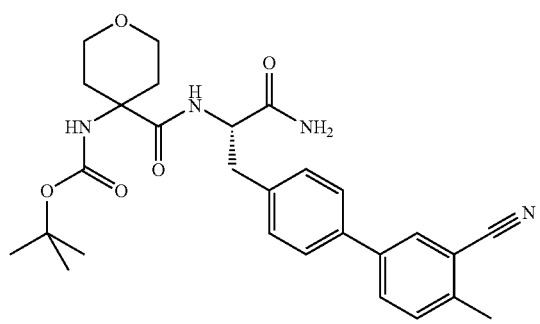

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 200 mg) and 5-bromo-2-methylbenzonitrile (80 mg) in acetonitrile (8 mL) were treated with an aqueous solution of sodium carbonate (2M, 0.387 mL) and nitrogen was bubbled through the mixture. 1,1 bis(Di-tert-butylphosphino)ferrocene palladium dichloride (5 mg) was added and the mixture was heated at 85° C. for 18 h. The mixture was concentrated and purified by chromatography on silica eluting with 50 to 100% ethyl acetate/isohexane to afford the sub-titled compound (154 mg).

m/e (APCI–) 505 [M–H]–

(ii) (S)-tert-Butyl 4-(1-cyano-2-(3'-cyano-4'-methyl-biphenyl-4-yl)ethylcarbamoyl)tetrahydro-2H-pyran-4-ylcarbamate

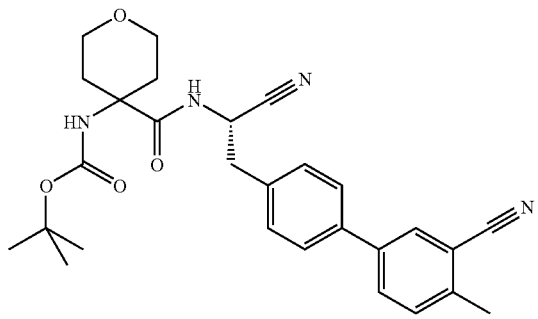

(S)-tert-Butyl 4-(1-amino-3-(3'-cyano-4'-methylbiphenyl-4-yl)-1-oxopropan-2-ylcarbamoyl)tetrahydro-2H-pyran-4-ylcarbamate (Example 18, step (i), 154 mg) in dichloromethane (8 mL) was treated with Burgess' reagent (145 mg) and the mixture was stirred at room temperature for 18 h. The solvent was partially evaporated and the mixture was purified by chromatography on silica eluting with ethyl acetate/isohexane (1:1) to afford the sub-titled compound (127 mg).

m/e (APCI+) 389 [M+2H−BOC]+

(S)-4-Amino-N-(1-cyano-2-(3'-cyano-4'-methylbiphenyl-4-yl)ethyl)tetrahydro-2H-pyran-4-carboxamide trifluoroacetic acid salt (S)-tert-Butyl 4-(1-cyano-2-(3'-cyano-4'-methylbiphenyl-4-yl)ethylcarbamoyl)tetrahydro-2H-pyran-4-ylcarbamate (Example 18, step (ii), 127 mg) in formic acid (1.5 mL) was stirred at room temperature for 5 h. The reaction mixture was evaporated and then methanol was added and evaporated. Purification by reversed phased HPLC using methanol/0.1% aqueous TFA on a Water's SunFire column afforded the titled compound (61 mg).

$^1$H NMR (399.825 MHz, CD$_3$OD) δ 7.88 (d, 1H), 7.79 (dd, 1H), 7.63-7.59 (m, 2H), 7.47 (d, 1H), 7.39 (d, 2H), 5.19 (dd, 1H), 3.85-3.78 (m, 1H), 3.73-3.54 (m, 3H), 3.36-3.16 (m, 2H), 2.54 (s, 3H), 2.31-2.22 (m, 1H), 2.15-2.06 (m, 1H), 1.79-1.71 (m, 1H), 1.59-1.52 (m, 1H).

m/e (MultiMode+) 389 [M+H]+

EXAMPLE 19

(S)-4-Amino-N-(1-cyano-2-(4'-cyano-3'-methylbiphenyl-4-yl)ethyl)tetrahydro-2H-pyran-4-carboxamide trifluoroacetic acid salt

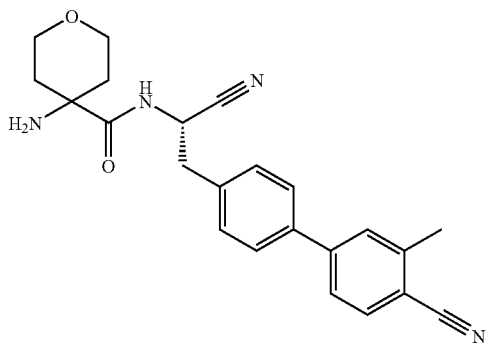

(i) (S)-tert-Butyl 4-(1-amino-3-(4'-cyano-3'-methyl-biphenyl-4-yl)-1-oxopropan-2-ylcarbamoyl)tetrahydro-2H-pyran-4-ylcarbamate

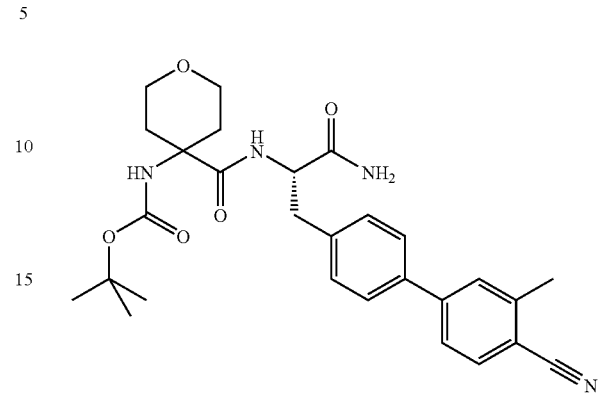

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 180 mg) and 4-bromo-2-methylbenzonitrile (72 mg) in acetonitrile (8 mL) were treated with an aqueous solution of sodium carbonate (2M, 0.348 mL) and nitrogen was bubbled through the mixture. 1,1 bis(Di-tert-butylphosphino)ferrocene palladium dichloride (5 mg) was added and the mixture was heated at 85° C. for 18 h. The mixture was concentrated and purified by chromatography on silica eluting with 50 to 100% ethyl acetate/isohexane to afford the sub-titled compound (127 mg).

m/e (APCI−) 505 [M−H]−

(ii) (S)-tert-Butyl 4-(1-cyano-2-(4'-cyano-3'-methyl-biphenyl-4-yl)ethylcarbamoyl)tetrahydro-2H-pyran-4-ylcarbamate

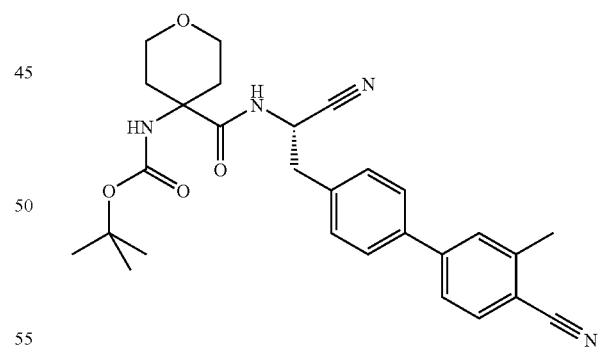

(S)-tert-butyl 4-(1-amino-3-(4'-cyano-3'-methylbiphenyl-4-yl)-1-oxopropan-2-ylcarbamoyl)tetrahydro-2H-pyran-4-ylcarbamate (Example 19, step (i), 127 mg) in dichloromethane (8 mL) was treated with Burgess' reagent (119 mg) and the mixture was stirred at room temperature for 18 h. The solvent was partially evaporated and the mixture was purified by chromatography on silica eluting with ethyl acetate/isohexane (1:1) to afford the sub-titled compound (105 mg).

m/e (APCI−) 487 [M−H]−

(S)-4-Amino-N-(1-cyano-2-(4'-cyano-3'-methylbiphenyl-4-yl)ethyl)tetrahydro-2H-pyran-4-carboxamide trifluoroacetic acid salt (S)-tert-Butyl 4-(1-cyano-2-(4'-cyano-3'-methylbiphenyl-4-yl)ethylcarbamoyl)tetrahydro-2H-pyran-4-ylcarbamate (Example 19, step (ii), 105 mg) in formic acid (1.5 mL) was stirred at room temperature for 5 h. The reaction mixture was evaporated and then methanol was added and evaporated. Purification by reversed phased HPLC using methanol/0.1% aqueous TFA on a Water's SunFire column afforded the titled compound (31 mg).

$^1$H NMR (399.826 MHz, d$_6$-DMSO) δ 9.23 (d, 1H), 8.44 (s, 3H), 7.84 (d, 1H), 7.79 (s, 1H), 7.73 (d, 2H), 7.67 (dd, 1H), 7.45 (d, 2H), 5.18-5.11 (m, 1H), 3.70-3.63 (m, 2H), 3.62-3.55 (m, 2H), 3.33-3.16 (m, 2H), 2.55 (s, 3H), 2.24-2.13 (m, 1H), 2.09-1.98 (m, 1H), 1.68 (d, 1H), 1.48 (d, 1H).

m/e (MultiMode+) 389 [M+H]$^+$

EXAMPLE 20

(S)-4-Amino-N-(1-cyano-2-(4'-methoxybiphenyl-4-yl)ethyl)tetrahydro-2H-pyran-4-carboxamide

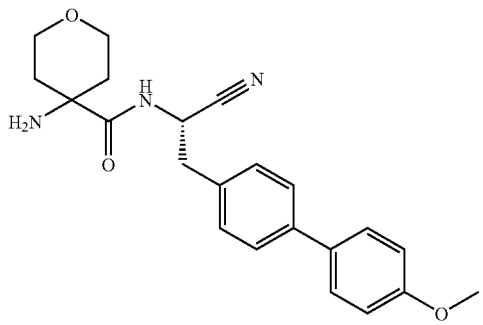

(i) (S)-tert-Butyl 4-(1-cyano-2-(4'-methoxybiphenyl-4-yl)ethylcarbamoyl)tetrahydro-2H-pyran-4-ylcarbamate

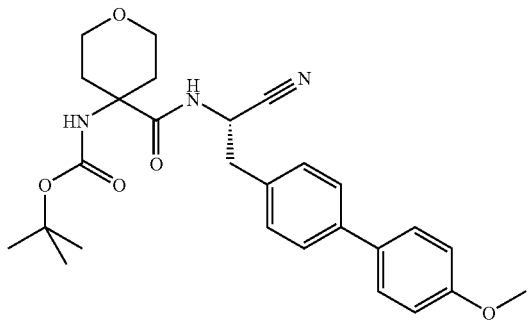

(S)-tert-Butyl 4-(1-cyano-2-(4-iodophenyl)ethylcarbamoyl)tetrahydro-2H-pyran-4-ylcarbamate (Example 15, step (i), 317 mg) in acetonitrile (5 mL) under nitrogen was treated with 4-methoxyphenylboronic acid (96 mg) followed by an aqueous solution of potassium acetate (2M, 0.65 mL) and 1,1 bis(bi-tert-butylphosphino)ferrocene palladium dichloride (8 mg). The reaction mixture was stirred at 75° C. for 18 h and then evaporated, dissolved in dichloromethane and absorbed onto silica. Purification by chromatography on silica eluting with 50% ethyl acetate in isohexane and then 100% ethyl acetate afforded the sub-titled compound as a solid (120 mg).

m/e (APCI+) 380 [M+2H−BOC]$^+$

(S)-4-Amino-N-(1-cyano-2-(4'-methoxybiphenyl-4-yl)ethyl)tetrahydro-2H-pyran-4-carboxamide (S)-tert-Butyl 4-(1-cyano-2-(4'-methoxybiphenyl-4-yl)ethylcarbamoyl)tetrahydro-2H-pyran-4-ylcarbamate (Example 20, step (i), 120 mg) was dissolved in formic acid (3 mL) and the mixture stirred at room temperature for 3 h. The mixture was evaporated to dryness, dissolved in methanol (10 mL), re-evaporated to dryness, dissolved in methanol (5.5 mL) and purified on reversed phase HPLC eluting with methanol in 0.1% aqueous TFA on a Water's SunFire column. The material was converted to free base by evaporating the relevant fractions, dissolving in ethyl acetate (20 mL) and extracted with saturated sodium bicarbonate solution (20 mL). The sodium bicarbonate solution was further extracted with ethyl acetate (20 mL). The combined ethyl acetate extracts were dried and evaporated to afford the titled compound (91 mg).

$^1$H NMR (399.826 MHz, d$_6$-DMSO) δ 7.56 (d, 2H), 7.53 (d, 2H), 7.31 (d, 2H), 6.98 (d, 2H), 4.95 (t, 1H), 3.76 (s, 3H), 3.63-3.51 (m, 3H), 3.44 (dt, 1H), 3.19-3.08 (m, 2H), 1.87 (ddd, 1H), 1.73 (ddd, 1H), 1.18 (dq, 1H), 1.11 (dq, 1H).

m/e (APCI+) 380 [M+H]$^+$

EXAMPLE 21

(S)-4-Amino-N-(1-cyano-2-(4-(1-methyl-2-oxoindolin-6-yl)phenyl)ethyl)tetrahydro-2H-pyran-4-carboxamide

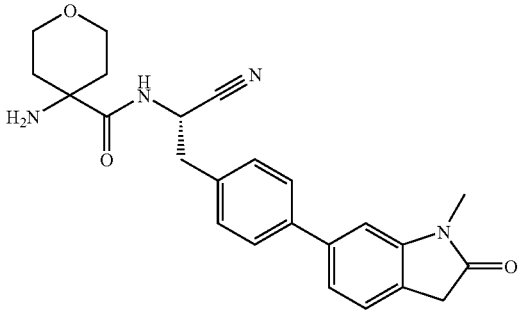

(i) (S)-tert-Butyl 4-(1-amino-3-(4-(1-methyl-2-oxoindolin-6-yl)phenyl)-1-oxopropan-2-ylcarbamoyl)tetrahydro-2H-pyran-4-ylcarbamate

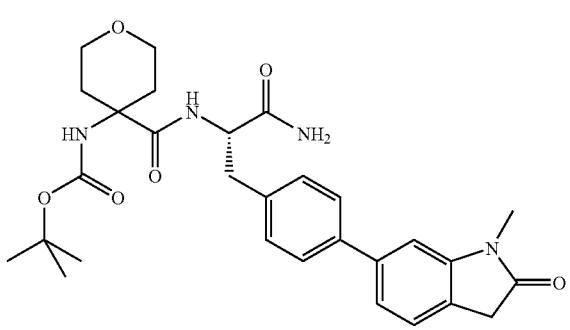

A solution of (S)-tert-butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 200 mg) and 6-bromo-1-methylindolin-2-one (87 mg) in acetonitrile (5 mL) was treated with potassium carbonate (107 mg) and purged with nitrogen. 1,1 bis(Di-tert-butylphosphino)ferrocene palladium dichloride (15 mg) was added and the reaction stirred is under reflux under nitrogen for 4 h and then evaporated in vacuo. The residue was partitioned between water (40 mL) and ethyl acetate (40 mL). The aqueous was further extracted with ethyl acetate (40 mL) and the combined organic extracts were dried over magnesium sulfate and evaporated in vacuo. The crude product was purified by flash silica chromatography eluting with ethyl acetate. Pure fractions were evaporated to dryness to afford the sub-titled compound (45 mg).

$^1$H NMR (399.824 MHz, CDCl$_3$) δ 7.54 (d, 2H), 7.32-7.28 (m, 3H), 7.22 (d, 1H), 6.97 (s, 1H), 6.88-6.80 (m, 1H), 6.49 (d, 1H), 5.27 (s, 1H), 4.90 (s, 1H), 4.80 (q, 1H), 3.89-3.82 (m, 1H), 3.69-3.62 (m, 1H), 3.60-3.48 (m, 4H), 3.32-3.18 (m, 5H), 2.33-2.24 (m, 1H), 1.92-1.76 (m, 2H), 1.35 (s, 9H).

m/e (Multimode+) 437 [M+2H−BOC]$^+$ (ii) (S)-tert-Butyl 4-(1-cyano-2-(4-(1-methyl-2-oxoindolin-6-yl)phenyl)ethylcarbamoyl)tetrahydro-2H-pyran-4-ylcarbamate

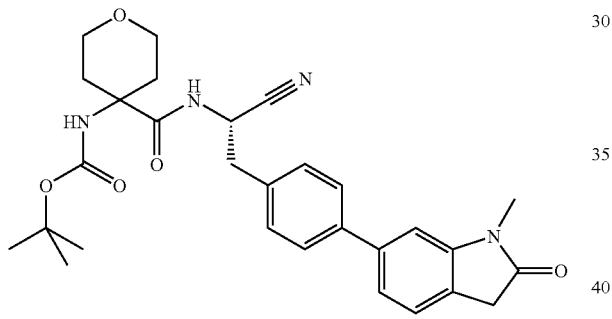

A solution of (S)-tert-butyl 4-(1-amino-3-(4-(1-methyl-2-oxoindolin-6-yl)phenyl)-1-oxopropan-2-ylcarbamoyl)tetrahydro-2H-pyran-4-ylcarbamate (Example 21, step (i), 44 mg) in dichloromethane (5 mL) was treated with Burgess' reagent (25 mg) and stirred at room temperature for 24 h. The reaction was diluted with dichloromethane (50 mL) and washed with water (50 mL). The combined organic extracts were dried over magnesium sulfate and evaporated in vacuo to the sub-titled compound (35 mg).

m/e (Multimode−) 517 [M−H]$^-$ (S)-4-Amino-N-(1-cyano-2-(4-(1-methyl-2-oxoindolin-6-yl)phenyl)ethyl)tetrahydro-2H-pyran-4-carboxamide A solution of (S)-tert-butyl 4-(1-cyano-2-(4-(1-methyl-2-oxoindolin-6-yl)phenyl)ethylcarbamoyl)tetrahydro-2H-pyran-4-ylcarbamate (Example 21, step (ii), 35 mg) in formic acid (5 mL) was stirred at 50° C. for 30 min. The reaction mixture was poured into ice/water (50 mL) and basified to pH 8 with 0.880 aqueous ammonia solution. The mixture was extracted with ethyl acetate (2×40 mL) and the organics were dried over sodium sulfate and evaporated in vacuo. The crude product was purified by reversed phase HPLC on a Waters' Sunfire column using methanol and aqueous 0.1% trifluoroacetic acid as eluent. The fractions containing the desired compound were evaporated to dryness to afford product which was further purified by chromatography on silica eluting with 3% 2M methanolic ammonia in dichloromethane. Pure fractions were evaporated to dryness to afford the titled compound (10 mg).

$^1$H NMR (399.826 MHz, d$_6$-DMSO) δ 7.71-7.61 (m, 2H), 7.43-7.20 (m, 5H), 5.05-4.94 (m, 1H), 3.69-3.53 (m, 5H), 3.53-3.44 (m, 1H), 3.32 (s, 3H), 3.24-3.14 (m, 5H), 1.96-1.84 (m, 1H), 1.83-1.70 (m, 1H), 1.31-1.10 (m, 2H).

m/e (MultiMode+) 419 [M+H]$^+$

EXAMPLE 22

(S)-4-Amino-N-(1-cyano-2-(3'-cyano-4'-fluorobiphenyl-4-yl)ethyl)tetrahydro-2H-pyran-4-carboxamide

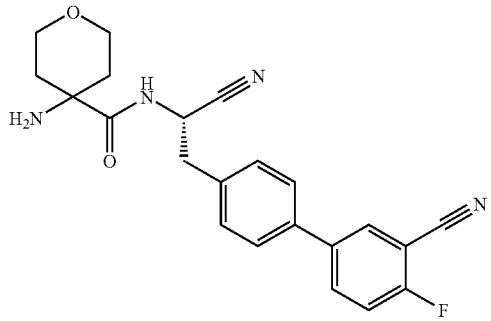

(i) (S)-tert-Butyl 4-(1-amino-3-(3'-cyano-4'-fluorobiphenyl-4-yl)-1-oxopropan-2-ylcarbamoyl)tetrahydro-2H-pyran-4-ylcarbamate

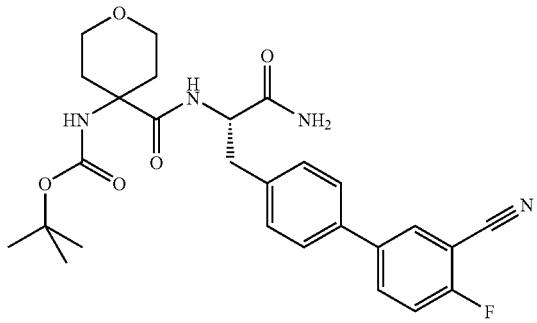

(S)-tert-Butyl 4-(1-amino-3-(4-iodophenyl)-1-oxopropan-2-ylcarbamoyl)tetrahydro-2H-pyran-4-ylcarbamate (Example 1, step (iii), 346 mg) in acetonitrile (10 mL) under nitrogen was treated with 3-cyano-4-fluorophenylboronic acid (110 mg) followed by aqueous potassium carbonate solution (2M, 0.67 mL) and 1,1 bis(di-tert-butylphosphino)ferrocene palladium dichloride (9 mg). The mixture was stirred at 75° C. for 18 h. The reaction mixture was evaporated, dissolved in dichloromethane, absorbed onto silica and purified by chromatography on silica eluting with 50% ethyl acetate in isohexane, then 100% ethyl acetate to afford the titled compound (366 mg).

m/e (APCI+) 411 [M+2H−BOC]$^+$ (ii) (S)-tert-Butyl 4-(1-cyano-2-(4'-cyanobiphenyl-4-yl)ethylcarbamoyl)tetrahydro-2H-pyran-4-ylcarbamate

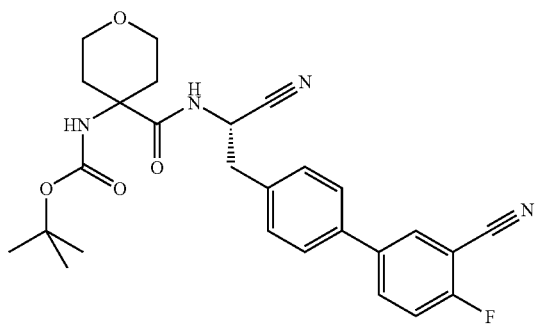

(S)-tert-Butyl 4-(1-amino-3-(3'-cyano-4'-fluorobiphenyl-4-yl)-1-oxopropan-2-ylcarbamoyl)tetrahydro-2H-pyran-4-ylcarbamate (Example 22, step (i), 366 mg) in dichloromethane (5 mL) was treated with Burgess' reagent (205 mg) and the mixture was stirred at room temperature for 18 h. The reaction mixture was evaporated to afford the sub-titled compound as a crude mixture (336 mg).
m/e (APCI+) 393 [M+2H−BOC]+

(S)-4-Amino-N-(1-cyano-2-(3'-cyano-4'-fluorobiphenyl-4-yl)ethyl)tetrahydro-2H-pyran-4-carboxamide (S)-tert-Butyl 4-(1-cyano-2-(3'-cyano-4'-fluorobiphenyl-4-yl)ethylcarbamoyl)tetrahydro-2H-pyran-4-ylcarbamate (Example 22, step (ii), 353 mg) was dissolved in formic acid (2.5 mL) and the reaction mixture stirred at room temperature for 3 h. The reaction mixture was evaporated to dryness, dissolved in methanol (10 mL), re-evaporated to dryness, dissolved in methanol (5.5 mL) and purified on reversed phase HPLC eluting with methanol in 0.1% aqueous TFA on a Water's SunFire column. The material was converted to free base by evaporating the relevant fractions, dissolving the residue in ethyl acetate (20 mL) and washing with saturated sodium bicarbonate solution (20 mL). The sodium bicarbonate solution was re-extracted with ethyl acetate (20 mL). The combined organic extracts were dried and evaporated to afford the titled compound (209 mg).
$^1$H NMR (399.824 MHz, CDCl$_3$) δ 8.27 (d, 1H), 7.80 (m, 1H), 7.77 (dd, 1H), 7.51 (d, 2H), 7.39 (d, 2H), 7.30 (td, 1H), 5.12 (dt, 1H), 3.90 (ddt, 1H), 3.66-3.56 (m, 2H), 3.20-3.10 (m, 2H), 2.30 (ddd, 1H), 2.20 (ddd, 1H), 1.51 (s, 2H), 1.30 (dq, 1H), 1.21 (dq, 1H).
m/e (MultiMode+) 393 [M+H]+

EXAMPLE 23

(S)-4-Amino-N-(1-cyano-2-(3'-(methylsulfonyl)biphenyl-4-yl)ethyl)tetrahydro-2H-pyran-4-carboxamide trifluoroacetic acid salt

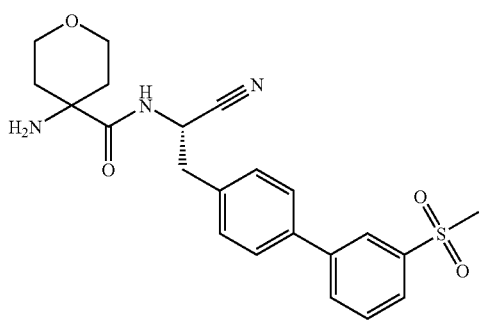

(i) (S)-tert-Butyl 4-(1-amino-3-(3'-(methylsulfonyl)biphenyl-4-yl)-1-oxopropan-2-ylcarbamoyl)tetrahydro-2H-pyran-4-ylcarbamate

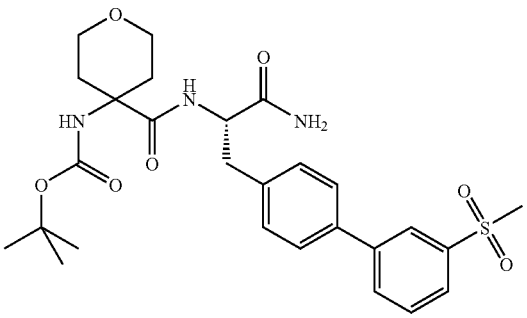

(S)-tert-Butyl 4-(1-amino-3-(4-iodophenyl)-1-oxopropan-2-ylcarbamoyl)tetrahydro-2H-pyran-4-ylcarbamate (Example 1, step (iii), 300 mg) and 3-(methylsulfonyl)phenylboronic acid (122 mg) in acetonitrile (8 mL) were treated with an aqueous solution of sodium carbonate (2M, 0.58 mL) and nitrogen was bubbled through the mixture. 1,1 bis(Di-tert-butylphosphino)ferrocene palladium dichloride (5 mg) was added and the reaction mixture was heated at 85° C. for 18 h. The mixture was purified by chromatography on silica eluting with 50-100% ethyl acetate/isohexane as eluent to yield the sub-titled compound (320 mg).
m/e (APCI−) 544 [M−H]−

(ii) (S)-tert-Butyl 4-(1-cyano-2-(3'-(methylsulfonyl)biphenyl-4-yl)ethylcarbamoyl)tetrahydro-2H-pyran-4-ylcarbamate

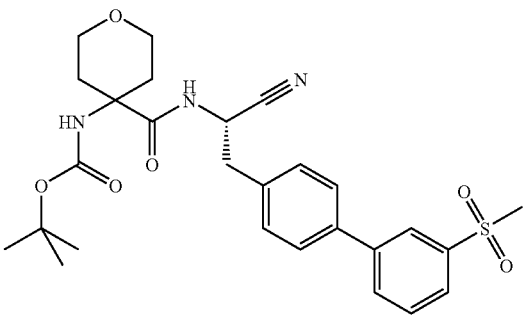

(S)-tert-Butyl 4-(1-amino-3-(3'-(methylsulfonyl)biphenyl-4-yl)-1-oxopropan-2-ylcarbamoyl)tetrahydro-2H-pyran-4-ylcarbamate (Example 23, step (i), 320 mg) in dichloromethane (8 mL) was treated with Burgess' reagent (280 mg) and the mixture was stirred at room temperature for 18 h. The solvent was partially evaporated and the mixture was purified by chromatography on silica eluting with 1:1 ethyl acetate/isohexane as eluent to afford the sub-titled compound (230 mg).
m/e (APCI−) 526 [M−H]−

(S)-4-Amino-N-(1-cyano-2-(3'-(methylsulfonyl)biphenyl-4-yl)ethyl)tetrahydro-2H-pyran-4-carboxamide trifluoroacetic acid salt (S)-tert-Butyl 4-(1-cyano-2-(3'-(methylsulfonyl)biphenyl-4-yl)ethylcarbamoyl)tetrahydro-2H-pyran-4-ylcarbamate (Example 23, step (ii), 230 mg) in formic acid (1.5 mL) was stirred at room temperature for 5 h and then warmed at 50° C. for 2 min. The reaction mixture was evaporated and methanol was added and evaporated. The product was purified by reversed phase HPLC using methanol in 0.1% aqueous TFA solution as eluent to afford the titled compound (155 mg).

$^1$H NMR (399.826 MHz, d$_6$-DMSO) δ 9.24 (d, 1H), 8.44 (s, 3H), 8.13 (t, 1H), 8.02 (dt, 1H), 7.92 (dt, 1H), 7.77-7.72 (m, 3H), 7.47 (d, 2H), 5.19-5.12 (m, 1H), 3.71-3.63 (m, 2H), 3.63-3.55 (m, 2H), 3.29 (s, 3H), 3.33-3.18 (m, 2H), 2.24-2.14 (m, 1H), 2.09-1.99 (m, 1H), δ 1.69 (d, 1H), 1.48 (d, 1H).

m/e (MultiMode+) 428 [M+H]$^+$

EXAMPLE 24

(S)-4-Amino-N-(1-cyano-2-(4-(3-(2-methoxyethyl)-2-oxo-2,3-dihydrobenzo[d]oxazol-5-yl)phenyl)ethyl)tetrahydro-2H-pyran-4-carboxamide trifluoroacetic acid salt

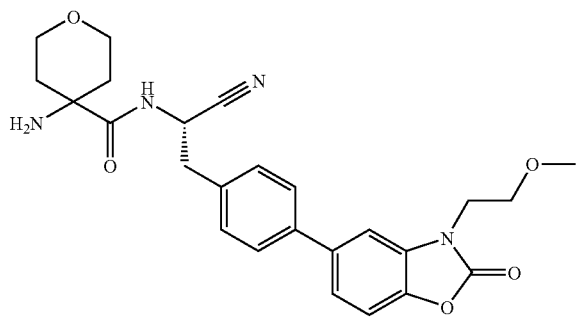

(i) 5-Bromo-3-(2-methoxyethyl)benzo[d]oxazol-2(3H)-one

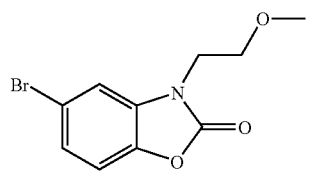

A mixture of 5-bromobenzo[d]oxazol-2(3H)-one (2.06 g), 1-bromo-2-methoxyethane (1.085 mL) and potassium carbonate (3.99 g) in acetonitrile (15 mL) was heated at 60° C. for 16 h. Water was added and the mixture was extracted with ethyl acetate (3 times). The organic layers were dried over magnesium sulfate, evaporated and purified by flash silica chromatography eluting with 5:1 isohexane/acetone to give the subtitled compound (1.359 g).

$^1$H NMR (300 MHz, CDCl$_3$) δ 7.28-7.18 (m, 2H), 7.06 (d, 1H), 3.97 (t, 2H), 3.69 (t, 2H), 3.36 (s, 3H).

(ii) (S)-tert-Butyl 4-(1-amino-3-(4-(3-(2-methoxyethyl)-2-oxo-2,3-dihydrobenzo[d]oxazol-5-yl)phenyl)-1-oxopropan-2-ylcarbamoyl)tetrahydro-2H-pyran-4-ylcarbamate

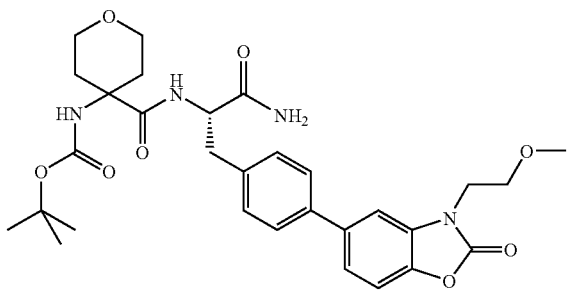

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 250 mg) in acetonitrile (8 mL) with 5-bromo-3-(2-methoxyethyl)benzo[d]oxazol-2(3H)-one (Example 24, step (i), 131 mg) was treated with an aqueous solution of sodium carbonate (2M, 0.483 mL). Nitrogen was bubbled through the solution and then 1,1 bis(di-tert-butylphosphino)ferrocene palladium dichloride (5 mg) was added. The reaction mixture was heated at 85° C. for 18 h under nitrogen and allowed to cool to room temperature. Purification by chromatography on silica eluting with 50-100% ethyl acetate/isohexane as eluent afford the sub-titled compound (66 mg).

m/e (APCI−) 581 [M−H]$^−$ (iii) (S)-tert-Butyl 4-(1-cyano-2-(4-(3-(2-methoxyethyl)-2-oxo-2,3-dihydrobenzo[d]oxazol-5-yl)phenyl)ethylcarbamoyl)tetrahydro-2H-pyran-4-ylcarbamate

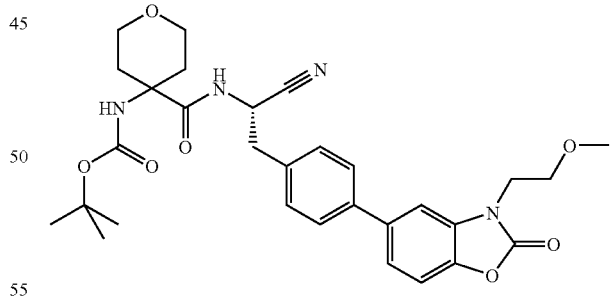

(S)-tert-Butyl 4-(1-amino-3-(4-(3-(2-methoxyethyl)-2-oxo-2,3-dihydrobenzo[d]oxazol-5-yl)phenyl)-1-oxopropan-2-ylcarbamoyl)tetrahydro-2H-pyran-4-ylcarbamate (Example 24, step (ii), 162 mg) in dichloromethane (8 mL) was treated with Burgess' reagent (133 mg) and the mixture was stirred at room temperature for 18 h. The solvent was partially evaporated and the mixture was purified by chromatography on silica eluting with 1:1 ethyl acetate/isohexane as eluent to yield a white solid (141 mg).

m/e (APCI+) 465 [M+2H−BOC]$^+$ (S)-4-Amino-N-(1-cyano-2-(4-(3-(2-methoxyethyl)-2-oxo-2,3-dihydrobenzo[d]oxazol-5-yl)phenyl)ethyl)tetrahydro-2H-pyran-4-carboxamide trifluoroacetic acid salt (S)-tert-Butyl 4-(1-cyano-2-(4-(3-(2-methoxyethyl)-2-oxo-2,3-dihydrobenzo[d]oxazol-5-yl)phenyl)ethylcarbamoyl)tetrahydro-2H-pyran-4-ylcarbamate (Example 24, step (iii), 141 mg) in formic acid (1.5 mL) was heated at 50° C. for 20 min. The mixture was evaporated and then methanol was added and the solvent was evaporated. The product was purified by reversed phase HPLC using methanol in 0.1% aqueous TFA as eluent to afford the titled compound as a solid (53 mg).
$^1$H NMR (399.826 MHz, $d_6$-DMSO) δ 9.23 (d, 1H), 8.45 (s, 3H), 7.66 (d, 2H), 7.60 (s, 1H), 7.44-7.40 (m, 4H), 5.17-5.09 (m, 1H), 4.07 (t, 2H), 3.67 (t, 4H), 3.62-3.56 (m, 2H), 3.31-3.16 (m, 2H), 3.25 (s, 3H), 2.25-2.14 (m, 1H), 2.09-1.98 (m, 1H), 1.69 (d, 1H), 1.49 (d, 1H).
m/e (MultiMode+) 465 [M+H]$^+$

EXAMPLE 25

(S)-4-Amino-N-(2-(4'-carbamoyl-3'-fluorobiphenyl-4-yl)-1-cyanoethyl)tetrahydro-2H-pyran-4-carboxamide

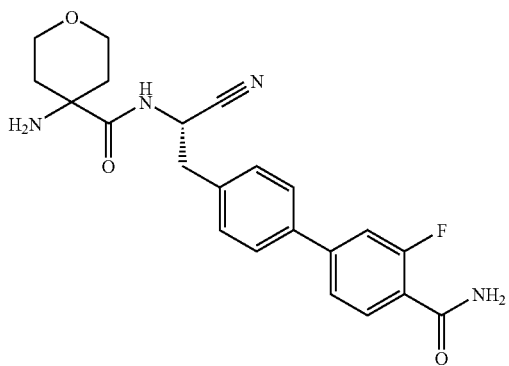

(i) (S)-tert-Butyl 4-(2-(4'-carbamoyl-3'-fluorobiphenyl-4-yl)-1-cyanoethylcarbamoyl)tetrahydro-2H-pyran-4-ylcarbamate

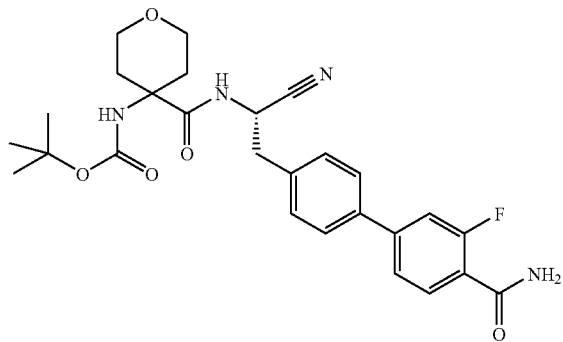

(S)-tert-Butyl 4-(1-cyano-2-(4-iodophenyl)ethylcarbamoyl)tetrahydro-2H-pyran-4-ylcarbamate (Example 15, step (i), 200 mg) and 4-carbamoyl-3-fluorophenylboronic acid (73 mg) in acetonitrile (8 mL) were treated with potassium acetate (79 mg) in water (4 mL). Nitrogen was bubbled through the mixture and then 1,1 bis(di-tert-butylphosphino) ferrocene palladium dichloride (5 mg) was added and the mixture was heated at 85° C. for 18 h under nitrogen. The reaction mixture was evaporated onto silica and purified by chromatography on silica eluting with ethyl acetate/isohexane (50:50 to 100:0) to afford the sub-titled compound (108 mg).
m/e (MultiMode+) 411 [M+2H−BOC]$^+$ (S)-4-Amino-N-(2-(4'-carbamoyl-3'-fluorobiphenyl-4-yl)-1-cyanoethyl)tetrahydro-2H-pyran-4-carboxamide (S)-tert-Butyl 4-(2-(4'-carbamoyl-3'-fluorobiphenyl-4-yl)-1-cyanoethylcarbamoyl)tetrahydro-2H-pyran-4-ylcarbamate (Example 25, step (i), 108 mg) in formic acid (2 mL) was heated at 50° C. for 20 mins. Volatiles were removed under reduced pressure and the residue azeotroped with methanol. The residue was purified by reversed phase HPLC using methanol in 0.1% aqueous TFA solution as eluent. The residue was converted to the free base by elution through a PL-HCO$_3$ MP cartridge in dichloromethane/methanol to afford the titled compound (53 mg).
$^1$H NMR (399.826 MHz, $d_6$-DMSO) δ 7.77-7.57 (m, 7H), 7.41 (d, 2H), 5.01 (t, 1H), 3.66-3.53 (m, 3H), 3.49-3.42 (m, 1H), 3.30-3.14 (m, 2H), 1.94-1.85 (m, 1H), 1.78-1.69 (m, 1H), 1.26-1.09 (m, 2H).
m/e (MultiMode+) 411 [M+H]$^+$

EXAMPLE 26

(S)-4-Amino-N-(1-cyano-2-(4-(2-methoxypyridin-4-yl)phenyl)ethyl)tetrahydro-2H-pyran-4-carboxamide

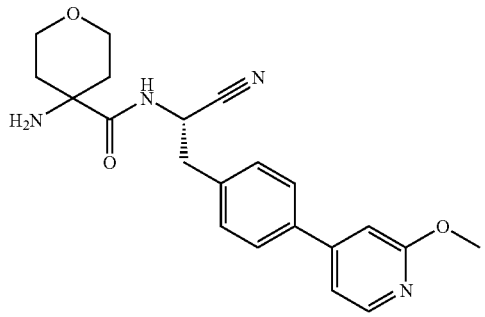

(i) (S)-tert-Butyl 4-(1-amino-3-(4-(2-methoxypyridin-4-yl)phenyl)-1-oxopropan-2-ylcarbamoyl)tetrahydro-2H-pyran-4-ylcarbamate

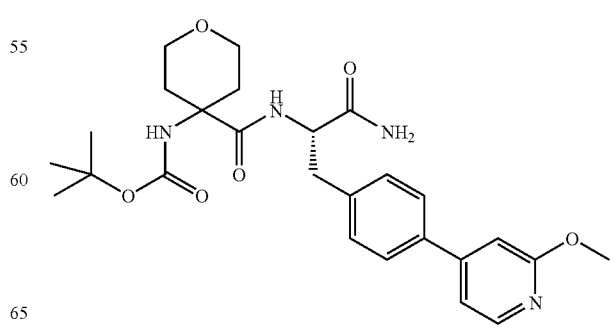

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 250 mg) and 4-bromo-2-methoxypyridine (91 mg) in acetonitrile (8 mL) were treated with aqueous sodium carbonate solution (2M, 0.5 mL) and nitrogen was bubbled through the mixture. 1,1 bis(Di-tert-butylphosphino)ferrocene palladium dichloride (5 mg) was added and the mixture was heated at 85° C. for 18 h. The mixture was evaporated onto silica and purified by chromatography on silica eluting with ethyl acetate to afford the sub-titled compound (214 mg).

m/e (MultiMode+) 499 [M+H]$^+$ (S)-4-Amino-N-(1-cyano-2-(4-(2-methoxypyridin-4-yl)phenyl)ethyl)tetrahydro-2H-pyran-4-carboxamide (S)-tert-Butyl 4-(1-amino-3-(4-(2-methoxypyridin-4-yl)phenyl)-1-oxopropan-2-ylcarbamoyl)tetrahydro-2H-pyran-4-ylcarbamate (Example 26, step (i), 214 mg) in dichloromethane (10 mL) was treated with Burgess' reagent (205 mg) and the mixture was stirred at room temperature for 18 h. The solvent was evaporated to give a residue that was dissolved in formic acid (2 mL) which was heated at 50° C. for 15 min. The mixture was evaporated and then methanol was added and the solvent was evaporated. The product was purified by reversed phase HPLC using methanol in 0.1% aqueous TFA as eluent. The residue was converted to the free base by elution through a PL-HCO$_3$ MP cartridge in dichloromethane/methanol to afford the titled compound (95 mg).

$^1$H NMR (399.826 MHz, d$_6$-DMSO) δ 8.22 (d, 1H), 7.74 (d, 2H), 7.42 (d, 2H), 7.30 (dd, 1H), 7.10-7.08 (m, 1H), 5.01 (t, 1H), 3.89 (s, 3H), 3.66-3.53 (m, 3H), 3.49-3.42 (m, 1H), 3.26-3.15 (m, 2H), 1.93-1.84 (m, 1H), 1.77-1.68 (m, 1H), 1.26-1.08 (m, 2H).

m/e (MultiMode+) 381 [M+H]$^+$

EXAMPLE 27

(S)-4-Amino-N-(1-cyano-2-(4'-(morpholinosulfonyl)biphenyl-4-yl)ethyl)tetrahydro-2H-pyran-4-carboxamide trifluoroacetic acid salt

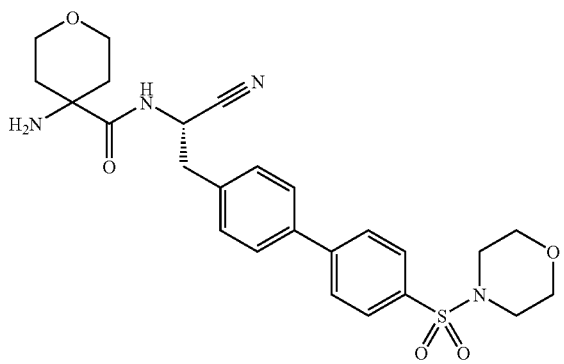

(i) (S)-tert-Butyl 4-(1-amino-3-(4'-(morpholinosulfonyl)biphenyl-4-yl)-1-oxopropan-2-ylcarbamoyl)tetrahydro-2H-pyran-4-ylcarbamate

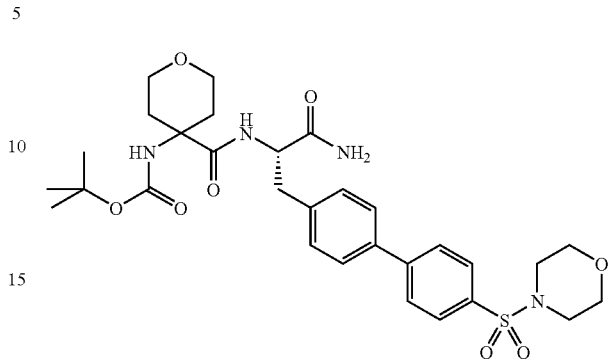

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 250 mg) in acetonitrile (8 mL) with 4-(4-bromophenylsulfonyl)morpholine (148 mg) was treated with aqueous sodium carbonate (2M, 0.5 mL) and nitrogen was bubbled through the mixture. 1,1 bis(Di-tert-butylphosphino)ferrocene palladium dichloride (5 mg) was added and the mixture was heated at 85° C. for 18 h under nitrogen. The reaction mixture was evaporated onto silica and purified by chromatography on silica eluting with ethyl acetate/isohexane (50:50 to 100:0) to afford the sub-titled compound (240 mg).

m/e (MultiMode−) 615 [M−H]$^−$ (ii) (S)-tert-Butyl 4-(1-cyano-2-(4'-(morpholinosulfonyl)biphenyl-4-yl)ethylcarbamoyl)tetrahydro-2H-pyran-4-ylcarbamate

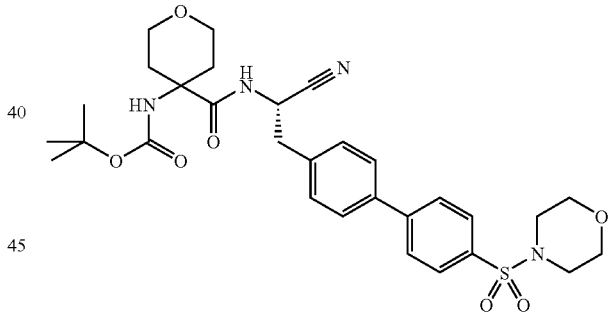

(S)-tert-Butyl 4-(1-amino-3-(4'-(morpholinosulfonyl)biphenyl-4-yl)-1-oxopropan-2-ylcarbamoyl)tetrahydro-2H-pyran-4-ylcarbamate (Example 27, step (i), 0.24 g) in dichloromethane (10 mL) was treated with Burgess' reagent (0.185 g) and the mixture was stirred at room temperature for 18 h. The solvent was removed under reduced pressure and the residue was purified by chromatography on silica eluting with ethyl acetate/isohexane (1:1) to afford the sub-titled compound (210 mg).

m/e (MultiMode−) 597 [M−H]$^−$ (S)-4-Amino-N-(1-cyano-2-(4'-(morpholinosulfonyl)biphenyl-4-yl)ethyl)tetrahydro-2H-pyran-4-carboxamide trifluoroacetic acid salt (S)-tert-Butyl 4-(1-cyano-2-(4'-(morpholinosulfonyl)biphenyl-4-yl)ethylcarbamoyl)tetrahydro-2H-pyran-4-ylcarbamate (Example 27, step (ii), 210 mg) in formic acid (1.5 mL) was stirred at room temperature for 1 h and then heated at 50° C. for 20 mins The mixture was evaporated and then methanol was added and the solvent was evaporated. The product was purified by reversed phase HPLC using methanol in 0.1% aqueous TFA as eluent to afford the titled compound as a trifluoroacetic acid salt (119 mg).

¹H NMR (399.826 MHz, d₆-DMSO) δ 9.24 (d, 1H), 8.44 (s, 3H), 7.97-7.92 (m, 2H), 7.83-7.78 (m, 2H), 7.75 (d, 2H), 7.47 (d, 2H), 5.20-5.12 (m, 1H), 3.70-3.55 (m, 8H), 3.34-3.16 (m, 2H), 2.93-2.88 (m, 4H), 2.24-2.14 (m, 1H), 2.09-1.98 (m, 1H), 1.69 (d, 1H), 1.48 (d, 1H).

m/e (MultiMode+) 499 [M+H]⁺

EXAMPLE 28

(S)-4-Amino-N-(1-cyano-2-(4-(4-methyl-3-oxo-3,4-dihydro-2H-benzo[b][1,4]thiazin-7-yl)phenyl)ethyl)tetrahydro-2H-pyran-4-carboxamide

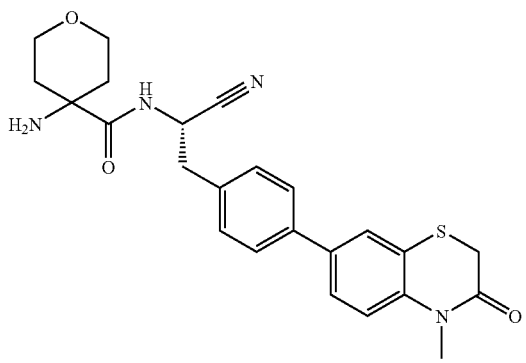

(i) 7-Bromo-2H-benzo[b][1,4]thiazin-3(4H)-one

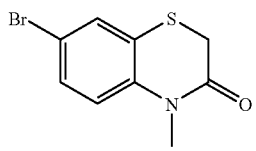

To sodium hydride (80% dispersion in oil, 59 mg) in DMF (3 mL) under nitrogen was added 7-bromo-2H-benzo[b][1,4]thiazin-3(4H)-one (0.3 g) and the mixture was stirred at room temperature for 1 h. Methyl iodide (0.115 mL) was added and the mixture was stirred overnight at room temperature. The reaction mixture was poured into ice/water and extracted with ethyl acetate (×2). The ethyl acetate was washed with water (×3), dried over magnesium sulfate and the solvent was evaporated. The resulting yellow oil was purified by chromatography on silica eluting with ethyl acetate/isohexane (1:9) to afford the sub-titled compound (293 mg).

(ii) (S)-tert-Butyl 4-(1-amino-3-(4-(4-methyl-3-oxo-3,4-dihydro-2H-benzo[b][1,4]thiazin-7-yl)phenyl)-1-oxopropan-2-ylcarbamoyl)tetrahydro-2H-pyran-4-ylcarbamate

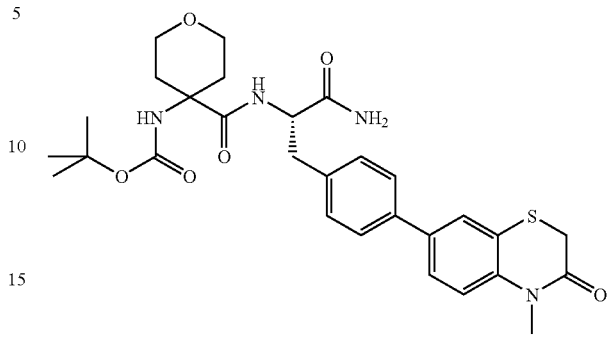

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 241 mg) in acetonitrile (8 mL) with 7-bromo-4-methyl-2H-benzo[b][1,4]thiazin-3(4H)-one (Example 28, step (i), 120 mg) was treated with aqueous sodium carbonate solution (2M, 0.465 mL) and then nitrogen was bubbled through the mixture. 1,1 bis(Di-tert-butylphosphino)ferrocene palladium dichloride (5 mg) was added and the mixture was heated at 85° C. under nitrogen for 18 h. A further addition of sodium carbonate solution (2M, 0.2 mL) and 1,1 bis(di-tert-butylphosphino)ferrocene palladium dichloride (5 mg) was made and the mixture was heated at 85° C. for a further 18 h. A further addition of (S)-tert-butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 20 mg) was made and the mixture was heated at 85° C. for 18 h. The mixture was purified by chromatography on silica eluting with ethyl acetate/isohexane (50:50 to 100:0) to afford the sub-titled compound (132 mg).
m/e (MultiMode−) 567 [M−H]⁻

(iii) (S)-tert-Butyl 4-(1-cyano-2-(4-(4-methyl-3-oxo-3,4-dihydro-2H-benzo[b][1,4]thiazin-7-yl)phenyl)ethylcarbamoyl)tetrahydro-2H-pyran-4-ylcarbamate

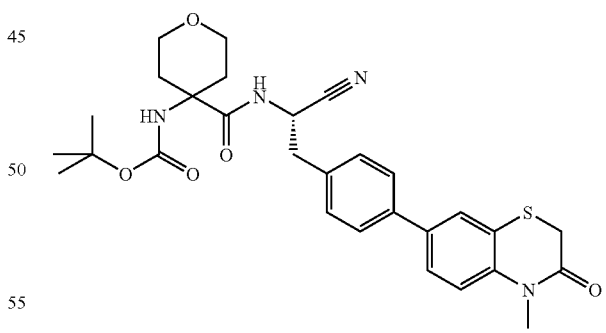

(S)-tert-Butyl 4-(1-amino-3-(4-(4-methyl-3-oxo-3,4-dihydro-2H-benzo[b][1,4]thiazin-7-yl)phenyl)-1-oxopropan-2-ylcarbamoyl)tetrahydro-2H-pyran-4-ylcarbamate (Example 28, step (ii), 138 mg) in dichloromethane (10 mL) was treated with Burgess' reagent (116 mg) and stirred at room temperature for 18 h. The solvent was partially evaporated and the residue absorbed onto silica and purified by chromatography on silica eluting with ethyl acetate/isohexane (50:50 to 70:30) to afford the sub-titled compound (120 mg).
m/e (MultiMode+) 451 [M+2H−BOC]⁺

(S)-4-Amino-N-(1-cyano-2-(4-(4-methyl-3-oxo-3,4-dihydro-2H-benzo[b][1,4]thiazin-7-yl)phenyl)ethyl)tetrahydro-2H-pyran-4-carboxamide (S)-tert-Butyl 4-(1-cyano-2-(4-(4-methyl-3-oxo-3,4-dihydro-2H-benzo[b][1,4]thiazin-7-yl)phenyl)ethylcarbamoyl)tetrahydro-2H-pyran-4-ylcarbamate (Example 28, step (iii), 120 mg) in formic acid (2 mL) was heated at 50° C. for 20 mins. The solvent was removed under reduced pressure and the residue azeotroped with methanol. The product was purified by reversed phase HPLC using methanol in 0.1% aqueous TFA and then converted to the free base by elution through a PL-HCO$_3$ MP cartridge with dichloromethane/methanol to afford the titled compound (51 mg).

$^1$H NMR (399.826 MHz, d$_6$-DMSO) δ 7.71-7.57 (m, 4H), 7.40-7.31 (m, 3H), 4.99 (t, 1H), 3.66-3.53 (m, 5H), 3.49-3.42 (m, 1H), 3.37 (s, 3H), 3.24-3.13 (m, 2H), 1.94-1.84 (m, 1H), 1.79-1.69 (m, 1H), 1.17 (dd, 2H).

m/e (MultiMode+) 451 [M+H]$^+$

EXAMPLE 29

(S)-4-Amino-N-(1-cyano-2-(4'-(4-methylpiperazin-1-ylsulfonyl)biphenyl-4-yl)ethyl)tetrahydro-2H-pyran-4-carboxamide

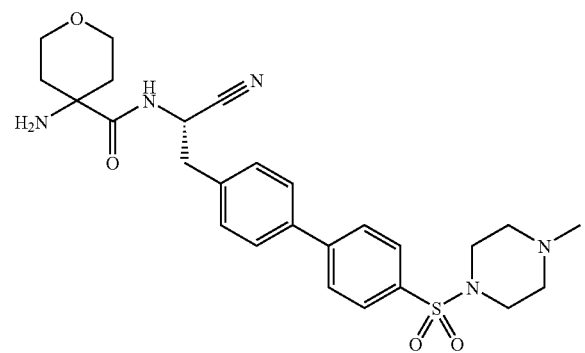

(i) (S)-tert-Butyl 4-(1-amino-3-(4'-(4-methylpiperazin-1-ylsulfonyl)biphenyl-4-yl)-1-oxopropan-2-ylcarbamoyl)tetrahydro-2H-pyran-4-ylcarbamate

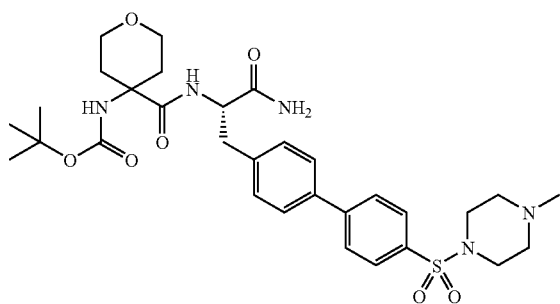

(S)-tert-Butyl 4-(1-amino-3-(4-iodophenyl)-1-oxopropan-2-ylcarbamoyl)tetrahydro-2H-pyran-4-ylcarbamate (Example 1, step (iii), 250 mg) and 1-methyl-4-(4-(4,4,5,5-tetramethyl-1,3,2-dioxaborolan-2-yl)phenylsulfonyl)piperazine (177 mg) in acetonitrile (8 mL) was treated with aqueous sodium carbonate solution (2M, 0.483 mL) and then nitrogen was bubbled through the mixture. 1,1 bis(Di-tert-butylphosphino)ferrocene palladium dichloride (5 mg) was added and the mixture was heated at 85° C. under nitrogen for 18 h. The mixture was purified by chromatography on silica eluting with ethyl acetate/isohexane (70:10 to 100:0), then methanol/ethyl acetate (5:95) and then methanol/ethyl acetate/triethylamine (5:95:1) to afford the sub-titled compound (267 mg).

m/e (MultiMode−) 629 [M−H]$^-$ (ii) (S)-tert-Butyl 4-(1-cyano-2-(4'-(4-methylpiperazin-1-ylsulfonyl)biphenyl-4-yl)ethylcarbamoyl)tetrahydro-2H-pyran-4-ylcarbamate

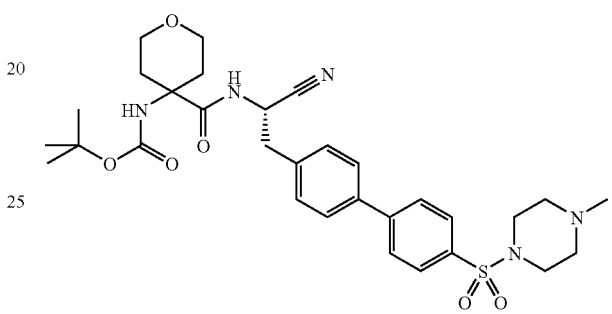

(S)-tert-Butyl 4-(1-amino-3-(4'-(4-methylpiperazin-1-yl-sulfonyl)biphenyl-4-yl)-1-oxopropan-2-ylcarbamoyl)tetrahydro-2H-pyran-4-ylcarbamate (Example 29, step (i), 267 mg) in dichloromethane (10 mL) was treated with Burgess' reagent (202 mg) and the mixture was stirred at room temperature for 18 h. The solvent was partially evaporated under reduced pressure and the mixture was purified by chromatography on silica eluting with methanol/dichloromethane (0:100 to 5:95), triethylamine/methanol/dichloromethane (1:5:95) to afford the sub-titled compound (250 mg).

m/e (MultiMode+) 612 [M+H]$^+$ (S)-4-Amino-N-(1-cyano-2-(4'-(4-methylpiperazin-1-ylsulfonyl)biphenyl-4-yl)ethyl)tetrahydro-2H-pyran-4-carboxamide (S)-tert-Butyl 4-(1-cyano-2-(4'-(4-methylpiperazin-1-yl-sulfonyl)biphenyl-4-yl)ethylcarbamoyl)tetrahydro-2H-pyran-4-ylcarbamate (Example 29, step (ii), 250 mg) in formic acid (2 mL) was heated at 50° C. for 20 min. Volatiles were removed under reduced pressure and then azeotroped with methanol. The product was purified by reversed phase HPLC using methanol in 0.1% aqueous TFA as eluent. The residue was converted to the free base by elution through a PL-HCO$_3$ MP cartridge in dichloromethane/methanol to afford the titled compound (43 mg).

$^1$H NMR (399.826 MHz, d$_6$-DMSO) δ 7.86 (dd, 4H), 7.58 (dd, 4H), 5.04 (t, 1H), 3.66-3.45 (m, 4H), 3.30-3.16 (m, 2H), 2.97-2.88 (m, 4H), 2.41-2.35 (m, 4H), 2.15 (s, 3H), 1.96-1.75 (m, 2H), 1.29-1.17 (m, 2H).

m/e (MultiMode+) 512 [M+H]$^+$

EXAMPLE 30

(S)-4-Amino-N-(1-cyano-2-(4-(2-methyl-3-oxoisoindolin-5-yl)phenyl)ethyl)tetrahydro-2H-pyran-4-carboxamide trifluoroacetic acid salt

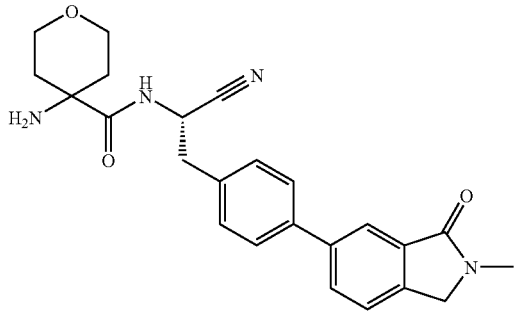

(i) 6-Bromo-2-methylisoindolin-1-one

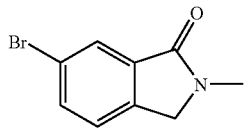

Methyl 5-bromo-2-methylbenzoate (3 g) in ethyl acetate (100 mL) was treated with N-chlorosuccinimide (1.749 g). The mixture was stirred and heated under reflux whilst being irradiated with a halogen lamp for 5 h. The reaction mixture was cooled and washed with 10% aqueous sodium metabisufite (100 mL) and water. The organic phase was dried over magnesium sulfate and concentrated to an oil. The crude product was treated with 8M methylamine in ethanol (20 mL) and the resulting mixture heated under reflux for 30 min. After cooling, the solution was concentrated to an oil, and the mixture purified on silica gel eluting with ethyl acetate to afford the sub-titled compound (0.300 g).

$^1$H NMR (399.824 MHz, CDCl$_3$) δ 7.94 (d, 1H), 7.61 (dd, 1H), 7.28 (d, 1H), 4.30 (s, 2H), 3.17 (s, 3H).

(ii) (S)-tert-Butyl 4-(1-amino-3-(4-(2-methyl-3-oxoisoindolin-5-yl)phenyl)-1-oxopropan-2-ylcarbamoyl)tetrahydro-2H-pyran-4-ylcarbamate

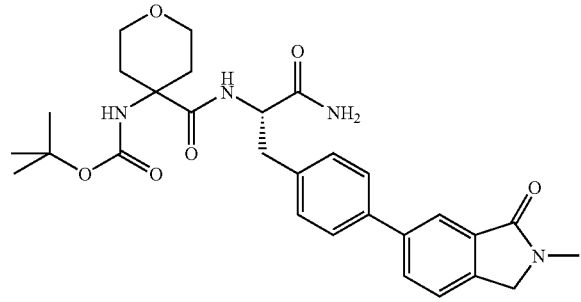

(S)-tert-Butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 300 mg), 6-bromo-2-methylisoindolin-1-one (Example 30, step (i), 131 mg) and potassium acetate (171 mg) in a mixture of acetonitrile (15 mL) and water (5 mL) was stirred under nitrogen at 90° C. with 1,1 bis(di-tert-butylphosphino) ferrocene palladium dichloride (378 mg). After 4 h the reaction mixture was cooled to room temperature and diluted with water (50 mL). The products were extracted with ethyl acetate (3×50 mL) and the combined extracts dried over magnesium sulfate and concentrated to afford the sub-titled compound (200 mg).

m/e (MultiMode+) 436 [M+2H−BOC]$^+$ (S)-4-Amino-N-(1-cyano-2-(4-(2-methyl-3-oxoisoindolin-5-yl)phenyl)ethyl)tetrahydro-2H-pyran-4-carboxamide trifluoroacetic acid salt (S)-tert-Butyl 4-(1-amino-3-(4-(2-methyl-3-oxoisoindolin-5-yl)phenyl)-1-oxopropan-2-ylcarbamoyl)tetrahydro-2H-pyran-4-ylcarbamate (Example 30, step (ii), 200 mg) in dichloromethane (20 mL) was stirred at room temperature with Burgess' reagent (178 mg) for 20 h. The reaction mixture was concentrated to dryness, and the residue stirred at room temperature in formic acid (0.5 mL) for 2 h. The solution was diluted with water (20 mL) and the mixture basified with '880' ammonia solution. The products were extracted into ethyl acetate (100 mL) and the extract dried over magnesium sulfate. Concentration of the solution gave a gum which was purified by reversed phase HPLC using methanol in 0.1% aqueous TFA solution as eluent to afford the titled compound as a trifluoroacetic acid salt (90 mg).

$^1$H NMR (500.303 MHz, D$_2$O) δ 7.60-7.56 (m, 2H), 7.44 (d, 2H), 7.38 (d, 1H), 7.28 (d, 2H), 5.17 (dd, 1H), 4.25 (s, 2H), 3.70-3.53 (m, 3H), 3.43-3.37 (m, 1H), 3.31 (dd, 1H), 3.16 (dd, 1H), 2.99 (s, 3H), 2.20-2.12 (m, 1H), 2.05-1.97 (m, 1H), 1.86-1.80 (m, 1H), 1.68-1.61 (m, 1H).

m/e (MultiMode+) 419 [M+H]$^+$

EXAMPLE 31

(S)-4-Amino-N-(1-cyano-2-(4-(2-methyl-1-oxoisoindolin-5-yl)phenyl)ethyl)tetrahydro-2H-pyran-4-carboxamide

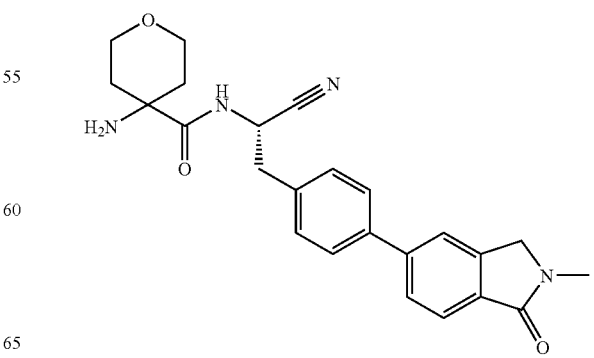

(i) 5-Bromo-2-methylisoindolin-1-one

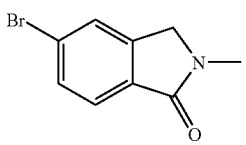

A solution of methyl 4-bromo-2-(bromomethyl)benzoate (410 mmol) in MeNH$_2$/MeOH (1500 mL) was heated to reflux and stirred for 18 h. The reaction mixture was concentrated and the residue was purified by chromatography on silica eluting with petroleum ether/ethyl acetate (6:1 to 3:1) to afford the sub-titled compound (48.5 g).

$^1$H NMR (400 MHz, CDCl$_3$): δ 7.63-7.61 (m, 1H), 7.53-7.54 (m, 2H), 4.29 (s, 2H), 3.12 (s, 3H).

(ii) 2-Methyl-5-(4,4,5,5-tetramethyl-1,3,2-dioxaborolan-2-yl)isoindolin-1-one

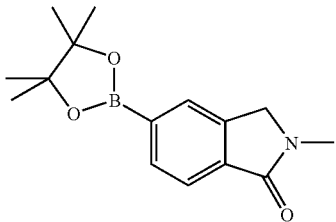

To a solution of 5-bromo-2-methylisoindolin-1-one (Example 31, step (i), 60.4 g) in dioxane (2 L) was added 4,4,4',4',5,5,5',5'-octamethyl-2,2'-bi(1,3,2-dioxaborolane) (67.8 g), potassium acetate (65.4 g) and Pd(dppf)Cl$_2$ (6 g) under an atmosphere of nitrogen. The mixture was heated to 100° C. and stirred for 4 h. The reaction mixture was cooled to room temperature and filtered. The filtrate was concentrated and the crude product was purified by chromatography on silica eluting with petroleum ether/ethyl acetate (6:1 to 2:1) to afford the sub-titled compound (72 g).

$^1$H NMR (400 MHz, CDCl$_3$): δ 7.89-7.88 (m, 2H), 7.83-7.81 (m, 1H), 4.35 (s, 2H), 3.19 (s, 3H), 10.34 (s, 12H).

(iii) 2-Methyl-1-oxoisoindolin-5-ylboronic acid

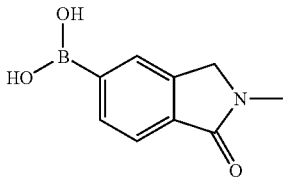

To a solution of crude 2-methyl-5-(4,4,5,5-tetramethyl-1,3,2-dioxaborolan-2-yl)isoindolin-1-one (Example 31, step (ii), 53 g) in acetone (600 mL) was added aqueous HCl solution (2M, 600 mL) and the solution was heated at reflux for 18 h. The solution was concentrated under vacuum to remove acetone and then cooled to 10° C. The resulting precipitate was filtered and dried under vacuum to afford the sub-titled compound (26.8 g).

$^1$H NMR (400 MHz, CDCl$_3$): δ 8.21 (s, 2H), 7.91 (s, 1H), 7.86-7.84 (d, 1H), 7.59-7.58 (d, 1H), 4.428 (s, 2H), 3.05 (s, 3H).

(iv) (S)-tert-Butyl 4-(1-amino-3-(4-(2-methyl-1-oxoisoindolin-5-yl)phenyl)-1-oxopropan-2-ylcarbamoyl)tetrahydro-2H-pyran-4-ylcarbamate

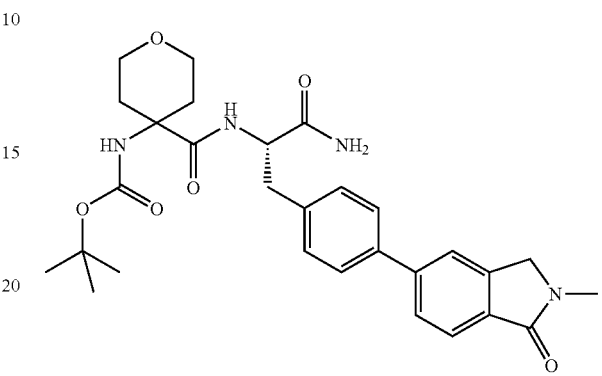

Potassium carbonate (276 mg) in water (2.0 mL) was added to (S)-tert-butyl 4-(1-amino-3-(4-iodophenyl)-1-oxopropan-2-ylcarbamoyl)tetrahydro-2H-pyran-4-ylcarbamate (Example 1, step (iii), 517 mg), 2-methyl-1-oxoisoindolin-5-ylboronic acid (Example 31, step (iii), 191 mg) and 1,1 bis (di-tert-butylphosphino)ferrocene palladium dichloride (98 mg) in degassed acetonitrile (12 mL) at 20° C. under nitrogen. The resulting solution was stirred at 80° C. for 30 min. The reaction mixture was cooled, filtered and diluted with dichloromethane, and washed with water. The organic extract was dried over magnesium sulfate, filtered and evaporated to afford crude product. The crude product was purified by chromatography in silica eluting with methanol/ethyl acetate (5:95 to 15:85). Pure fractions were evaporated to dryness to afford the sub-titled compound (469 mg).

m/e (MultiMode+) 537 [M+H]$^+$

(v) (S)-tert-Butyl 4-(1-cyano-2-(4-(2-methyl-1-oxoisoindolin-5-yl)phenyl)ethylcarbamoyl)tetrahydro-2H-pyran-4-ylcarbamate

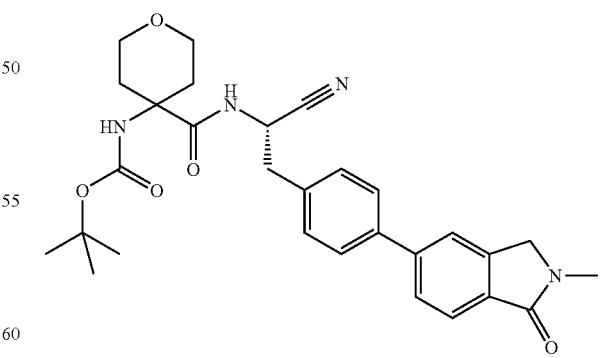

Burgess' reagent (638 mg) was added to (S)-tert-butyl 4-(1-amino-3-(4-(2-methyl-1-oxoisoindolin-5-yl)phenyl)-1-oxopropan-2-ylcarbamoyl)tetrahydro-2H-pyran-4-ylcarbamate (Example 31, step (iv), 718 mg) in dichloromethane (25 mL) at 20° C. under nitrogen. The resulting solution was stirred at room temperature for 17 h. The reaction mixture was diluted with dichloromethane, and washed with water. The organic layer was dried over magnesium sulfate, filtered and evaporated to afford crude material. The crude product was purified by chromatography on silica eluting with methanol/ethyl acetate (0:100 to 5:95) to afford sub-titled compound (436 mg).

$^1$H NMR (500 MHz, $d_6$-DMSO) δ 8.47 (s, 1H), 7.86 (s, 1H), 7.73 (q, 2H), 7.67 (d, 2H), 7.40 (d, 2H), 7.05 (s, 1H), 5.08 (s, 1H), 4.51 (s, 2H), 3.63-3.38 (m, 4H), 3.23-3.11 (m, 2H), 3.09 (s, 3H), 1.91 (s, 1H), 1.69 (d, 2H), 1.54 (d, 1H), 1.38 (s, 9H).

m/e (MultiMode+) 519 [M+H]$^+$

(S)-4-Amino-N-(1-cyano-2-(4-(2-methyl-1-oxoisoindolin-5-yl)phenyl)ethyl)tetrahydro-2H-pyran-4-carboxamide To (S)-tert-butyl 4-(1-cyano-2-(4-(2-methyl-1-oxoisoindolin-5-yl)phenyl)ethylcarbamoyl)tetrahydro-2H-pyran-4-ylcarbamate (Example 31, step (v), 436 mg) was added formic acid (9.7 mL) and the mixture heated to 50° C. for 15 min. The mixture was allowed to cool to room temperature, diluted with methanol and then evaporated to dryness. The material was purified by reversed phase HPLC (Waters X-Bridge column) eluting with methanol in aqueous 0.1% trifluoroacetic acid as eluent. The fractions containing the desired compound were combined, evaporated and then dissolved in dichloromethane and washed with saturated aqueous sodium hydrogen carbonate. The organic layer was dried over magnesium sulfate and evaporated. The residue was triturated with diethyl ether and evaporated to give a product that was slurried in water (6.9 mL) and acetonitrile (0.36 mL) for 4 days. The solid was collected by filtration, washed with water and then dried under vacuum at 50° C. to afford the titled compound (212 mg).

$^1$H NMR (500 MHz, $d_6$-DMSO) δ 7.86 (s, 1H), 7.76-7.70 (m, 2H), 7.69 (d, 2H), 7.41 (d, 2H), 5.02 (t, 1H), 4.51 (s, 2H), 3.66-3.54 (m, 3H), 3.46 (dt, 1H), 3.25-3.16 (m, 2H), 3.09 (s, 3H), 1.89 (ddd, 1H), 1.74 (ddd, 1H), 1.17 (dd, 2H).

m/e (MultiMode+) 419 [M+H]$^+$

EXAMPLE 32

(S)-4-Amino-N-(1-cyano-2-(4-(6-methyl-7-oxo-6,7-dihydro-5H-pyrrolo[3,4-b]pyridin-3-yl)phenyl)ethyl)tetrahydro-2H-pyran-4-carboxamide

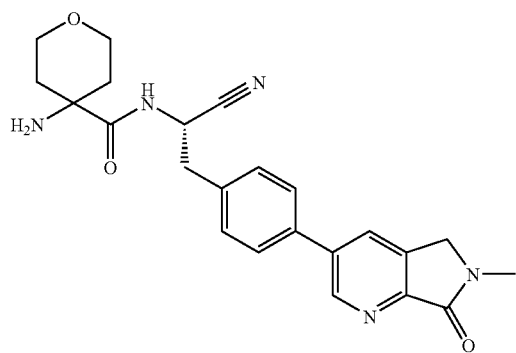

(i) Methyl 5-bromo-3-(bromomethyl)picolinate

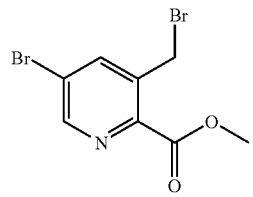

Methyl 5-bromo-3-methylpicolinate (800 mg) in dichloromethane (5 mL) was treated with N-bromosuccinimide (619 mg) and AIBN (14.28 mg). The mixture was stirred and irradiated with a 500 W halogen lamp for 3.5 h. The reaction mixture was cooled and diluted with dichloromethane, and washed with water. The organic layer was dried over magnesium sulfate, filtered and evaporated to afford the sub-titled compound (1036 mg).

m/e (MultiMode+) 310 [M+H]$^+$

(ii) 3-Bromo-6-methyl-5H-pyrrolo[3,4-b]pyridin-7(6H)-one

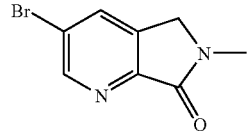

Methylamine (2M in THF, 9.05 mL) was added to methyl 5-bromo-3-(bromomethyl)picolinate (Example 32, step (i), 1.036 g) in tetrahydrofuran (5 mL) at 20° C. under nitrogen. The resulting suspension was stirred at 70° C. for 30 min. The reaction mixture was cooled and filtered, and the filtrate evaporated to dryness to afford crude product. The crude product was purified by chromatography on silica eluting with ethyl acetate/dichloromethane (5:95 to 100:0). The solid collected during the filtration was dissolved in ethyl acetate and washed with water, extracted with dichloromethane, and then washed with saturated aqueous sodium bicarbonate solution and extracted again with dichloromethane. The combined organic extracts were dried over magnesium sulfate, and then combined with the chromatographed material to afford the sub-titled compound (0.372 g).

$^1$H NMR (400 MHz, $d_6$-DMSO) δ 8.82 (d, 1H), 8.37 (d, 1H), 4.48 (s, 2H), 3.10 (s, 3H).

m/e (MultiMode+) 229 [M+H]$^+$

(iii) (S)-tert-Butyl 4-(1-amino-3-(4-(6-methyl-7-oxo-6,7-dihydro-5H-pyrrolo[3,4-b]pyridin-3-yl)phenyl)-1-oxopropan-2-ylcarbamoyl)tetrahydro-2H-pyran-4-ylcarbamate

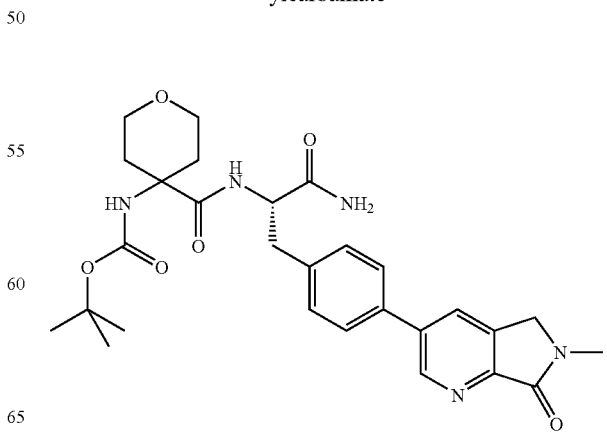

Potassium carbonate (176 mg) in water (2 mL) was added to (S)-tert-butyl 4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (Example 16, step (i), 329 mg), 3-bromo-6-methyl-5H-pyrrolo[3,4-b]pyridin-7(6H)-one (Example 32, step (ii), 144 mg) and 1,1 bis(di-tert-butylphosphino)ferrocene palladium dichloride (50 mg) in degassed acetonitrile (12 mL) at 20° C. under nitrogen. The resulting solution was stirred at 80° C. for 90 min. The reaction mixture was cooled and filtered and the filtrate diluted with ethyl acetate, and washed with water. The aqueous was then extracted with dichloromethane and the combined organics dried over magnesium sulfate, filtered and evaporated to afford crude product. The crude product was purified by chromatography on silica eluting with methanol/ethyl: acetate (15:85 to 25:75). Pure fractions were evaporated to dryness to afford the sub-titled compound (278 mg).

m/e (MultiMode+) 438 [M+2H−BOC]$^+$

(iv) (S)-tert-Butyl 1-(1-cyano-2-(4-(6-methyl-7-oxo-6,7-dihydro-5H-pyrrolo[3,4-b]pyridin-3-yl)phenyl)ethylcarbamoyl)cyclohexylcarbamate

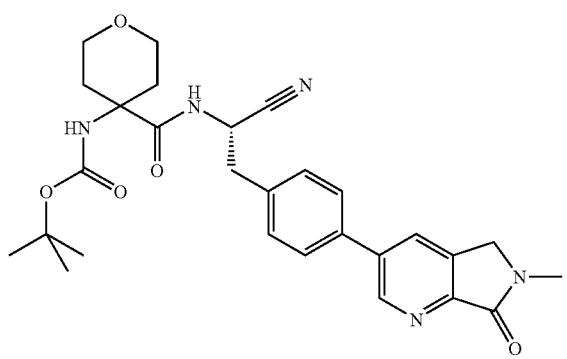

Burgess' reagent (348 mg) was added to (S)-tert-butyl 1-(1-amino-3-(4-(6-methyl-7-oxo-6,7-dihydro-5H-pyrrolo[3,4-b]pyridin-3-yl)phenyl)-1-oxopropan-2-ylcarbamoyl)cyclohexylcarbamate (Example 32, step (iii), 391 mg) in dichloromethane (25 mL) at 20° C. under nitrogen. The resulting solution was stirred at room temperature for 16 h. The reaction mixture was diluted with dichloromethane, and washed with water. The organic layer was dried over magnesium sulfate, filtered and evaporated to afford crude product. The crude product was purified by chromatography on silica eluting with methanol/ethyl acetate (10:90 to 40:60) to afford the sub-titled compound (360 mg).

m/e (MultiMode+) 420 [M+2H−BOC]$^+$

(S)-4-Amino-N-(1-cyano-2-(4-(6-methyl-7-oxo-6,7-dihydro-5H-pyrrolo[3,4-b]pyridin-3-yl)phenyl)ethyl)tetrahydro-2H-pyran-4-carboxamide To (S)-tert-butyl 4-(1-cyano-2-(4-(6-methyl-7-oxo-6,7-dihydro-5H-pyrrolo[3,4-b]pyridin-3-yl)phenyl)ethylcarbamoyl)tetrahydro-2H-pyran-4-ylcarbamate (Example 32, step (iv), 0.186 g) was added formic acid (9.6 mL) and the mixture heated to 50° C. for 15 min. The mixture was allowed to cool to room temperature and diluted with methanol, and then evaporated to dryness. The residue was suspended in methanol, filtered and the filtrate was evaporated. The residue from the filtrate was purified by reversed phase HPLC (Waters X-Bridge column) eluting with methanol in aqueous 0.1% trifluoroacetic acid. The fractions containing the desired compound were combined and evaporated, and the residue combined with the solid collected during the filtration. The purified compound was dissolved in dichloromethane and washed with saturated aqueous sodium hydrogen carbonate solution. The organics were dried to over magnesium sulfate and evaporated, triturated with diethyl ether and evaporated to afford a white solid. The solid was suspended in water (2.2 mL) and acetonitrile (0.11 mL) and stirred at room temperature for 3 days. The resulting solid was collected by filtration and washed with water and then dried under vacuum at 50° C. to afford the titled compound (56 mg).

$^1$H NMR (500 MHz, d$_6$-DMSO) δ 8.99 (d, 1H), 8.32 (d, 1H), 7.77 (d, 2H), 7.46 (d, 2H), 5.03 (t, 1H), 4.54 (s, 2H), 3.66-3.53 (m, 3H), 3.46 (dt, 1H), 3.27-3.18 (m, 2H), 3.13 (s, 3H), 1.89 (ddd, 1H), 1.74 (ddd, 1H), 1.17 (dd, 2H).

m/e (MultiMode+) 420 [M+H]$^+$

EXAMPLE 33

(S)-4-Amino-N-(1-cyano-2-(4-(2-oxo-2,3-dihydrobenzo[d]oxazol-5-yl)phenyl)ethyl)tetrahydro-2H-pyran-4-carboxamide trifluoroacetatic acid salt

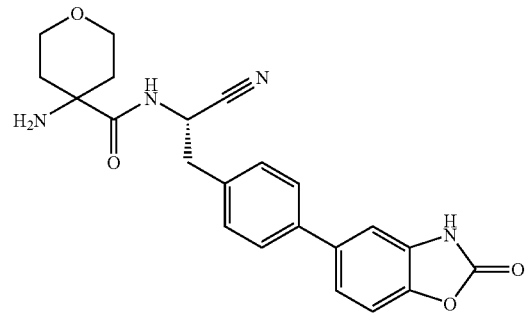

(i) 5-(4,4,5,5-Tetramethyl-1,3,2-dioxaborolan-2-yl)benzo[d]oxazol-2(3H)-one

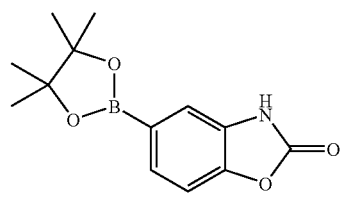

To a mixture of 4,4,4',4',5,5,5',5'-octamethyl-2,2'-bi(1,3,2-dioxaborolane) (3.09 g), 5-bromobenzo[d]oxazol-2(3H)-one (2 g) and potassium acetate (2.75 g) in acetonitrile (20 mL) and water (15 mL), under a nitrogen atmosphere was added 1,1 bis(di-tert-butylphosphino)ferrocene palladium dichloride (61 mg) and the mixture stirred and heated under reflux for 50 h. The cooled reaction mixture was concentrated under vacuum and the residue partitioned between water (100 mL) and diethyl ether (200 mL). The layers were separated and the organic extract was dried over magnesium sulfate and concentrated to dryness to afford a viscous oil. The crude product was purified by chromatography on silica eluting with ethyl acetate/isohexane (20:80) to afford the sub-titled compound (1.1 g).

$^1$H NMR (399.824 MHz, CDCl$_3$) δ 9.03 (s, 1H), 7.61 (dd, 1H), 7.53 (s, 1H), 7.21 (d, 1H), 1.35 (s, 12H).

(ii) (S)-tert-Butyl 4-(1-cyano-2-(4-(2-oxo-2,3-dihydrobenzo[d]oxazol-5-yl)phenyl)ethylcarbamoyl)tetrahydro-2H-pyran-4-ylcarbamate

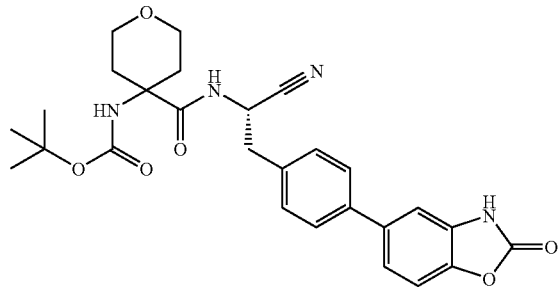

(S)-tert-Butyl 4-(1-cyano-2-(4-iodophenyl)ethylcarbamoyl)tetrahydro-2H-pyran-4-ylcarbamate (Example 15, step (i), 300 mg), potassium acetate (177 mg) and 5-(4,4,5,5-tetramethyl-1,3,2-dioxaborolan-2-yl)benzo[d]oxazol-2 (3H)-one (Example 33, step (i), 157 mg) in a mixture of acetonitrile (25 mL) and water (10 mL) under a nitrogen atmosphere, was treated with 1,1 bis(di-tert-butylphosphino)ferrocene palladium dichloride (12 mg) and the mixture stirred and heated 90° C. for 18 h. The reaction mixture was cooled to room temperature and diluted with water. The products were extracted into ethyl acetate (2×100 mL) and the combined extracts dried over magnesium sulphate and concentrated to dryness. The residue was purified by chromatography on silica eluting with ethyl acetate to afford the sub-titled compound (160 mg).

m/e (MultiMode−) 505 [M−H]$^-$ (S)-4-Amino-N-(1-cyano-2-(4-(2-oxo-2,3-dihydrobenzo[d]oxazol-5-yl)phenyl)ethyl)tetrahydro-2H-pyran-4-carboxamide trifluoroacetic acid salt (S)-tert-Butyl 4-(1-cyano-2-(4-(2-oxo-2,3-dihydrobenzo[d]oxazol-5-yl)phenyl)ethylcarbamoyl)tetrahydro-2H-pyran-4-ylcarbamate (Example 33, step (ii), 160 mg) was heated at 50° C. in formic acid (0.5 mL) for 10 min. The cooled solution was diluted with water (50 mL) and basified with '880' ammonia and the resulting precipitate extracted into ethyl acetate (200 mL). The dried extract was concentrated to dryness and purified purified by reversed phase HPLC (using a SunFire column) eluting with methanol/0.1% aqueous trifluoroacetic acid. The pure fractions were freeze dried to afford the titled compound as a trifluoroacetic acid salt (36 mg) TFA salt as a colourless solid.

$^1$H NMR (500.303 MHz, d$_6$-DMSO+D$_2$O) δ 7.61 (d, 2H), 7.40 (d, 2H), 7.38-7.34 (m, 2H), 7.31 (s, 1H), 5.13 (dd, 1H), 3.71-3.54 (m, 4H), 3.31-3.15 (m, 2H), 2.24-2.14 (m, 1H), 2.09-2.01 (m, 1H), 1.71 (d, 1H), 1.52 (d, 1H).

m/e (MultiMode+) 407 [M+H]$^+$

EXAMPLE 34

4-Amino-N-{(1S)-1-cyano-2-[4-(2,2-dioxido-1,3-dihydro-2-benzothiophen-5-yl)phenyl]ethyl}tetrahydro-2H-pyran-4-carboxamide

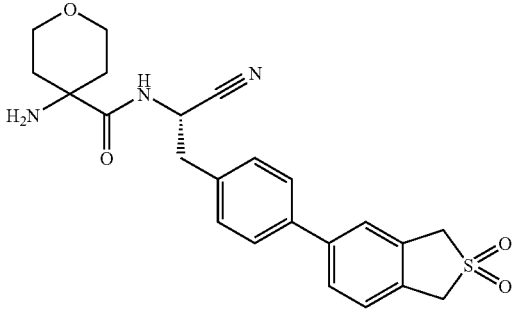

(i) N-α-({4-[(tert-Butoxycarbonyl)amino]tetrahydro-2H-pyran-4-yl}carbonyl)-4-(2,2-dioxido-1,3-dihydro-2-benzothiophen-5-yl)phenylalaninamide

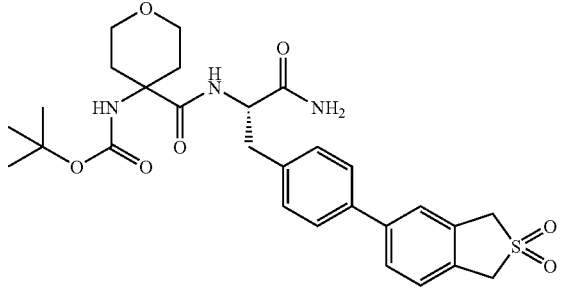

2-(2,2-Dioxido-1,3-dihydro-2-benzothiophen-5-yl)-4,4,5,5-tetramethyl-1,3-dioxolane (138 mg), potassium carbonate (129 mg) and (S)-tert-butyl 4-(1-amino-3-(4-iodophenyl)-1-oxopropan-2-ylcarbamoyl)tetrahydro-2H-pyran-4-ylcarbamate (Example 15, step (i), 242 mg) were stirred in acetonitrile (8 mL) and water (1 mL), and to the mixture was added 1,1 bis(di-tert-butylphosphino)ferrocene palladium dichloride (3 mg). The reaction mixture was heated at 80° C. for 3 h. The mixture was cooled to room temperature, concentrated under vacuum and the residue was partitioned between ethyl acetate and water. The ethyl acetate layer was washed with brine, dried over magnesium sulfate, filtered and concentrated to afford the sub-titled compound (260 mg).

m/e (MultiMode−) 556 [M−H]$^-$ (ii) tert-Butyl [4-({(1S)-1-cyano-2-[4-(2,2-dioxido-1,3-dihydro-2-benzothiophen-5-yl)phenyl]ethyl}carbamoyl)tetrahydro-2H-pyran-4-yl]carbamate

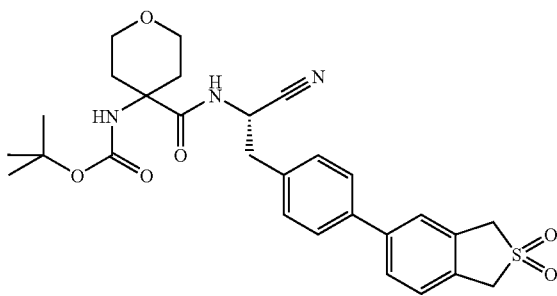

To N-α-({4-[(tert-butoxycarbonyl)amino]tetrahydro-2H-pyran-4-yl}carbonyl)-4-(2,2-dioxido-1,3-dihydro-2-benzothiophen-5-yl)phenylalaninamide (Example 34, step (i), 350 mg) in dichloromethane (5 mL) at room temperature was added Burgess' reagent (299 mg) and the mixture stirred for 18 h. The mixture was poured into water (30 mL) and extracted with dichloromethane (3×20 mL). The combined organic extracts were dried over magnesium sulfate and evaporated to afford the sub-titled compound (300 mg).

m/e (MultiMode−) 538 [M−H]⁻

4-Amino-N-{(1S)-1-cyano-2-[4-(2,2-dioxido-1,3-dihydro-2-benzothiophen-5-yl)phenyl]ethyl}tetrahydro-2H-pyran-4-carboxamide To tert-butyl [4-({(1S)-1-cyano-2-[4-(2,2-dioxido-1,3-dihydro-2-benzothiophen-5-yl)phenyl]ethyl}carbamoyl)tetrahydro-2H-pyran-4-yl]carbamate (Example 34, step (ii), 300 mg) was added formic acid (2 mL) and the mixture heated to 50° C. for 30 min. The mixture was allowed to cool to room temperature and then methanol (5 mL) was added and the mixture evaporated to give an oil. The crude mixture was purified by preparative HPLC (SunFire column) eluting with methanol/0.1% aqueous trifluoroacetic acid to afford a product which was then purified by chromatography on silica eluting with ethyl acetate to give the titled compound (82 mg).

¹H NMR (399.826 MHz, d₆-DMSO) δ 7.70-7.59 (m, 4H), 7.46 (d, 1H), 7.39 (d, 2H), 5.00 (t, 1H), 4.53 (d, 4H), 3.66-3.54 (m, 3H), 3.50-3.41 (m, 1H), 3.22-3.15 (m, 2H), 1.89 (ddd, 1H), 1.74 (ddd, 1H), 1.26-1.09 (m, 2H).

m/e (MultiMode+) 440 [M+H]⁺

ALTERNATIVE ROUTE TO EXAMPLE 3

(S)-4-Amino-N-(1-cyano-2-(4'-cyanobiphenyl-4-yl)ethyl)tetrahydro-2H-pyran-4-carboxamide

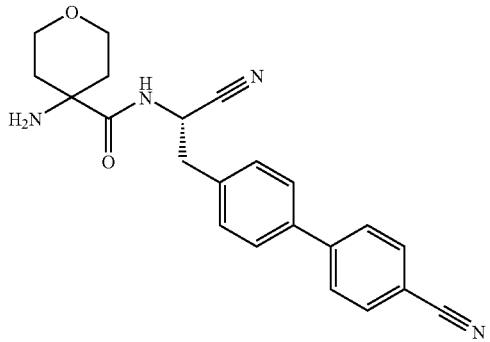

(i) (S)-tert-Butyl 4-(1-amino-3-(4-iodophenyl)-1-oxopropan-2-ylcarbamoyl)tetrahydro-2H-pyran-4-ylcarbamate (Example 1, step (iii))

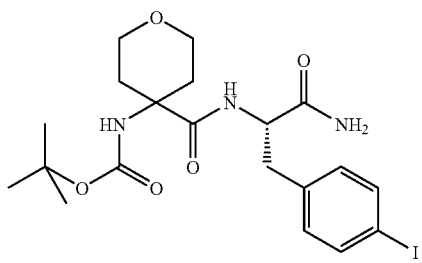

To a stirred suspension of 4-(tert-Butoxycarbonylamino)tetrahydro-2H-pyran-4-carboxylic acid, 20 g) in dimethylformamide was added (S)-2-amino-3-(4-iodophenyl)propanamide (Example 1, step (ii), 1.05 mol. eq.) and diisopropylethylamine (4 mol. eq.) at room temperature. The reaction mixture was cooled to 0-10° C. and stirred for 15 min. T3P (50% wt/wt in DMF; 1.7 mol. eq.) was added to the reaction mixture by dropwise addition at 0-10° C. over a period of 30 min and stirred for 1.5 h at the same temperature. The reaction mixture was quenched with water (2 rel. vol.) and stirred for 30 min at room temperature. 2-Methyltetrahydrofuran (15 rel. vol) and water (13 rel. vol) were added to the reaction mixture and extracted. The organic layer was separated and concentrated to 5 rel. vol. To the stirred organic portion was added toluene (10 rel. vol.) drop wise over a period of 30 min. The solution was stirred for 5 h at room temperature. The resulting solid material was filtered and washed with toluene (2 rel. vol), and dried the material at 50° C. under vacuum to afford the sub-titled compound (28.8 g).

¹H NMR (400 MHz, CDCl₃) δ 7.56 (d, 2H), 6.89 (d, 2H), 6.80 (brs, 1H), 6.35 (brs, 1H), 5.20 (s, 1H), 4.85 (s, 1H), 4.66 (dd, 1H), 3.81 (m, 1H), 3.63 (m, 1H), 3.49 (m, 2H), 3.07 (m, 2H), 2.22 (m, 1H), 1.77 (m, 2H), 1.47 (m, 1H), 1.29 (s, 9H).

(ii) (S)-tert-Butyl 4-(1-amino-3-(4'-cyanobiphenyl-4-yl)-1-oxopropan-2-ylcarbamoyl)tetrahydro-2H-pyran-4-ylcarbamate (Example 3, step (iv))

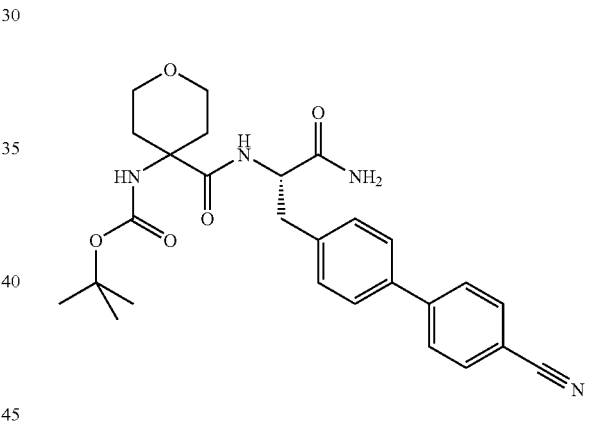

To a stirred solution of (S)-tert-butyl 4-(1-amino-3-(4-iodophenyl)-1-oxopropan-2-ylcarbamoyl)tetrahydro-2H-pyran-4-ylcarbamate (produced in step (i), 27 g) in 2-methyltetrahydrofuran (8 rel. vol.) was added 4-cyanophenyl boronic acid (1.1 mol. eq.), potassium carbonate (2 mol. eq.), water (2 rel. vol.) and 1,1 bis(di-tert-butylphosphino)ferrocene palladium dichloride (0.0065 mol. eq) at room temperature. Reaction mixture was heated to 78° C. and stirred for 10 h under nitrogen. The reaction mixture was cooled to room temperature and passed through a pad of celite. Water was added to the mixture and the layers separated. The organic layer was separated and concentrated to 5 rel. vol. under vacuum. The concentrated organic portion was stirred for 6 h at room temperature and the resulting solid filtered and washed with 2-methyltetrahydrofuran (2 rel. vol.). The solid was dried at 50° C. under vacuum to afford the sub-titled compound (17.3 g).

¹H NMR (400 MHz, d₆-DMSO) δ 7.89 (dd, 4H), 7.71 (m, 1H), 7.64 (d, 2H), 7.27 (m, 5H), 4.50 (m, 1H), 3.56 (m, 1H), 3.41 (m, 1H), 3.21 (m, 2H), 2.93 (m, 1H), 1.94 (m, 1H), 1.61 (m, 3H), 1.35 (s, 9H).

(iii) (S)-tert-Butyl 4-(1-cyano-2-(4'-cyanobiphenyl-4-yl)ethylcarbamoyl)tetrahydro-2H-pyran-4-ylcarbamate (Example 3, step (v))

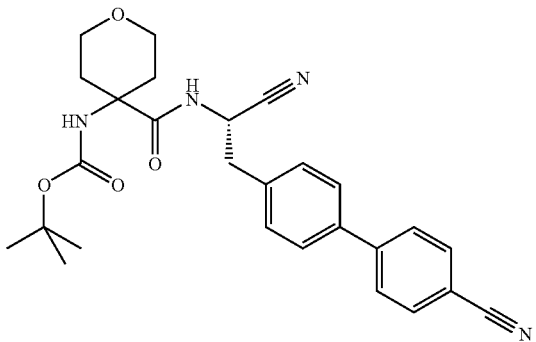

To a solution of (S)-tert-butyl 4-(1-amino-3-(4'-cyanobiphenyl-4-yl)-1-oxopropan-2-ylcarbamoyl)tetrahydro-2H-pyran-4-ylcarbamate (produced in step (ii), 35 g) in DMF (2.5 rel. vol.) at room temperature was added diisopropylethylamine (4 mol. eq.) and T3P in DMF (50% wt/wt in DMF, 3 mol. eq.) under nitrogen. The resulting mixture was heated to 68° C. for 2 h. The reaction mixture was cooled to room temperature and quenched by dropwise addition of water (3 rel. vol.). The reaction mixture was stirred for 30 min and 2-methyltetrahydrofuran (15 rel. vol.) was added. The organic layer was washed with water (2×5 rel. vol.) followed is by saturated aqueous sodium hydrogen carbonate solution. The separated organic layer was concentrated to 10 rel. vol. under reduced pressure and then heated to 55° C. after which n-heptane (5 rel. vol.) was slowly added over a period of 15 min. The mixture was stirred for 30 min at 55° C. and then filtered, washed with n-heptane (2 rel. vol.) and dried at 50° C. to afford the sub-titled compound (26.2 g).

$^1$H NMR (400 MHz, CDCl$_3$) δ 7.63 (dd, 4H), 7.51 (d, 2H), 7.34 (d, 2H), 5.07 (m, 1H), 4.66 (s, 1H), 3.60 (m, 4H), 3.07 (m, 2H), 2.09 (m, 2H), 1.90 (m, 1H), 1.74 (m, 1H), 1.36 (s, 9H).

EXAMPLE 3

(S)-4-Amino-N-(1-cyano-2-(4'-cyanobiphenyl-4-yl)ethyl)tetrahydro-2H-pyran-4-carboxamide (Alternative Route)

To (S)-tert-butyl 4-(1-cyano-2-(4'-cyanobiphenyl-4-yl)ethylcarbamoyl)tetrahydro-2H-pyran-4-ylcarbamate (produced in step (iii), 5 g) was added formic acid (6 rel. vol.) at room temperature and the mixture heated to 40° C. The reaction mixture was stirred for 1.5 h at 40° C. and then cooled to 0-8° C. and quenched with water (5 rel. vol.). The reaction mixture was diluted with 2-methyltetrahydrofuran (10 rel. vol.) and 2N NaOH solution added dropwise at 0-8° C. until the pH reached 6.7. The reaction mixture was further diluted with 2-2-methyltetrahydrofuran (10 rel. vol.) and extracted. The organic layer was separated and concentrated to 8 rel. vol. under vacuum. The mixture was stirred the concentrated for 1 h at room temperature and the resulting solid was filtered and washed with 2-methyltetrahydrofuram (1 rel. vol.) to afford the titled compound (2.0 g).

$^1$H NMR (400 MHz, d$_6$-DMSO) δ 7.96 (dd, 4H), 7.78 (d, 2H), 7.49 (d, 2H), 5.08 (t, 1H), 3.65 (m, 3H), 3.51 (m, 1H), 3.27 (m, 2H), 1.95 (m, 1H), 1.78 (m, 1H), 1.43 (m, 1H), 1.22 (m, 2H).

Physical Form Data

Instrument Details:

XRPD—PANalytical CubiX PRO machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the Forms of the present invention are not limited to the crystals that provide X-ray powder diffraction patterns identical to the X-ray powder diffraction pattern shown in FIGS. 1 to 7 and any crystals providing X-ray powder diffraction patterns substantially the same as those shown in FIGS. 1 to 7 fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta. Typically plus or minus 0.2° 2-theta. Such degree of a measurement error should be taken into account when considering the X-ray powder diffraction patterns in FIGS. 1 to 7 and when reading the Tables. Furthermore, it should be understood that intensities might fluctuate depending on experimental conditions and sample preparation (preferred orientation).

PREPARATION OF EXAMPLE 3

(S)-4-Amino-N-(1-cyano-2-(4'-cyanobiphenyl-4-yl)
ethyl)tetrahydro-2H-pyran-4-carboxamide (Type 1)

To (S)-tert-butyl 4-(1-cyano-2-(4'-cyanobiphenyl-4-yl) ethylcarbamoyl)tetrahydro-2H-pyran-4-ylcarbamate (Example 3, step (v), 420 mg) was added formic acid (2 mL) and the mixture heated to 50° C. for 10 min. The mixture was evaporated to dryness, dissolved in methanol (4 mL) and purified on reverse phase HPLC (Water's sunfire column) eluting with a gradient of acetonitrile in 0.1% aqueous trifluoroacetic acid. Fractions containing product were evaporated to remove acetonitrile, neutralised with saturated sodium bicarbonate and extracted with dichloromethane which was dried over magnesium sulfate and evaporated to afford the titled compound (110 mg).

$^1$H NMR (399.824 MHz, CDCl$_3$) δ 8.28 (d, 1H), 7.73 (dd, 2H), 7.67 (d, 2H), 7.59 (d, 2H), 7.40 (d, 2H), 5.13 (dt, 1H), 3.94-3.82 (m, 2H), 3.66-3.56 (m, 2H), 3.17 (d, 2H), 2.34-2.24 (m, 1H), 2.23-2.13 (m, 1H), 1.49 (s, 2H), 1.30 (dq, 1H), 1.20 (dq, 1H).

m/e (MultiMode+) 375 [M+H]$^+$

ANALYSIS OF EXAMPLE 3

(S)-4-Amino-N-(1-cyano-2-(4'-cyanobiphenyl-4-yl)
ethyl)tetrahydro-2H-pyran-4-carboxamide (Type 1)

Figure 1:
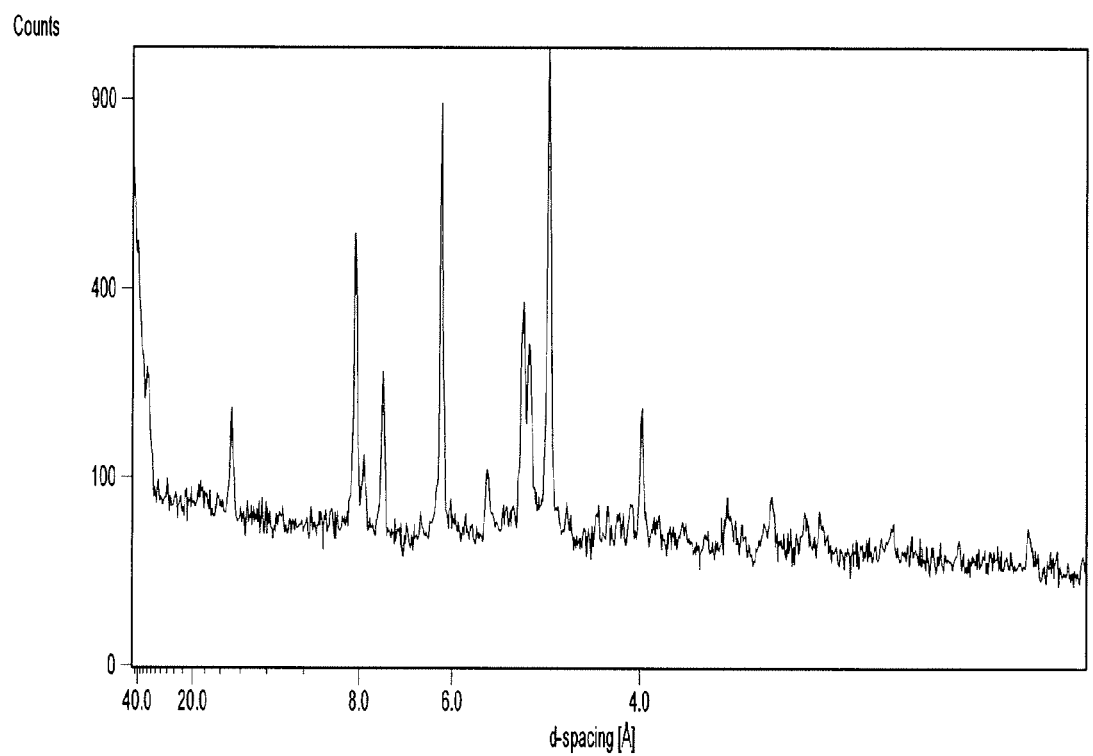
FIG. 1: X-ray powder diffraction pattern of Type 1 of Example 3

A sample of crystalline Example 3 Type 1 obtained by the procedure described above was analysed by XRPD. An XRPD spectrum of Example 3 Type 1 is presented in FIG. 1.

| Pos. [°2Th.] | d-spacing [Å] |
|---|---|
| 10.9 | 8.1 |
| 12.0 | 7.4 |
| 14.3 | 6.2 |
| 17.6 | 5.0 |
| 18.6 | 4.8 |

Table 1 Some characteristic peaks for Example 3 Type 1.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least one peak with a 2-theta values selected from the following 2-theta values measured using radiation with a wavelength of 1.5418 Å: 10.9, 12.0, 14.3, 17.6 and 18.6. In one aspect the invention relates to a crystalline form of a (S)-4-amino-N-(1-cyano-2-(4'-cyanobiphenyl-4-yl)ethyl)tetrahydro-2H-pyran-4-carboxamide having an X-ray diffraction pattern with at least 2 peaks with 2-theta values selected from the following 2-theta values measured using radiation with a wavelength of 1.5418 Å: 10.9, 12.0, 14.3, 17.6 and 18.6. In one aspect the invention relates to a crystalline form of a (S)-4-amino-N-(1-cyano-2-(4'cyanobiphenyl-4-yl)ethyl)tetrahydro-2H-pyran-4-carboxamide having an X-ray diffraction pattern with at least one peak with a d value selected from the following d-values 8.1, 7.4, 6.2, 5.0 and 4.8 Å.

In one aspect the invention relates to a crystalline form of a (S)-4-amino-N-(1-cyano-2-(4'cyanobiphenyl-4-yl)ethyl)tetrahydro-2H-pyran-4-carboxamide having an X-ray diffraction pattern with at least 2 peaks with a d value selected from the following d-values 8.1, 7.4, 6.2, 5.0 and 4.8 Å.

PREPARATION OF EXAMPLE 3

(S)-4-Amino-N-(1-cyano-2-(4'-cyanobiphenyl-4-yl)
ethyl)tetrahydro-2H-pyran-4-carboxamide (Type 3)

(S)-4-Amino-N-(1-cyano-2-(4'-cyanobiphenyl-4-yl) ethyl)tetrahydro-2H-pyran-4-carboxamide (Example 3, 60 mg) was dissolved in acetonitrile (1 mL) and water (0.2 mL) and stirred at room temperature for 48 h whilst the solvent was slowly allowed to evaporate to dryness. The resultant white solid was collected and dried in a vacuum oven at 40° C. for 72 h to give the titled compound (45 mg).

m/e (MultiMode+) 375 [M+H]$^+$

ANALYSIS OF EXAMPLE 3

(S)-4-Amino-N-(1-cyano-2-(4'-cyanobiphenyl-4-yl)
ethyl)tetrahydro-2H-pyran-4-carboxamide (Type 3)

Figure 2:
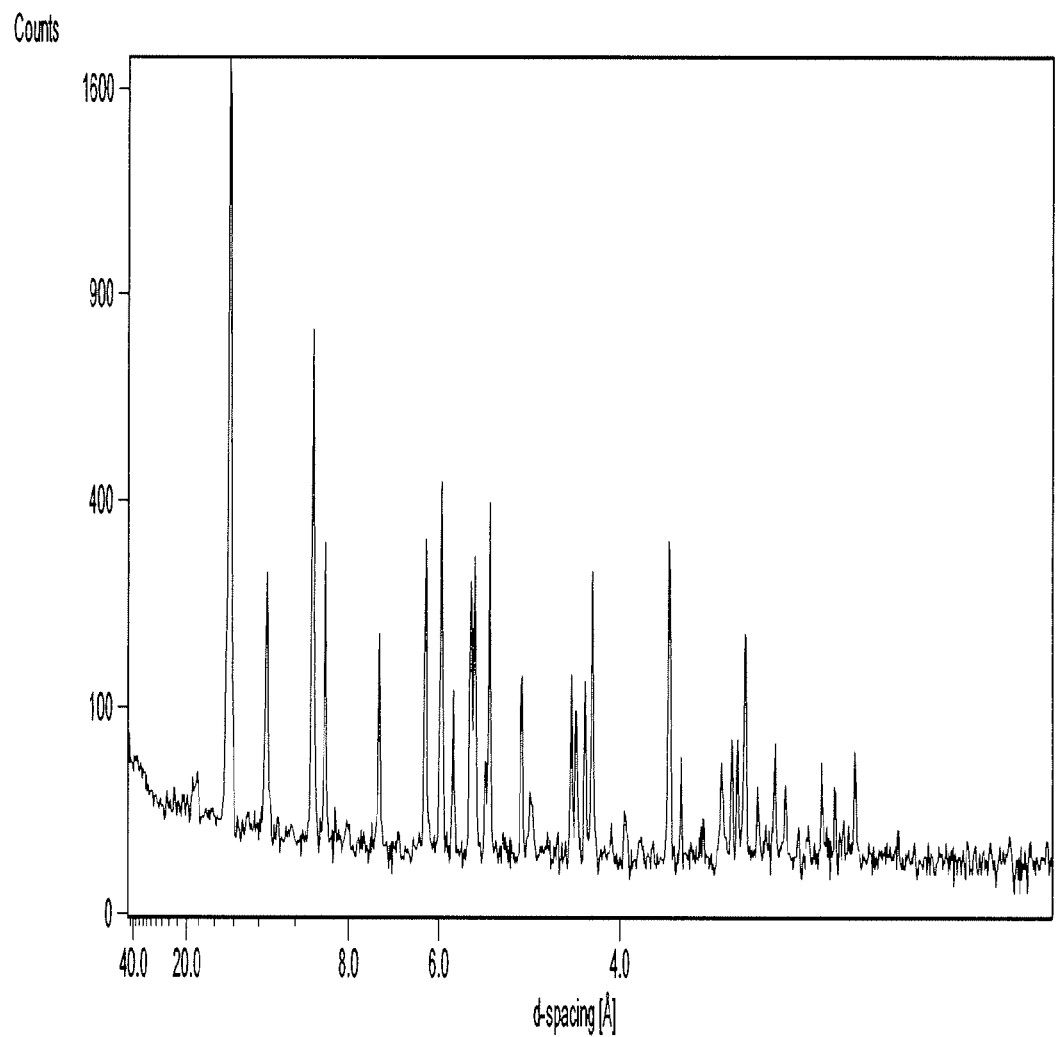
FIG. 2: X-ray powder diffraction pattern of Type 3 of Example 3

A sample of crystalline Example 3 Type 3 obtained by the procedure described above was analysed by XRPD. An XRPD spectrum of Example 3 Type 3 is presented in FIG. 2.

| Pos. [°2Th.] | d-spacing [Å] |
|---|---|
| 6.1 | 14.4 |
| 9.6 | 9.2 |
| 14.8 | 6.0 |
| 16.8 | 5.3 |
| 24.2 | 3.7 |

Table 2 Some characteristic peaks for Example 3 Type 3.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least one peak with a 2-theta value selected from the following 2-theta values measured using radiation with a wavelength of 1.5418 Å: 6.1, 9.6, 14.8, 16.8 and 24.2. In one aspect the invention relates to a crystalline form of a (S)-4-amino-N-(1-cyano-2-(4'-cyanobiphenyl-4-yl)ethyl)tetrahydro-2H-pyran-4-carboxamide having an X-ray diffraction pattern with at least 2 peaks with 2-theta values selected from the following 2-theta values measured using radiation with a wavelength of 1.5418 Å: 6.1, 9.6, 14.8, 16.8 and 24.2. In one aspect the invention relates to a crystalline form of a (S)-4-amino-N-(1-cyano-2-(4'-cyanobiphenyl-4-yl)ethyl)tetrahydro-2H-pyran-4-carboxamide having an X-ray diffraction pattern with at least one peak with a d-value selected from the following d-values 14.4, 9.2, 6.0, 5.3 and/or 3.7 Å.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least 2 peaks with d-values selected from the following d-values 14.4, 9.2, 6.0, 5.3 and/or 3.7 Å.

PREPARATION OF EXAMPLE 3

(S)-4-Amino-N-(1-cyano-2-(4'-cyanobiphenyl-4-yl)
ethyl)tetrahydro-2H-pyran-4-carboxamide (Type 2
Form A)

Formic acid (150 mL) was heated and stirred at 50° C. and (S)-tert-butyl 4-(1-cyano-2-(4'-cyanobiphenyl-4-yl)ethylcarbamoyl)tetrahydro-2H-pyran-4-ylcarbamate (Example 3, step (v), 36.5 g) was added portionwise over 5 min. The resulting solution was then stirred at 50° C. for 20 mins. The reaction mixture was concentrated under reduced pressure and the residual oil was diluted with ice/water (500 mL) and the solution basified with saturated aqueous sodium bicarbonate. The mixture was the extracted with dichloromethane (3×500 mL), and the combined extracts dried over magnesium sulphate. The residue after evaporation afforded a brown solid which was purified using chromatography on silica eluting with ethyl acetate. After crystallisation from acetonitrile/diethyl ether a colourless solid 12 g was produced. The filtrate and mixed column fractions were collected and concentrated and the residue again purified by chromatography on silica eluting with acetonitrile to afford a solid (3.9 g). All filtrates and mixed fractions were combined and concentrated to dryness. The residue was treated with formic acid (20 mL) at 50° C. to ensure full deprotection had occurred. The cooled reaction mixture was diluted with water and the solution made basic with '880' ammonia. The precipitated product was extracted into dichloromethane (300 mL) and the organic extract dried and concentrated to dryness. The residue was chromatographed on silica gel eluting with acetonitrile to give a product which was recrystallised from acetonitrile/diethyl ether (1:4) to afford a solid 1.7 g.

The 12 g batch and the 3.9 g batch were combined and recrystallised by dissolving in hot acetonitrile (75 mL) and then adding diethyl ether (~350 mL) slowly to the solution. The solution was left in the refrigerator for 18 h and the crystals collected by filtration (14.7 g). A further recrystallisation of this material was carried out using the minimum amount of tetrahydrofuran (~150 mL) which gave 10.6 g of colourless crystals. The filtrate from this recrystallisation was concentrated to dryness and the residue recrystallised from tetrahydrofuran to give a further 3.2 g of material. Both batches of material (10.6 g and 3.2 g) were suspended in a mixture of ethanol/water (1:5) (25 mg/mL) and stirred at room temperature for 24 h. The suspension was filtered and the resulting solid dried to afford 10.5 g and 2.7 g respectively Data for 10.5 g Batch.

m/e (MultiMode+) 375 [M+H]+

ANALYSIS OF EXAMPLE 3

(S)-4-Amino-N-(1-cyano-2-(4'-cyanobiphenyl-4-yl)ethyl)tetrahydro-2H-pyran-4-carboxamide (Type 2 Form A)

Figure 3:
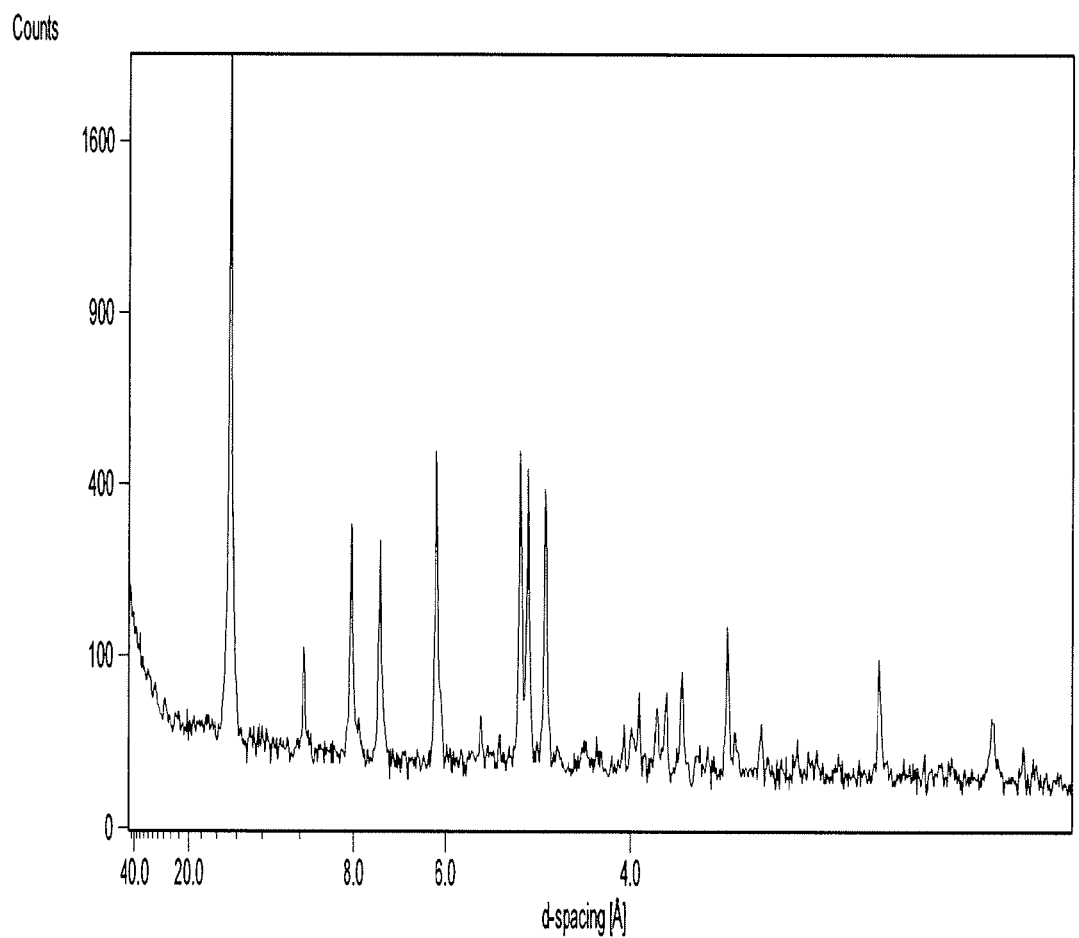
FIG. 3: X-ray powder diffraction pattern of Type 2 Form A of Example 3

A sample of crystalline Example 3 Type 2 Form A obtained by the procedure described above was analysed by XRPD. An XRPD spectrum of Example 3 Type 2 Form A is presented in FIG. 3.

| Pos. [°2Th.] | d-spacing [Å] |
|---|---|
| 4.8 | 18.3 |
| 11.0 | 8.0 |
| 14.4 | 6.1 |
| 14.6 | 6.0 |
| 16.7 | 5.3 |
| 16.9 | 5.2 |
| 17.4 | 5.1 |

Table 3 Some characteristic peaks for Example 3 Type 2 Form A.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least one peak with a 2-theta value selected from the following 2-theta values measured using radiation with a wavelength of 1.5418 Å: 4.8, 11.0, 14.4, 14.6, 16.7, 16.9 and 17.4.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least 2 peaks with 2-theta values selected from the following 2-theta values measured using radiation with a wavelength of 1.5418 Å: 4.8, 11.0, 14.4, 14.6, 16.7, 16.9 and 17.4.

In one aspect the invention relates to a crystalline form of a (S)-4-amino-N-(1-cyano-2-(4'-cyanobiphenyl-4-yl)ethyl) tetrahydro-2H-pyran-4-carboxamide having an X-ray diffraction pattern with at least one peak with a d-value selected from the following d-values 18.3, 8.0, 6.1, 6.0, 5.3, 5.2 and 5.1 Å.

cyanobiphenyl-4-yl)ethyl)tetrahydro-2H-pyran-4-carboxamide having an X-ray diffraction pattern with at least 2 peaks with d-value selected from the following d-values 18.3, 8.0, 6.1, 6.0, 5.3, 5.2 and 5.1 Å.

PREPARATION OF EXAMPLE 3

(S)-4-Amino-N-(1-cyano-2-(4'-cyanobiphenyl-4-yl)ethyl)tetrahydro-2H-pyran-4-carboxamide (Type 4 Dioxane solvate)

(S)-4-Amino-N-(1-cyano-2-(4'-cyanobiphenyl-4-yl)ethyl)tetrahydro-2H-pyran-4-carboxamide (Example 3, 13 mg) was dissolved in 100 µL of 1,4-dioxane, forming a clear solution. The solution was stirred for 3 days at room temperature (some evaporation of the solvent may have occurred) after which time a solid precipitated. The solid phase was separated by centrifugation.

ANALYSIS OF EXAMPLE 3

(S)-4-Amino-N-(1-cyano-2-(4'-cyanobiphenyl-4-yl)ethyl)tetrahydro-2H-pyran-4-carboxamide (Type 4 Dioxane solvate)

Figure 4:
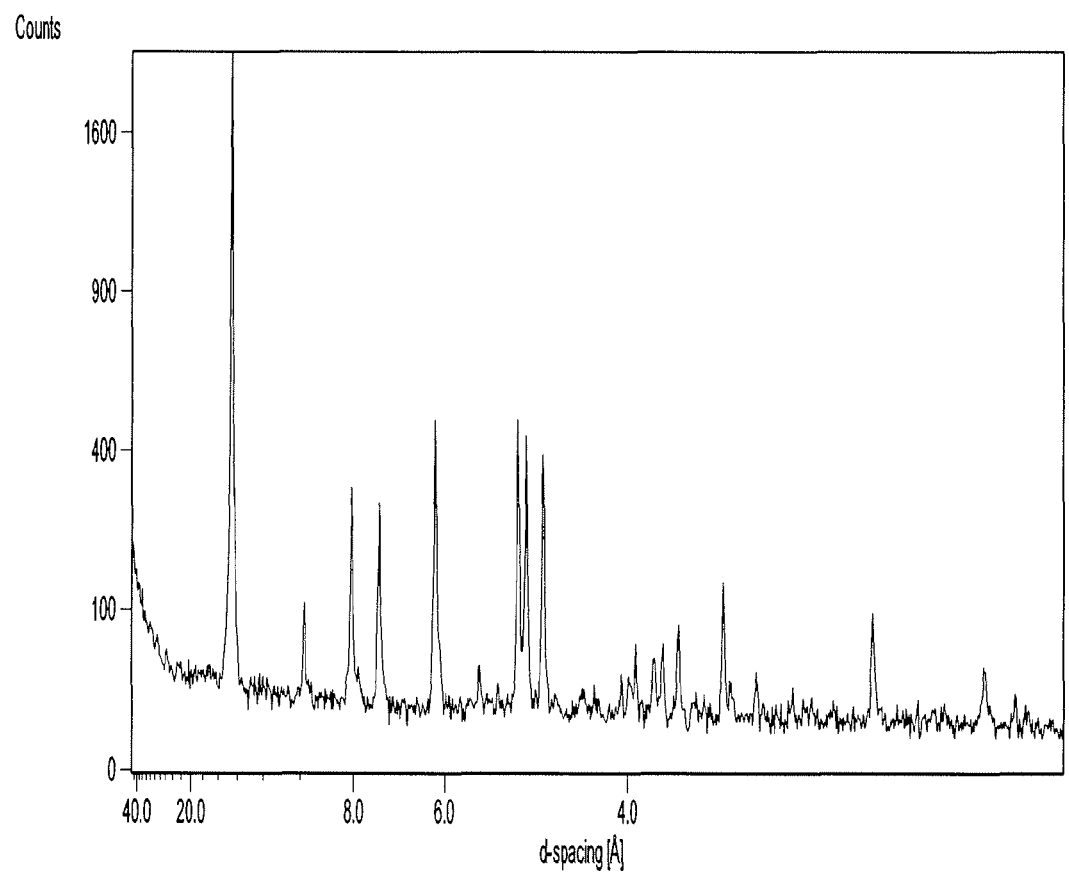
FIG. 4: X-ray powder diffraction pattern of Type 4 (Dioxane solvate) of Example 3

A sample of crystalline Example 3 Type 4 dioxane solvate obtained by the procedure described above was analysed by XRPD. An XRPD spectrum of Example 3 Type 4 dioxane solvate is presented in FIG. 4.

| Pos. [°2Th.] | d-spacing [Å] |
|---|---|
| 6.1 | 14.6 |
| 10.9 | 8.1 |
| 12.1 | 7.3 |
| 17.7 | 5.0 |
| 18.1 | 4.9 |
| 18.8 | 4.7 |

Table 4 Some characteristic peaks for Example 3 Type 4 dioxane solvate.

In one aspect the invention relates to a crystalline form of a (S)-4-amino-N-(1-cyano-2-(4'-cyanobiphenyl-4-yl)ethyl) tetrahydro-2H-pyran-4-carboxamide dioxane solvate having an X-ray diffraction pattern with at least one peak with a 2-theta value selected from the following 2-theta values measured using radiation with a wavelength of 1.5418 Å: 6.1, 10.9, 12.1, 17.7, 18.1 and 18.8.

In one aspect the invention relates to a crystalline form of a (S)-4-amino-N-(1-cyano-2-(4'-cyanobiphenyl-4-yl)ethyl) tetrahydro-2H-pyran-4-carboxamide dioxane solvate having an X-ray diffraction pattern with at least 2 peaks with 2-theta values selected from the following 2-theta values measured using radiation with a wavelength of 1.5418 Å: 6.1, 10.9, 12.1, 17.7, 18.1 and 18.8.

In one aspect the invention relates to a crystalline form of a (S)-4-amino-N-(1-cyano-2-(4'-cyanobiphenyl-4-yl)ethyl) tetrahydro-2H-pyran-4-carboxamide dioxane solvate having an X-ray diffraction pattern with at least one peak with a d-value selected from the following d-values 14.6, 8.1, 7.3, 5.0, 4.9 and 4.7 Å.

In one aspect the invention relates to a crystalline form of a (S)-4-amino-N-(1-cyano-2-(4'-cyanobiphenyl-4-yl)ethyl) tetrahydro-2H-pyran-4-carboxamide dioxane solvate having an X-ray diffraction pattern with at least 2 peaks with d-values selected from the following d-values 14.6, 8.1, 7.3, 5.0, 4.9 and 4.7 Å.

PREPARATION OF EXAMPLE 4

(S)-4-Amino-N-(1-cyano-2-(4'-fluorobiphenyl-4-yl) ethyl)tetrahydro-2H-pyran-4-carboxamide (Form A)

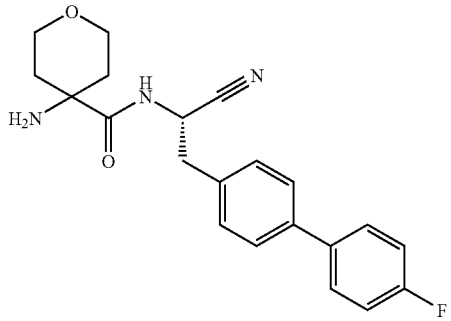

To (S)-tert-butyl 4-(1-cyano-2-(4'-fluorobiphenyl-4-yl) ethylcarbamoyl)tetrahydro-2H-pyran-4-ylcarbamate (Example 4, step (ii(i)), 663 mg) was added formic acid (8.1 mL) and the mixture heated to 50° C. for 20 min. The mixture was evaporated to dryness, dissolved in methanol (10 mL), re-evaporated to dryness, dissolved in dichloromethane and evaporated again. The crude product was purified by preparative HPLC (Waters X-Bridge column) using a gradient of methanol in aqueous 0.1% trifluoroacetic acid as eluent. The fractions containing the purified product were combined, evaporated and then dissolved in dichloromethane and washed with saturated aqueous sodium hydrogen carbonate solution. The organic layer was dried over magnesium sulfate and evaporated to dryness to afford a solid (392 mg). The solid (384 mg) was suspended in water (12.8 mL) and ethanol (2.56 mL) and stirred at ambient temperature for 66 hours. The suspension was filtered and the solid dried under vacuum to afford the titled compound (358 mg) which was contaminated with an impurity. The material was re-purified by preparative HPLC (Waters X-Bridge column) using a gradient of methanol in aqueous 0.1% trifluoroacetic acid as eluent. The fractions containing the desired compound were combined, evaporated and then dissolved in dichloromethane and washed with saturated aqueous sodium hydrogen carbonate solution. The organic layer was dried over magnesium sulfate and evaporated, then triturated with diethyl ether and evaporated again to afford a white solid (281 mg). The solid (277 mg) was suspended in a mixture of water (9.2 mL) and acetonitrile (0.5 mL) and stirred at ambient temperature for 19 h. The solid was collected by filtration and then dried under vacuum to afford the titled compound (266 mg).

$^1$H NMR (399.824 MHz, $d_6$-DMSO) δ 7.78-7.63 (m, 2H), 7.60 (d, 2H), 7.37 (d, 2H), 7.34-7.22 (m, 2H), 4.99 (t, 1H), 3.69-3.52 (m, 3H), 3.46 (dt, 1H), 3.27-3.10 (m, 2H), 1.89 (ddd, 1H), 1.74 (ddd, 1H), 1.17 (ddd, 2H).

m/e (MultiMode+) 368 [M+H]$^+$

ANALYSIS OF EXAMPLE 4

(S)-4-Amino-N-(1-cyano-2-(4'-fluorobiphenyl-4-yl) ethyl)tetrahydro-2H-pyran-4-carboxamide (Form A)

Figure 5:
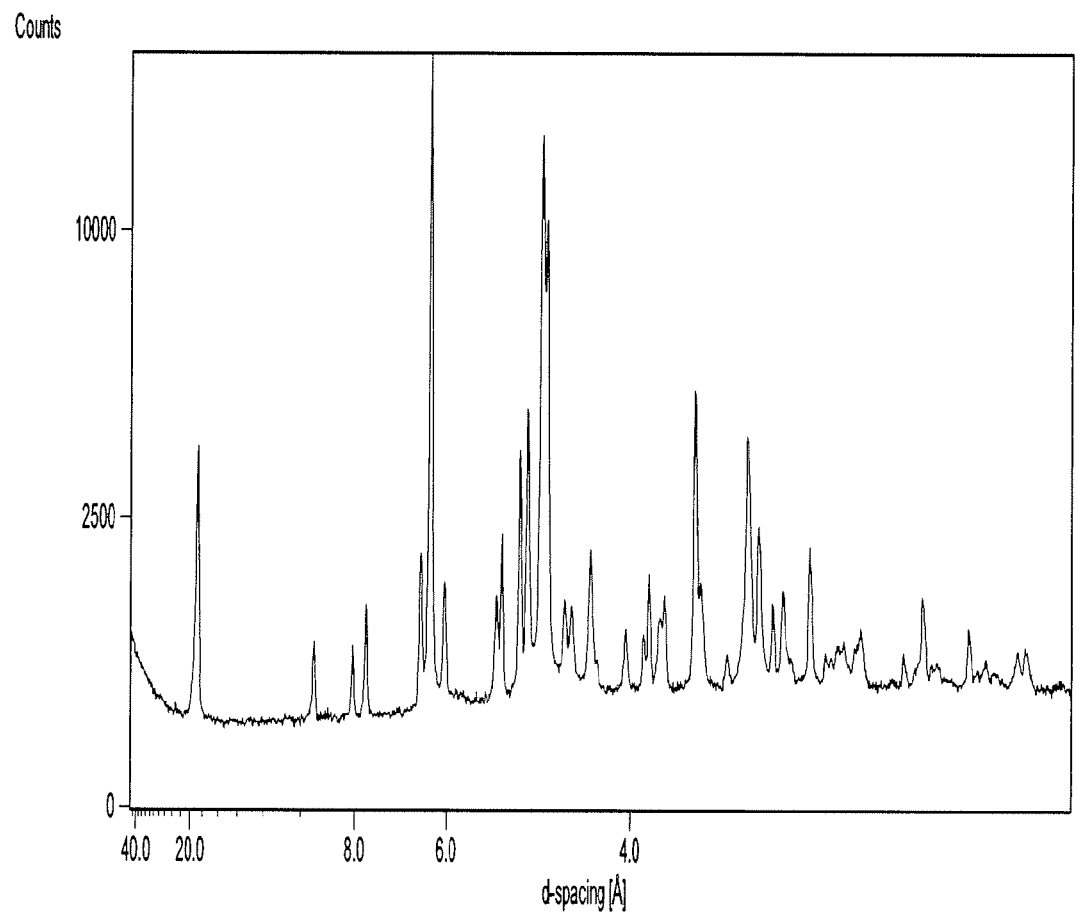
FIG. 5: X-ray powder diffraction pattern of Form A of Example 4

A sample of crystalline Example 4 Form A obtained by the procedure described above was analysed by XRPD. An XRPD spectrum of Example 4 Form A is presented in FIG. 5.

| Pos. [°2Th.] | d-spacing [Å] |
| --- | --- |
| 4.7 | 18.8 |
| 14.1 | 6.3 |
| 17.7 | 5.0 |
| 18.0 | 4.9 |
| 24.8 | 3.6 |

Table 5 Some characteristic peaks for Example 4 Form A.

In one aspect the invention relates to a crystalline form of a (S)-4-amino-N-(1-cyano-2-(4'-fluorobiphenyl-4-yl)ethyl) tetrahydro-2H-pyran-4-carboxamide having an X-ray diffraction pattern with at least one peak with a 2-theta value selected from the following 2-theta values measured using radiation with a wavelength of 1.5418 Å: 4.7, 14.1, 17.7, 18.0 and 24.8.

In one aspect the invention relates to a crystalline form of a (S)-4-amino-N-(1-cyano-2-(4'-fluorobiphenyl-4-yl)ethyl) tetrahydro-2H-pyran-4-carboxamide having an X-ray diffraction pattern with at least 2 peaks with 2-theta values selected from the following 2-theta values measured using radiation with a wavelength of 1.5418 Å: 4.7, 14.1, 17.7, 18.0 and 24.8.

In one aspect the invention relates to a crystalline form of a ((S)-4-amino-N-(1-cyano-2-(4'-fluorobiphenyl-4-yl)ethyl) tetrahydro-2H-pyran-4-carboxamide having an X-ray diffraction pattern with at least one peak with a d-value selected from the following d-values 18.8, 6.3, 5.0, 4.9 and/or 3.6 Å.

In one aspect the invention relates to a crystalline form of a ((S)-4-amino-N-(1-cyano-2-(4'-fluorobiphenyl-4-yl)ethyl) tetrahydro-2H-pyran-4-carboxamide having an X-ray diffraction pattern with at least 2 peaks with d-values selected from the following d-values 18.8, 6.3, 5.0, 4.9 and/or 3.6 Å.

PREPARATION OF EXAMPLE 6

(S)-4'-(2-(4-Aminotetrahydro-2H-pyran-4-carboxamido)-2-cyanoethyl)biphenyl-4-yl methanesulfonate (Form A)

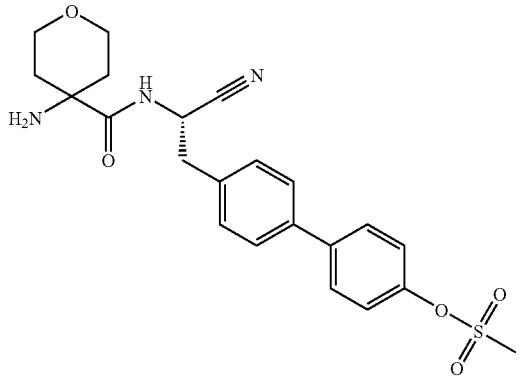

To (S)-4'-(2-(4-(tert-butoxycarbonylamino)tetrahydro-2H-pyran-4-carboxamido)-2-cyanoethyl)biphenyl-4-yl-methanesulfonate (Example 6, step (ii), 708 mg) was added formic acid (7.5 mL) and the mixture heated to 50° C. for 20 min. The mixture was cooled and evaporated to dryness, dissolved in methanol (10 mL), re-evaporated to dryness and this process repeated. The crude product was purified by preparative HPLC (Waters X-Bridge column) using a gradient of methanol in aqueous 0.1% trifluoroacetic acid as eluent. The fractions containing the desired compound were combined, evaporated and the residue dissolved in dichloromethane and washed with saturated aqueous sodium hydrogen carbonate solution. The organics were dried over magnesium sulfate, evaporated to dryness and then triturated with diethyl ether to afford a solid (463 mg). The solid (458 mg) was suspended in water (15.4 mL) and acetonitrile (0.7 mL) and stirred at ambient temperature for 19 hours. The suspension was filtered and the solid dried under vacuum at 45° C. to the titled compound (423 mg).

$^1$H NMR (400 MHz, d$_6$-DMSO) δ 7.83-7.70 (m, 2H), 7.64 (d, 2H), 7.48-7.36 (m, 4H), 5.01 (t, 1H), 3.69-3.52 (m, 3H), 3.46 (dt, 1H), 3.41 (s, 3H), 3.25-3.08 (m, 2H), 1.89 (ddd, 1H), 1.74 (ddd, 1H), 1.17 (dd, 2H).

m/e (MultiMode+) 444 [M+H]$^+$

ANALYSIS OF EXAMPLE 6

(S)-4'-(2-(4-Aminotetrahydro-2H-pyran-4-carboxamido)-2-cyanoethyl)biphenyl-4-yl methanesulfonate (Form A)

Figure 6:
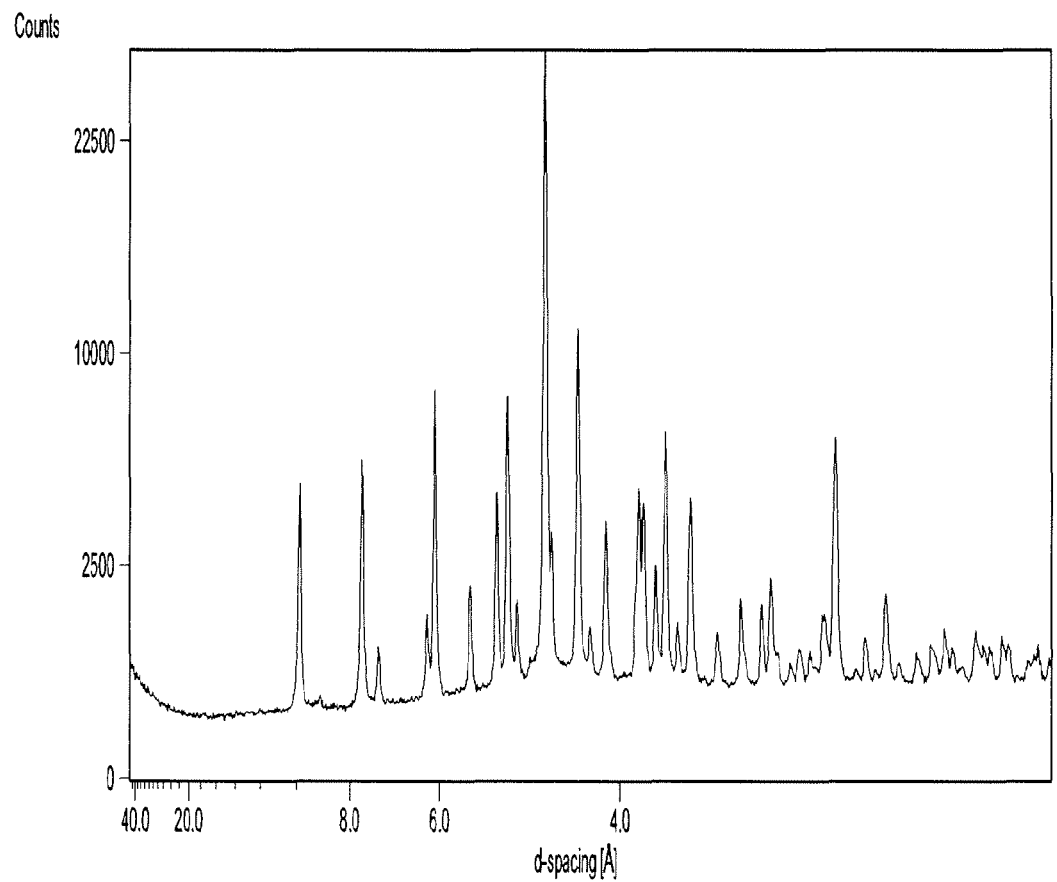
FIG. 6: X-ray powder diffraction pattern of Form A of Example 6

A sample of crystalline Example 6 Form A obtained by the procedure described above was analysed by XRPD. An XRPD spectrum of Example 6 Form A is presented in FIG. 6.

| Pos. [°2Th.] | d-spacing [Å] |
|---|---|
| 17.6 | 5.1 |
| 19.1 | 4.6 |
| 20.5 | 4.3 |
| 24.1 | 3.7 |
| 31.1 | 2.9 |

Table 6 Some characteristic peaks for Example 6 Form A.

In one aspect the invention relates to a crystalline form of a (S)-4'-(2-(4-Aminotetrahydro-2H-pyran-4-carboxamido)-2-cyanoethyl)biphenyl-4-ylmethanesulfonate having an X-ray diffraction pattern with at least one peak with a 2-theta value selected from the following 2-theta values measured using radiation with a wavelength of 1.5418 Å: 17.6, 19.1, 20.5, 24.1 and 31.1.

In one aspect the invention relates to a crystalline form of a (S)-4'-(2-(4-Aminotetrahydro-2H-pyran-4-carboxamido)-2-cyanoethyl)biphenyl-4-ylmethanesulfonate having an X-ray diffraction pattern with at least 2 peaks with 2-theta values selected from the following 2-theta values measured using radiation with a wavelength of 1.5418 Å: 17.6, 19.1, 20.5, 24.1 and 31.1.

In one aspect the invention relates to a crystalline form of a (S)-4'-(2-(4-Aminotetrahydro-2H-pyran-4-carboxamido)-2-cyanoethyl)biphenyl-4-ylmethanesulfonate having an X-ray diffraction pattern with at least one peak with a d-value selected from the following d-values 5.1, 4.6, 4.3, 3.7 and/or 2.9 Å.

In one aspect the invention relates to a crystalline form of a (S)-4'-(2-(4-Aminotetrahydro-2H-pyran-4-carboxamido)-2-cyanoethyl)biphenyl-4-ylmethanesulfonate having an X-ray diffraction pattern with at least 2 peaks with d-values selected from the following d-values 5.1, 4.6, 4.3, 3.7 and/or 2.9 Å.

PREPARATION OF EXAMPLE 25

(S)-4-Amino-N-(2-(4'-carbamoyl-3'-fluorobiphenyl-4-yl)-1-cyanoethyl)tetrahydro-2H-pyran-4-carboxamide (Form A)

(S)-4-Amino-N-(2-(4'-carbamoyl-3'-fluorobiphenyl-4-yl)-1-cyanoethyl)tetrahydro-2H-pyran-4-carboxamide (Example 25, 212 mg) was suspended in acetonitrile (353 μL) and water (6.7 mL) and stirred under nitrogen at room temperature for 17.5 h. The solid was collected by filtration and dried under vacuum to give the titled compound as a solid (205 mg).

ANALYSIS OF EXAMPLE 25

(S)-4-Amino-N-(2-(4'-carbamoyl-3'-fluorobiphenyl-4-yl)-1-cyanoethyl)tetrahydro-2H-pyran-4-carboxamide (Form A)

Figure 7:
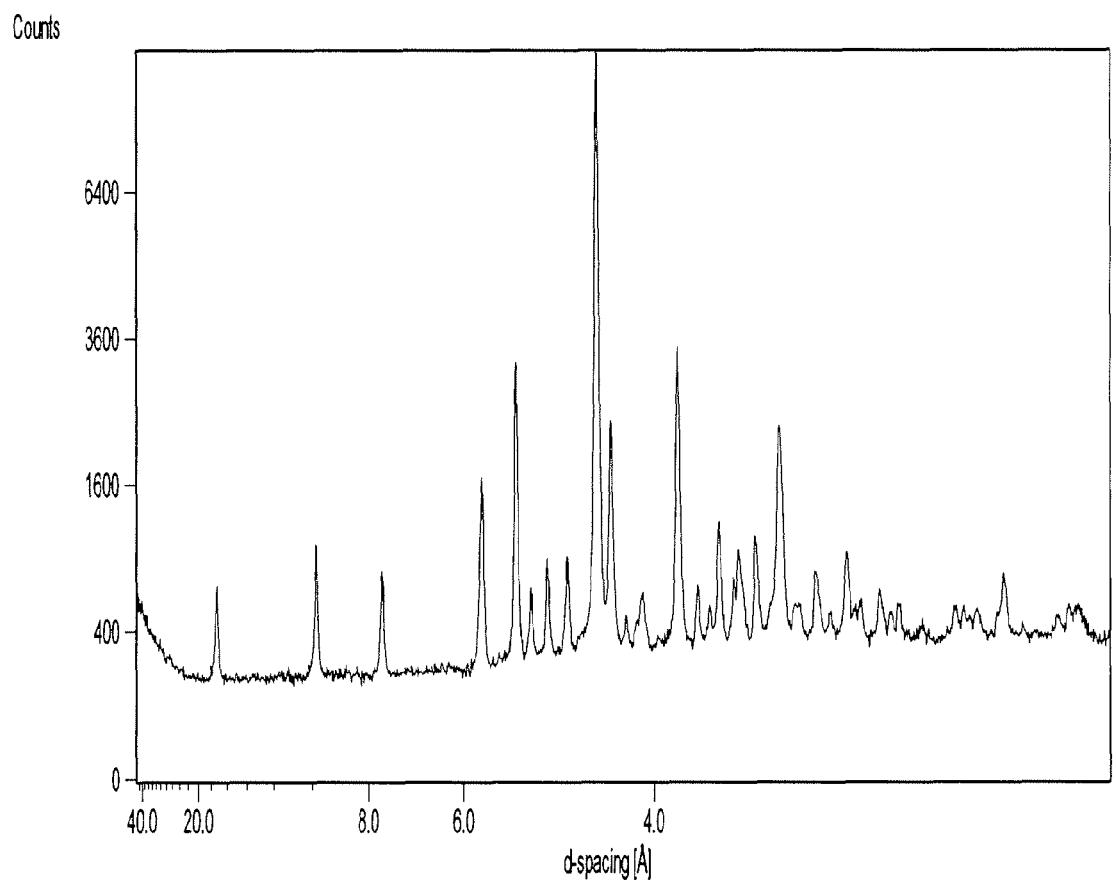
FIG. 7: X-ray powder diffraction pattern of Form A of Example 25

A sample of crystalline Example 25 Form A obtained by the procedure described above was analysed by XRPD. An XRPD spectrum of Example 25 Form A is presented in FIG. 7.

| Pos. [°2Th.] | d-spacing [Å] |
|---|---|
| 15.5 | 5.7 |
| 16.8 | 5.3 |
| 19.9 | 4.5 |
| 23.1 | 3.8 |
| 27.0 | 3.3 |

Table 7 Some characteristic peaks for Example 25 Form A.

In one aspect the invention relates to a crystalline form of a (S)-4-Amino-N-(2-(4'-carbamoyl-3'-fluorobiphenyl-4-yl)-1-cyanoethyl)tetrahydro-2H-pyran-4-carboxamide having an X-ray diffraction pattern with at least one peak with a 2-theta value selected from the following 2-theta values measured using radiation with a wavelength of 1.5418 Å: 15.5, 16.8, 19.9, 23.1 and 27.0.

In one aspect the invention relates to a crystalline form of a (S)-4-Amino-N-(2-(4'-carbamoyl-3'-fluorobiphenyl-4-yl)-1-cyanoethyl)tetrahydro-2H-pyran-4-carboxamide having an X-ray diffraction pattern with at least 2 peaks with 2-theta values selected from the following 2-theta values measured using radiation with a wavelength of 1.5418 Å: 15.5, 16.8, 19.9, 23.1 and 27.0.

In one aspect the invention relates to a crystalline form of a (S)-4-Amino-N-(2-(4'-carbamoyl-3'-fluorobiphenyl-4-yl)-1-cyanoethyl)tetrahydro-2H-pyran-4-carboxamide having an X-ray diffraction pattern with at least one peak with a d-value selected from the following d-values 5.7, 5.3, 4.5, 3.8 and/or 3.3 Å.

In one aspect the invention relates to a crystalline form of a (S)-4-Amino-N-(2-(4'-carbamoyl-3'-fluorobiphenyl-4-yl)-1-cyanoethyl)tetrahydro-2H-pyran-4-carboxamide having an X-ray diffraction pattern with at least 2 peaks with d-values selected from the following d-m values 5.7, 5.3, 4.5, 3.8 and/or 3.3 Å.

Pharmacological Analysis
Biological Assay
Fluorescence Assay for Recombinant Human (rh) DPP1

The activity of DPP1 was determined by measuring the enzymatic release of aminomethyl coumarin (AMC) from the peptide substrate (H-Gly-Arg-AMC), which leads to an increase in fluorescence intensity at λex=350 nm and λem=450 nm. The assay was carried out in black 384 well plates in a final volume of 50 µl at 22° C. The assay conditions contained the following: 25 mM piperazine buffer pH5.0; 50 mM NaCl, 5 mM DTT; 0.01% (v/v) Triton X-100; 100 µM H-Gly-Arg-AMC and rhDPP1 (~50 µM). Potential inhibitors were made up in DMSO and then diluted in the assay to give a final concentration of not exceeding 1% (v/v) DMSO. A 10-point half-log dilution series of the inhibitors (highest concentration typically 10 µM) was tested and the $pIC_{50}$ determined using a 4-paramater logistic equation in a non-linear curve fitting routine. A standard DPP1 inhibitor (vinyl sulfone, see below, or Example 24 from WO2009/074829) was used as a positive control in the assay. Routinely, inhibitors were pre-incubated with rhDPP1 for 30-60 min prior to the addition of the peptide substrate to start the reaction for a further 60 min at 22° C. After that the plates were immediately read in a fluorescence plate reader using the above emission and excitation wavelengths [modified from Kam, C M, Gotz, M G, Koot, G, McGuire, M J, Thiele, D L, Hudig, D & Powers, J C (2004). Arch Biochem Biophys, 427, 123-134 & McGuire, M J, Lipsky, P E & Thiele, D L (1992). Arch Biochem Biophys, 295, 280-288]. The results obtained are shown in Table I below (N.B. retesting gave $IC_{50}$ results which varied by no more than +/−0.5 from the value given in Table I).

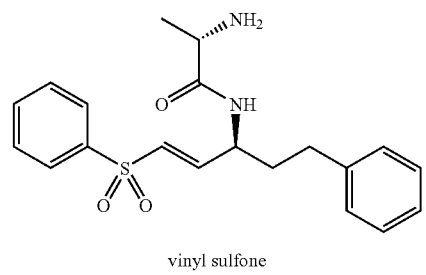

vinyl sulfone

TABLE 1

| Compound of Example | DPP1 activity, $pIC_{50}$ |
|---|---|
| 1 | 9.2 |
| 2 | 9.1 |
| 3 | 9.1 |
| 4 | 9.4 |
| 5 | 9.0 |
| 6 | 9.4 |
| 7 | 9.2 |
| 8 | 9.1 |
| 9 | >9.5 |
| 10 | >9.5 |
| 11 | >9.5 |
| 12 | 9.3 |
| 13 | 9.5 |
| 15 | 9.9 |
| 16 | 9.0 |
| 17 | 9.5 |
| 18 | 9.1 |
| 19 | >9.5 |
| 20 | 9.1 |
| 21 | 9.6 |
| 22 | >9.4 |
| 23 | 9.2 |
| 24 | 9.7 |
| 25 | 8.9 |
| 26 | 8.9 |
| 27 | 8.8 |
| 28 | 9.4 |
| 29 | 9.2 |
| 30 | 8.3 |
| 31 | 8.8 |
| 32 | 8.3 |
| 33 | 9.4 |
| 34 | 8.9 |

Measurement of Stability in Human Microsomes

Hepatic microsomes, prepared from humans by standard ultracentrifugation methods, are used which have been stored at −70° C.

The compounds to be incubated are added from a concentrated stock in DMSO (0.1 mM), 1% v/v to a suspension of microsomal protein (final concentration 1 mg·ml$^{−1}$) in a suitable vial. After a 2 min pre-incubation at 37° C., the cofactor NADPH is added (final concentration of 1 mM) and the reactions allowed to proceed. At appropriate time points (eg. 0, 5, 10, 20 and 30 min), an aliquot (100 µL) is taken from the incubation and added to 2-3 volumes of methanol to terminate the reactions and denature the microsomal enzymes. Control incubations may also be conducted from which NADPH or compound have been omitted. Once the incubations have been quenched, the samples are shaken for 5 min and then centrifuged for 15 min at 3000 rpm and 4° C. The supernatants are taken and analysed by HPLC-MSMS.

The resultant peak areas of the incubated compounds are used to produce a plot of ln [residual concentration] versus time. The t½ and CLint of the loss of the parent compound from the incubation can then be determined from the elimination rate.

The compounds of the present invention in general have good potency, as measured in the fluorescence assay for recombinant human (rh) DPP1, and/or good stability, as measured in the human microsomes assay. Many of the examples have both good potency and good stability.

The invention claimed is:
1. A compound of formula (I)

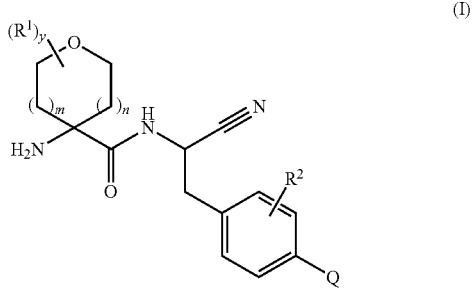

wherein
y represents 0, 1 or 2;
m and n are independently 0, 1, 2 or 3 (such that the sum of m and n is equal to 1, 2 or 3);
$R^1$ is $C_{1-3}$alkyl optionally substituted with one or more substituents selected from halogen, hydroxy or $C_{1-3}$alkoxy;
$R^2$ is selected from hydrogen, halogen, CN, $CF_3$, $C_{1-3}$alkyl or $C_{1-3}$alkoxy;
Q represents phenyl that is optionally substituted by 1 to 3 substituents independently selected from halogen, carboxyl, hydroxyl, oxo, nitro, cyano, mercapto, $C_{1-6}$alkyl group (itself optionally substituted by hydroxyl, $C_{1-6}$alkoxy, $NR^{65}R^{66}$, phenyl or morpholinyl), $C_{3-6}$cycloalkyl, $C_{2-6}$alkenyl, trifluoromethyl, $C_{1-6}$alkoxy (optionally substituted by halogen), $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl;
$R^{53}$ and $R^{54}$ each independently represent hydrogen, $C_{1-6}$alkyl or $C_{3-6}$cycloalkyl, or $R^{53}$ and $R^{54}$ together with the nitrogen atom to which they are attached form a 4- to 7-membered saturated heterocyclic ring;
v is 0, 1 or 2;
$R^{55}$ and $R^{56}$ each independently represent hydrogen, $C_{1-6}$alkyl or $C_{3-6}$cycloalkyl, or $R^{55}$ and $R^{56}$ together with the nitrogen atom to which they are attached form a 4- to 7-membered saturated heterocyclic ring;
$R^{59}$ and $R^{60}$ each independently represent hydrogen, $C_{1-6}$alkyl or $C_{3-6}$cycloalkyl, or $R^{59}$ and $R^{60}$ together with the nitrogen atom to which they are attached form a 4- to 7-membered saturated heterocyclic ring;
each $R^{57}$, $R^{58}$, $R^{61}$, $R^{62}$ $R^{63}$ and $R^{64}$ independently represents a hydrogen atom or a $C_{1-6}$alkyl or $C_{3-6}$cycloalkyl group;
$R^{65}$ and $R^{66}$ each independently represent hydrogen, $C_{1-6}$alkyl or $C_{3-6}$cycloalkyl, or $R^{65}$ and $R^{66}$ together with the nitrogen atom to which they are attached form a 4- to 7-membered saturated heterocyclic ring;
or a pharmaceutically-acceptable salt thereof.

2. A compound or pharmaceutically acceptable salt thereof according to claim 1 wherein the stereochemistry at the carbon bearing the mandatory cyano group has the S stereochemistry.

3. A compound or pharmaceutically acceptable salt thereof according to claim 1 wherein m is 1 and n is 1.

4. A compound according to claim 1 which is of the formula (I'):

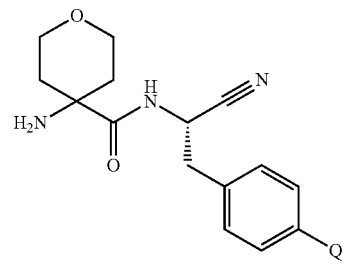

wherein Q is as defined in claim 1;
or a pharmaceutically acceptable salt thereof.

5. A compound according to claim 1 or a pharmaceutically acceptable salt thereof wherein Q is optionally substituted by 1 to 3 substituents independently selected from halogen, carboxyl, hydroxyl, oxo, nitro, cyano, mercapto, $C_{1-6}$alkyl group (optionally substituted by hydroxyl, $C_{2-6}$alkoxy, $NR^{65}R^{66}$, phenyl or morpholinyl), $C_{3-6}$cycloalkyl, $C_{2-6}$alkenyl, trifluoromethyl, $C_{2-6}$alkoxy, $C_{1-6}$alkylcarbonyl, $C_{1-6}$alkylcarbonyloxy, $C_{1-6}$alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, $OS(O_2)R^{64}$, benzyloxy and $C_{1-6}$alkylpiperazinyl wherein the v and R values are as defined in claim 1.

6. A compound according to claim 1 or a pharmaceutically acceptable salt thereof wherein Q is optionally substituted by 1 or 2 substituents independently selected from halogen, carboxyl, cyano, $C_{3-6}$cycloalkyl, trifluoromethyl, —$C(O)NR^{55}R^{56}$, $SO_2NR^{59}R^{60}$, $S(O)_2R^{63}$, $OS(O_2)R^{64}$, wherein the R values are as defined in claim 1.

7. A compound according to claim 1 or a pharmaceutically acceptable salt thereof wherein Q is substituted in the 4-position and optionally substituted in the 3-position.

8. A compound of the formula (I) according to claim 1 selected from:
(S)-4-amino-N-(1-cyano-2-(4'-(trifluoromethyl)biphenyl-4-yl)ethyl)tetrahydro-2H-pyran-4-carboxamide;
(S)-4-amino-N-(1-cyano-2-(4'-(ethylsulfonyl)biphenyl-4-yl)ethyl)tetrahydro-2H-pyran-4-carboxamide;
(S)-4-amino-N-(1-cyano-2-(4'-cyanobiphenyl-4-yl)ethyl)tetrahydro-2H-pyran-4-carboxamide;
(S)-4-amino-N-(1-cyano-2-(4'-fluorobiphenyl-4-yl)ethyl)tetrahydro-2H-pyran-4-carboxamide;
(S)-4-amino-N-(1-cyano-2-(4'-(isopropylsulfonyl)biphenyl-4-yl)ethyl)tetrahydro-2H-pyran-4-carboxamide;
(S)-4'-(2-(4-aminotetrahydro-2H-pyran-4-carboxamido)-2-cyanoethyl)biphenyl-4-yl methanesulfonate;
(S)-4-amino-N-(2-(4'-(azetidin-1-ylsulfonyl)biphenyl-4-yl)-1-cyanoethyl)tetrahydro-2H-pyran-4-carboxamide;
(S)-4-amino-N-(1-cyano-2-(3'-cyanobiphenyl-4-yl)ethyl)tetrahydro-2H-pyran-4-carboxamide;
(S)-4'-(2-(4-Aminotetrahydro-2H-pyran-4-carboxamido)-2-cyanoethyl)biphenyl-3-yl methanesulfonate;

(S)-4-amino-N-(1-cyano-2-(3',4'-difluorobiphenyl-4-yl)
ethyl)tetrahydro-2H-pyran-4-carboxamide;
(S)-4-amino-N-(1-cyano-2-(3'-cyano-4'-methylbiphenyl-
4-yl)ethyl)tetrahydro-2H-pyran-4-carboxamide;
(S)-4-amino-N-(1-cyano-2-(4'-cyano-3'-methylbiphenyl-
4-yl)ethyl)tetrahydro-2H-pyran-4-carboxamide;
(S)-4-amino-N-(1-cyano-2-(4'-methoxybiphenyl-4-yl)
ethyl)tetrahydro-2H-pyran-4-carboxamide;
(S)-4-amino-N-(1-cyano-2-(3'-cyano-4'-fluorobiphenyl-
4-yl)ethyl)tetrahydro-2H-pyran-4-carboxamide;
(S)-4-amino-N-(1-cyano-2-(3'-(methylsulfonyl)biphenyl-
4-yl)ethyl)tetrahydro-2H-pyran-4-carboxamide;
(S)-4-amino-N-(2-(4'-carbamoyl-3'-fluorobiphenyl-4-yl)-
1-cyanoethyl)tetrahydro-2H-pyran-4-carboxamide;
(S)-4-amino-N-(1-cyano-2-(4'-(morpholinosulfonyl)bi-
phenyl-4-yl)ethyl)tetrahydro-2H-pyran-4-carboxam-
ide; and
(S)-4-amino-N-(1-cyano-2-(4'-(4-methylpiperazin-1-yl-
sulfonyl)biphenyl-4-yl)ethyl)tetrahydro-2H-pyran-4-
carboxamide;
or a pharmaceutically acceptable salt salts thereof.

9. A pharmaceutical composition comprising a compound of formula (I) as claimed in claim 1 or a pharmaceutically acceptable salt thereof in association with a pharmaceutically acceptable adjuvant, diluent or carrier.

* * * * *